United States Patent
Prudent

(10) Patent No.: US 10,675,352 B2
(45) Date of Patent: Jun. 9, 2020

(54) EXTRACELLULAR TARGETED DRUG CONJUGATES

(71) Applicant: CENTROSE, LLC, Madison, WI (US)

(72) Inventor: James R. Prudent, Madison, WI (US)

(73) Assignee: Centrose, LLC, Middleton, WI (US)

( * ) Notice: Subject to any disclaimer, the term of this patent is extended or adjusted under 35 U.S.C. 154(b) by 10 days.

(21) Appl. No.: 15/117,672

(22) PCT Filed: Feb. 17, 2015

(86) PCT No.: PCT/US2015/016212
§ 371 (c)(1),
(2) Date: Aug. 9, 2016

(87) PCT Pub. No.: WO2015/123687
PCT Pub. Date: Aug. 20, 2015

(65) Prior Publication Data
US 2016/0346403 A1   Dec. 1, 2016

Related U.S. Application Data

(60) Provisional application No. 61/940,219, filed on Feb. 14, 2014, provisional application No. 61/946,314, filed on Feb. 28, 2014.

(51) Int. Cl.
  A61K 47/68   (2017.01)
  A61K 47/48   (2006.01)
  C07K 16/28   (2006.01)
  A61K 39/00   (2006.01)

(52) U.S. Cl.
  CPC .... A61K 47/48561 (2013.01); A61K 47/6803 (2017.08); A61K 47/6849 (2017.08); A61K 47/6889 (2017.08); C07K 16/2896 (2013.01); A61K 2039/6093 (2013.01); C07K 2319/01 (2013.01); C07K 2319/035 (2013.01)

(58) Field of Classification Search
  CPC ............ A61K 47/6801; A61K 47/6815; A61K 47/6877; A61K 47/6875; A61K 47/6847; A61K 47/6849; A61K 47/6803; A61K 47/6889; A61K 2039/6093; C07K 16/2896; C07K 2319/01; C07K 2319/035
  See application file for complete search history.

(56) References Cited

U.S. PATENT DOCUMENTS

| | | |
|---|---|---|
| 3,773,919 A | 11/1973 | Boswell et al. |
| 4,364,935 A | 12/1982 | Kung et al. |
| 4,816,567 A | 3/1989 | Cabilly et al. |
| 5,047,335 A | 9/1991 | Paulson et al. |
| 5,225,539 A | 7/1993 | Winter |
| 5,229,275 A | 7/1993 | Goroff |
| 5,278,299 A | 1/1994 | Wong et al. |
| 5,362,852 A | 11/1994 | Geoghegan |
| 5,510,261 A | 4/1996 | Goochee et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,739,277 A | 4/1998 | Presta et al. |
| 5,772,997 A | 6/1998 | Hudziake et al. |
| 5,834,597 A | 11/1998 | Tso et al. |
| 6,165,745 A | 12/2000 | Ward et al. |
| 6,821,505 B2 | 11/2004 | Ward |
| 8,153,765 B2 * | 4/2012 | Park .................... A61K 47/6867 530/387.3 |
| 8,877,899 B2 * | 11/2014 | Rojkjaer ............... A61K 31/454 530/387.3 |
| 2002/0004586 A1 | 1/2002 | Aguzzi et al. |
| 2003/0190311 A1 | 10/2003 | Dall'Acqua |
| 2003/0211553 A1 * | 11/2003 | Logtenberg ........ C07K 16/2896 435/7.23 |
| 2004/0229310 A1 | 11/2004 | Simmons |
| 2005/0048572 A1 | 3/2005 | Reilly et al. |
| 2008/0111066 A1 * | 5/2008 | Zhang ................. G01N 33/6842 250/282 |
| 2009/0285780 A1 | 11/2009 | Lee |
| 2010/0017480 A1 | 1/2010 | Jania |
| 2011/0031870 A1 | 2/2011 | Wang |
| 2011/0064752 A1 | 3/2011 | Hutchinson et al. |
| 2012/0122514 A1 | 5/2012 | Cheng et al. |

(Continued)

FOREIGN PATENT DOCUMENTS

| | | |
|---|---|---|
| EP | 0616812 | 9/1994 |
| WO | WO1994/004678 | 3/1994 |

(Continued)

OTHER PUBLICATIONS

Ausiello et al., Tissue Antigen 56: 539-547, 2000.*
Michel de Weers et al., J Immunol 2011; 186:1840-1848; Pre-published online Dec. 27, 2010.*
Rudikoff et al (Proc Natl Acad Sci USA 79: 1979-1983, 1982.*
Yu et al., Investigative Ophthalmology & Visual Science 49(2): 522-527, Feb. 2008.*
Lloyd et al., Protein Engineering, Design & Selection 22:159-168 (Year: 2009).*
Edwards et al., J Mol Biol. 334(1): 103-118 (Year: 2003).*
Becker, "Drug therapy in dental practice: general principles, Part 2—pharmacodynamic considerations," Anesth Prog. 54(1):19-24 (Spring 2007).

(Continued)

Primary Examiner — Phuong Huynh
(74) Attorney, Agent, or Firm — Perkins Coie LLP

(57) ABSTRACT

Extracellular drug conjugates (EDCs) targeting CD38 are useful in the treatment of diseases such as cancer and immune disorders, including asthma.

4 Claims, 6 Drawing Sheets
Specification includes a Sequence Listing.

(56) References Cited

U.S. PATENT DOCUMENTS

| | | | | |
|---|---|---|---|---|
| 2012/0156218 | A1* | 6/2012 | Park | A61K 47/6867 424/158.1 |
| 2012/0178173 | A1 | 7/2012 | Li et al. | |
| 2012/0310140 | A1* | 12/2012 | Kramer | A61K 9/0009 604/20 |
| 2013/0209355 | A1* | 8/2013 | De Weers | C07K 16/2896 424/1.49 |
| 2014/0088056 | A1 | 3/2014 | Ye et al. | |
| 2017/0049908 | A1* | 2/2017 | Prudent | C07K 16/2896 |
| 2019/0008983 | A1* | 1/2019 | Prudent | C07K 16/2887 |

FOREIGN PATENT DOCUMENTS

| | | | |
|---|---|---|---|
| WO | WO1997/000271 | | 1/1997 |
| WO | WO1997/004801 | | 2/1997 |
| WO | WO2001/077342 | | 10/2001 |
| WO | WO2006/099875 | * | 9/2006 |
| WO | WO2011/031870 | * | 3/2011 |
| WO | WO2012092616 | * | 7/2012 |
| WO | WO2012/178173 | | 12/2012 |
| WO | WO2013/085925 A1 | | 6/2013 |

OTHER PUBLICATIONS

Boyd et al., "The effect of the removal of sialic acid, galactose and total carbohydrate on the functional activity of Campath-1H," *Mol. Immunol.* 32(17-18):1311-1318 (Dec. 1995).

Deaglio et al., "CD38 is a signaling molecule in B-cell chronic lymphocytic leukemia cells," *Blood.* 102(6):2146-55 (Sep. 15, 2003).

Deaglio et al., "CD38/CD19: a lipid raft—dependent signaling complex in human B cells," *Blood.* 109:5390-5398 (Jun. 15, 2007).

Deckert et al., "SAR650984, a novel humanized CD38-targeting antibody, demonstrates potent antitumor activity in models of multiple myeloma and other CD38+ hematologic malignancies," *Clin Cancer Res.* 20(17)4574-83 (Sep. 1, 2014).

Ducry, L. et. al. "Antibody-drug conjugates: linking cytotoxic payloads to monoclonal antibodies," *Bioconjugate Chem.* 21(1):5-13 (Jan. 2010).

Ferrero et al., "Characterization and phylogenetic epitope mapping of CD38 ADPR cyclase in the cynomolgus macaque," *BMC Immunol.* 5:21 (Sep. 21, 2004).

Friedman et al., "Engineered affinity proteins for tumour-targeting applications," *Biotechnol Appl Biochem.* 53(Pt 1):1-29 (May 2009).

Funaro et al., "Human CD38 is associated to distinct molecules which mediate transmembrane signaling in different lineages," *Eur J Immunol.* 23(10):2407-2411 (Oct. 1993).

Funaro et al., "Involvement of the multilineage CD38 molecule in a unique pathway of cell activation and proliferation," *J Immunol,* 145(8):2390-6 (Oct. 1990).

Gebauer et al, "Engineered protein scaffolds as next-generation antibody therapeutics," *Curr Opin Chem Biol.* 13(3):245-55 (Jun. 2009).

Griffiths et al., "Human anti-self antibodies with high specificity from phage display libraries," *EMBO J.* 12(2):725-734 (Feb. 1993).

Hamblett et al., "Effects of drug loading on the antitumor activity of a monoclonal antibody drug conjugate," *Clinical Cancer* Res. 10(20):7063-70 (Oct. 15, 2004).

Hicke et a., "Escort Aptamers: A Delivery Service for Diagnosis and Therapy," *J. Clin. Invest.* 106(8):923-928 (Oct. 15, 2000).

Holliger et al., "Diabodies": small bivalent and bispecific antibody fragments, *Proc. Natl. Acad. Sci. USA* 90(14):6444-8 (Jul. 15, 1993).

Hoshino et al., "Mapping of the catalytic and epitopic sites of human CD38/NAD+ glycohydrolase to a functional domain in the carboxyl terminus," *J Immunol.* 158(2):741-7 (Jan. 15, 1997).

Hsu et al., "Differential N-glycan patterns of secreted and intracellular IgG produced in *Trichoplusia ni* cells," *J. Biol. Chem.* 272(14):9062-9070 (Apr. 4, 1997).

Hudson et al., "Engineered antibodies," *Nat. Medicine.* 9(1):129-134, (Jan. 2003).

Jakobovits et al., "Analysis of homozygous mutant chimeric mice: deletion of the immunoglobulin heavy-chain joining region blocks B-cell development and antibody production," *Proc. Natl. Acad. Sci. USA.* 90(6):2551-5 Mar. 15, 1993.

Jia et al., "Formation and function of ceramide-enriched membrane platforms with CD38 during M1-receptor stimulation in bovine coronary arterial myocytes," *Am J. Physiol Heart Circ Physiol.* 295:H1743?H1752 (2008).

Johnson et al., "Human antibody engineering: Current Opinion in Structural Biology," Curr. Opin. Structural Biol. 3(4):564-571 (Aug. 1993).

Kitanaka et al., "CD38 ligation in human B cell progenitors triggers phosphorylation of CD19 and association of CD19 with lyn and phosphatidylinositol 3-kinase," *J Immunol.* 159(1):184-192 (Jul. 1997).

Kitanaka et al., "CD38-mediated signaling events in murine pro-B cells expressing human CD38 with or without its cytoplasmic domain," *J Immunol.* 162(4):1952-1958 (Feb. 15, 1999).

Konopleva et al., "Ligation of cell surface CD38 protein with agonistic monoclonal antibody induces a cell growth signal in myeloid leukemia cells," *J Immunol.* 161(9):4702-8 (Nov. 1, 1998).

Kumagai et al., "Ligation of CD38 suppresses human B lymphopoiesis," *J Exp Med.* 181:1101-10 (Mar. 1, 1995).

Lee et al., "Structural determination of a cyclic metabolite of NAD+ with intracellular Ca2+-mobilizing activity," *J Biol Chem.* 264(3):1608-1615 (Jan. 25, 1989).

Lee et al. "ADP-ribosyl cyclase and CD38. Multi-functional enzymes in Ca+2 signaling," *Adv Exp Med Biol.* 419:411-419 (1997).

Lee et al. "ADP-ribosyl cyclase: an enzyme that cyclizes NAD+ into a calcium-mobilizing metabolite," *Cell Regul.* 2(3):203-209 (Mar. 1991).

Liberatore et al., "Site-directed chemical modification and crosslinking of a monoclonal antibody using equilibrium transfer alkylating crosslink reagents," Bioconjugate Chem., 1(1):36-50 (Jan. 1990).

Lund et al., "CD38 signaling in B lymphocytes is controlled by its ectodomain but occurs independently of enzymatically generated ADP-ribose or cyclic ADP-ribose," *J Immunol.* 162(5):2693-2702 (Mar. 1, 1999).

Mallone et al., "Signaling through CD38 induces NK cell activation," *Int Immunol.* 13(4):397-409 (Apr. 2001).

Manna et al., "Oleandrin suppresses activation of nuclear transcription factor-κB, activator protein-1, and c-Jun $NH_2$-terminal kinase[1]" *Cancer Res.* 60:3838-3847 (Jul. 2000).

Matsumori et al., "Modulation of cytokine production and protection against lethal endotoxemia by the cardiac glycoside ouabain," *Circulation.* 96(5):1501-1506 (Sep. 2, 1997).

Morra et al., "CD38 is functionally dependent on the TCR/CD3 complex in human T cells," *FASEB J.* 12(7):581-92 (May 12, 1998).

Morrison et al., "Chimeric human antibody molecules: mouse antigen-binding domains with human constant region domains," *Proc. Natl. Acad. Sci. USA.* 81(21):6851-5 (Nov. 1984).

Partida-Sanchez et al., "Cyclic ADP-ribose production by CD38 regulates intracellular calcium release, extracellular calcium influx and chemotaxis in neutrophils and is required for bacterial clearance in vivo," *Nat Med.* 7(11):1209-16 (Nov. 2001).

Partida-Sanchez et al., "Regulation of dendritic cell trafficking by the ADP-ribosyl cyclase CD38: impact on the development of humoral immunity," *Immunity.* 20(3):279-91 (Mar. 2004).

Pegram et al., "Inhibitory effects of combinations of HER-2/neu antibody and chemotherapeutic agents used for treatment of human breast cancers," *Oncogene.* 18(13):2241-51 (Apr. 1, 1999).

Polson et al., "Antibody-drug conjugates for the treatment of non-Hodgkin's lymphoma: target and linker-drug selection," *Cancer Res.* 69(6):2358-64 (Mar. 15, 2009).

Sanderson et al., "In vivo drug-linker stability of an anti-CD30 dipeptide-linked auristatin immunoconjugate," *Clinical Cancer Res.* 11(2 Pt 1):843-852 (Jan. 15, 2005).

Shalaby et al., "Development of humanized bispecific antibodies reactive with cytotoxic lymphocytes and tumor cells overexpoiesing the HER2 protooncogene," *J. Exp. Med.* 175(1):217-25 (Jan. 1, 1992).

(56) References Cited

OTHER PUBLICATIONS

Shire et al., "Challenges in the development of high protein concentration formulations," *J. Pharm. Sciences.* 93(6)1 390-402 (Jun. 2004).

Sreenivasan et al., "Oleandrin suppresses activation of nuclear transcription factor-kappa B and activator protein-1 and potentiates apoptosis induced by ceramide," *Biochem. Pharmacol.* 66(11):2223-39 (Dec. 1, 2003).

Tedder et al., "Discontinuous expression of a membrane antigen (HB-7) during B lymphocyte differentiation," *Tissue Antigens.* 24(3):140-9 (Sep. 1984).

Tian et al., "The Na-K-ATPase and Calcium Signaling Microdomains," *Pysiology.* 23:205-211 (2008).

Todisco et al., CD38 ligation inhibits normal and leukemic myelopoiesis, *Blood.* 95(2):535-542 (Jan. 15, 2000).

Waterhouse et al., "Combinatorial infection and in vivo recombination: a strategy for making large phage antibody repertoires," *Nuc. Acids. Res.* 21(9):2265-6 (May 11, 1993).

Yang et al., "Cardiac glycosides inhibit TNF-α/NF-κB signaling by blocking recruitment of TNF receptor-associated death domain to the TNF receptor," *PNAS* vol. 102(27):9631-6 (Jul. 5, 2005).

Zhao et al., "Cytosolic CD38 protein forms intact disulfides and is active in elevating intracellular cyclic ADP-ribose," *J Bio. Chem.* 286(25):22170-17 (Jun. 24, 2011).

Zilber et al., "CD38 expressed on human monocytes: a coaccessory molecule in the superantigen-induced proliferation," *Proc Natl Acad Sci USA.* 97(6):2840-5 (Mar. 14, 2000).

Zubiaur et al., "CD38 ligation results in activation of the Raf-1/mitogen-activated protein kinase and the CD3-zeta/zeta-associated protein-70 signaling pathways in Jurkat T lymphocytes," *J Immunol.* 159(1):193-205 (Jul. 1, 1997).

Zupo et al., "CD38 signaling by agonistic monoclonal antibody prevents apoptosis of human germinal center B cells," *Eur J Immunol.* 24(5):1218-22 (May 1994).

* cited by examiner

EXTRACELLULAR TARGETED DRUG CONJUGATES

PRIORITY CLAIMS

This application is a 35 U.S.C. § 371 U.S. National Stage application of International Application No. PCT/US2015/016212 filed Feb. 17, 2015, which claims priority to U.S. Provisional Patent Application Ser. No. 61/940,219, filed Feb. 14, 2014, and U.S. Provisional Patent Application Ser. No. 61/946,314, filed Feb. 28, 2014, the entire contents of each of which are hereby incorporated by reference and relied upon.

FIELD OF THE DISCLOSURE

The present disclosure provides extracellular drug conjugates useful in the treatment of disease and also as tools for the evaluation of biological systems. The present disclosure relates to the fields of biology, chemistry, medicinal chemistry, medicine, molecular biology, and pharmacology.

BACKGROUND

All fundamental biological processes, including development, immunity, and tumorigenesis, are related to the selective and differential expression of genes in different tissues and cell types. The formation of many malignant tumors has been shown to be associated with the production and/or expression or increased production and/or expression of certain specific cell surface signaling molecules. One of the goals of modern molecular medicine is to find ways to target drugs selectively to reduce or eliminate the drug's off target toxic effects. Delivering drugs to a specific target that is unique to or expressed at higher levels in diseased cells types using targeting moieties such as antibodies, peptides or aptamers has been investigated. Attaching these targeting moieties directly to the drug through linkers or to nanoparticles has also been investigated.

There remains a need for new extracellular-targeted drug conjugates (EDC) for the treatment of disease. The present disclosure meets this need. There also remains a need for methods and reagents to identify and evaluate protein-protein interactions between the Na,K-ATPase and cell signaling pathway proteins on the cell surface. The present disclosure also meets this need.

SUMMARY

The present disclosure generally relates to an extracellular-targeted drug conjugate (EDC) consistent with Formula (I) and comprising three portions: a targeting moiety portion (e.g., [TARGETING MOIETY] in Formula (I)), a non-cleavable linker portion (e.g., [LINKER] in Formula (I)), and a therapeutic or diagnostic agent portion (e.g., [AGENT] in Formula (I)), wherein the three portions are generally associated as follows:

[TARGETING MOIETY]-[LINKER]-[AGENT]    Formula (I)

In another aspect, the present disclosure provides compositions including pharmaceutical formulations and unit dose forms and drug delivery systems comprising EDC consistent with Formula (I) as disclosed herein that are useful in the treatment of disease.

These and other aspects and embodiments of the present disclosure are described in detail below.

DETAILED DESCRIPTION

Figure 1:
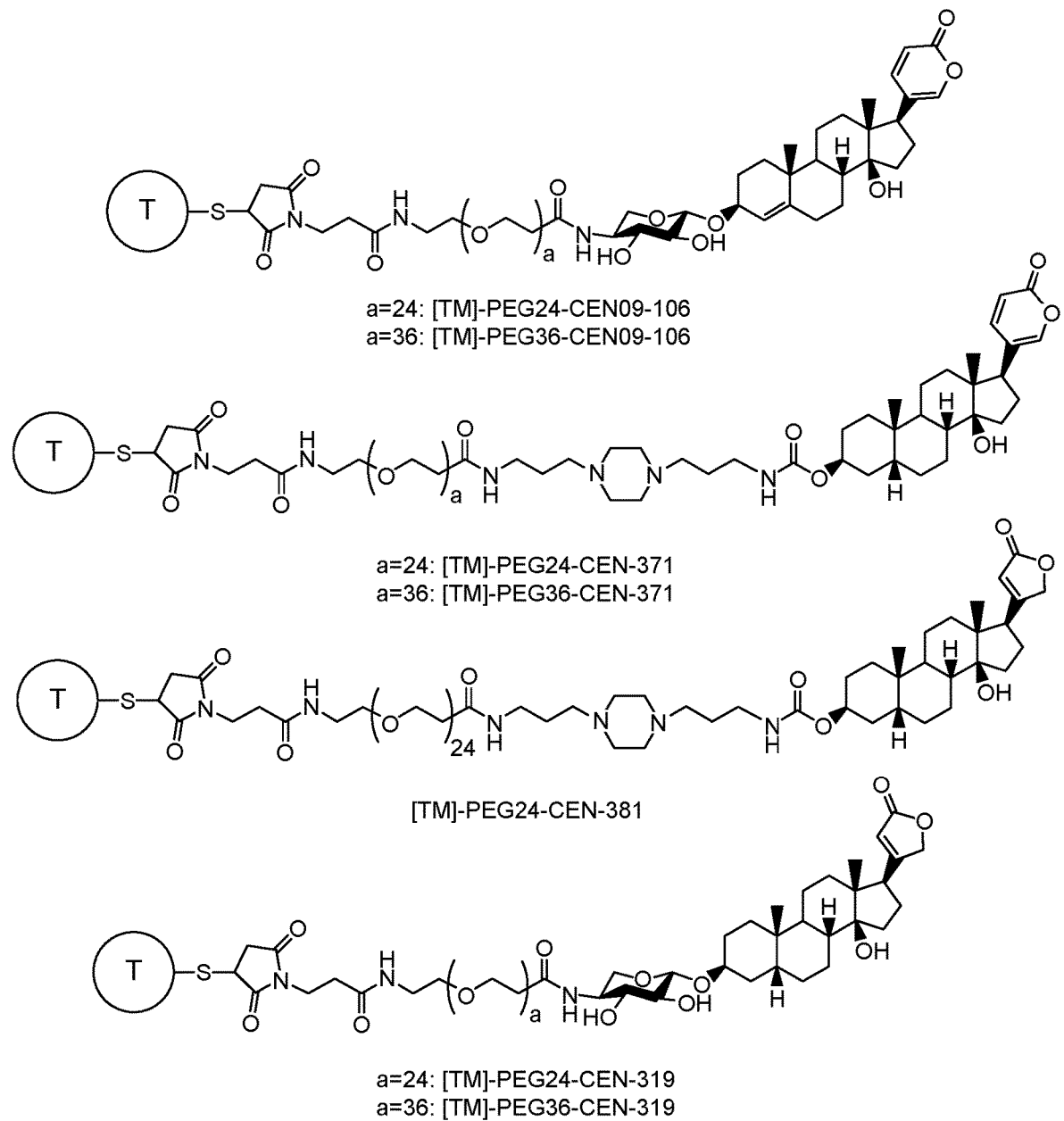
FIG. 1 shows structures for various EDCs of the present disclosure.
Figure 2:
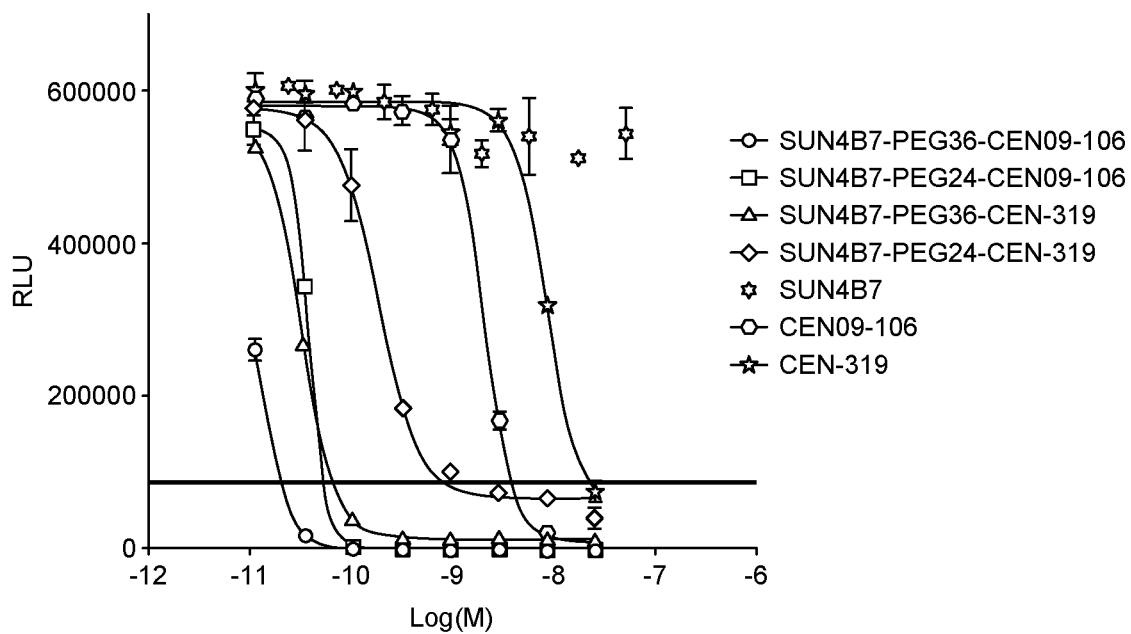
FIG. 2 is a comparison of anti-CD38 targeted EDCs of the present disclosure in SU-DHL-8 cells.
Figure 3:
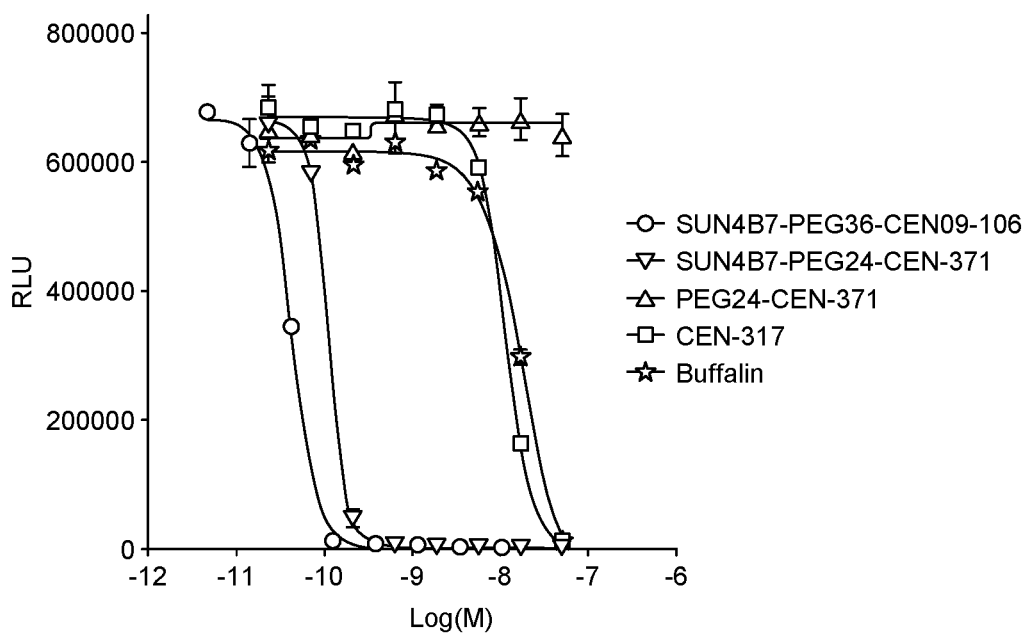
FIG. 3 is a comparison of anti-CD38 targeted EDCs of the present disclosure in SU-DHL-8 cells.
Figure 4:
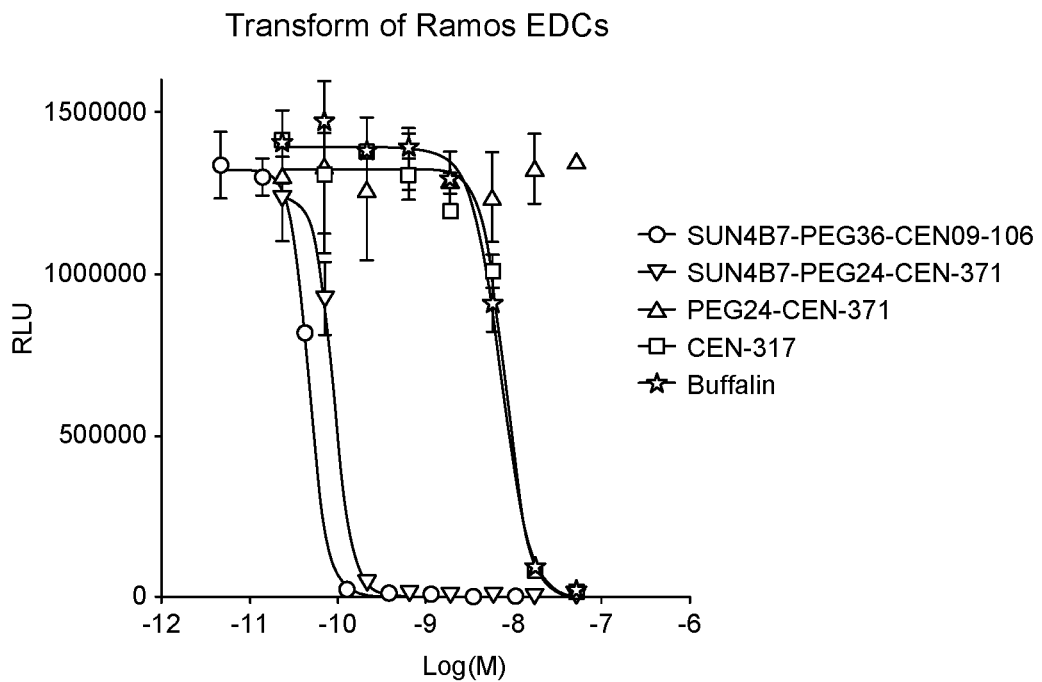
FIG. 4 is a comparison of anti-CD38 targeted EDCs of the present disclosure in Ramos cells.

The present disclosure provides Extracellular-targeted Drug Conjugates or EDC in which the agent moiety (which may be a therapeutic agent such as a drug, a diagnostic agent, or a derivative thereof) and targeting moiety (which may be an antibody targeting moiety such as an anti-CD38 antibody or binding fragment thereof) bind to or act on complexes containing the Na,K-ATPase (encoded by the ATP1 family of genes, including, for example the ATP1A1, ATP1A2, ATP1A3, and ATP1A4 genes). The EDC are useful in a variety of applications, particularly the treatment of human disease, such as cancer and lung disease, including asthma and other diseases involving inflammation of the lung, and other medical conditions.

The present disclosure provides EDC comprising a targeting moiety linked to an agent via a stable or non-cleavable linker (e.g., a linker that has to be intact or non-cleaved for the EDC to exert its maximal therapeutic effect). In various embodiments, the targeting moiety targets CD38 and is an antibody, i.e., an anti-CD38 antibody or a binding fragment thereof. These EDC act on complexes of the Na,K-ATPase and CD38. The EDC of the present disclosure deliver the agent more selectively to target cells and tissues than the agent administered alone. In many embodiments, the EDC contains a targeting moiety that binds (e.g., specifically binds) to CD38 when associated with the Na,K-ATPase in modulating a cell signaling pathway and contains an agent, such as a cardiotonic steroid or cardiac glycoside that binds to the Na,K-ATPase (or to a protein binding site that blocks interaction with the Na,K-ATPase) that is attached to the targeting moiety via a stable or non-cleavable linker. In various embodiments, the linker comprises one or more heteroatoms such as nitrogen, or a glycoside such as an aminoglycoside.

The three portions of the EDC of the present disclosure can thus comprise, consist essentially of or consist of: (1) a targeting moiety that binds to an extracellular target that is not a Na,K-ATPase and that is associated with and in close proximity to the Na,K-ATPase in the disease or other condition of interest, including but not limited to CD38; (2) a stable or non-cleavable linker that connects the targeting moiety to the therapeutic and remains intact (uncleaved) during the time needed for the EDC to bind to its target; and (3) a therapeutic (or diagnostic) agent that acts on or binds to the Na,K-ATPase (or to a site on an associated protein that controls association with the Na,K-ATPase), such as a cardiotonic steroid or cardiac glycoside.

PCT Pub. Nos. 2010/017480; 2011/031870; 2012/122514; and 2012/178173, and all other patents, patent applications, and references from the scientific literature cited herein, are hereby incorporated by reference herein in their entireties.

I. Definitions

The term "antibody" refers to a protein or mixture of proteins that comprise one or more peptidic chains encoded by immunoglobulin genes or fragments thereof (including non-naturally occurring forms thereof produced by genetic engineering) that specifically bind and recognize an epitope of an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. The antibodies comprise IgG (including $IgG_1$, $IgG_2$, $IgG_3$, and $IgG_4$), IgA (including $IgA_1$ and $IgA_2$), IgD, IgE, or IgM, and IgY. As used herein, the term "antibody" is meant to include whole antibodies, including single-chain antibodies, and antigen-binding fragments thereof. Antibodies can also be antigen binding antibody fragments and include, but are not limited to, Fab, Fab' and $F(ab')_2$, Fd, single-chain Fvs (scFv), single-chain antibodies, disulfide-linked Fvs (sdFv), diabodies, triabodies, tetrabodies, minibodies, and fragments comprising either a $V_L$ or $V_H$ domain, and Nanobodies (see PCT publication number WO 94/04678 and Nature Medicine, V9 (1) pp 129-134, 2003). An antibody can be from any animal origin including birds and mammals. Typically, antibodies in commercial or research use are human, murine, rabbit, goat, guinea pig, camelidae (e.g., camel, llamas) horse, or chicken antibodies. "Antibodies", as used herein, includes monoclonal, immunoabsorbed polyclonal, chimeric, and humanized antibodies, as well as intact antibodies and isolated antibodies. Antibodies can be monospecific, bispecific, trispecific or greater multispecificity.

The term "antigen" refers to the substance or target that an antibody or targeting moiety binds. An antigen is characterized by its ability to be "bound" by the antibody or targeting moiety. Antigen can also mean the substance used to elicit the production of targeting moieties, such as the production of antigen specific antibodies through immunizing with the antigen. An antigen is, in many embodiments, a protein, including but not limited to a receptor.

The term "antigen binding site" or "epitope" refers to the portion of the antigen to which a targeting moiety, such as an antibody, binds.

The terms "bind," "binds," and "specifically binds" refers to the ability of a targeting moiety to bind to an extracellular target with greater affinity than it binds to a non-target. In certain embodiments, specific binding refers to binding for an extracellular target with an affinity that is at least 10, 50, 100, 250, 500, or 1000 times greater than the affinity for a non-target.

The term "binding affinity" refers to the strength of interaction between an antibody (or other targeting moiety or drug or other agent) and its antigen (or target) as a function of its association and dissociation constants. Higher affinities typically mean that the targeting moiety has a fast on rate (association) and a slow off rate (dissociation). Binding affinities can change under various physiological conditions due to changes that occur to the antigen or antibody/targeting moiety under those conditions. Binding affinities of the targeting moiety can also change when therapeutic agents and/or linkers are attached. Binding affinities can also change when slight changes occur to the antigen, such as changes in the amino acid sequence or glycosylation of the antigen. Generally, the targeting moieties and agents of the EDCs of the present disclosure have high binding affinities for their respective targets.

The term "cancer" refers to any of a number of diseases characterized by uncontrolled, abnormal proliferation of cells, the ability of affected cells to spread locally or through the bloodstream and lymphatic system to other parts of the body (e.g., metastasize), as well as any of a number of characteristic structural and/or molecular features. A "cancerous cell" or "cancer cell" is understood as a cell having specific structural properties, which can lack differentiation and be capable of invasion and metastasis. Examples of cancers are, breast, lung, brain, bone, liver, kidney, colon, and prostate cancer (see DeVita, V. et al. (eds.), 2005, Cancer Principles and Practice of Oncology, 6th. Ed., Lippincott Williams & Wilkins, Philadelphia, Pa., incorporated herein by reference in its entirety for all purposes).

The term "chimeric antibodies" refers to antibodies in which the Fc constant region of a monoclonal antibody from one species (typically a mouse) is replaced, using recombinant DNA techniques, with an Fc region from an antibody of another species (typically a human). For example, a cDNA encoding a murine monoclonal antibody is digested with a restriction enzyme selected specifically to remove the sequence encoding the Fc constant region, and the equivalent portion of a cDNA encoding a human Fc constant region is substituted. A CDR-grafted antibody is an antibody in which at least one CDR of a so-called "acceptor" antibody is replaced by a CDR "graft" from a so-called "donor" antibody possessing desirable antigen specificity. Generally the donor and acceptor antibodies are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Methods for generating CDR-grafted and humanized antibodies are taught by Queen et al. U.S. Pat. Nos. 5,585,089, 5,693,761 and 5,693,762; and Winter U.S. Pat. No. 5,225,539, which are incorporated herein by reference. Any reference to "antibody" implies a reference to a chimeric antibody.

The term "close proximity" refers to two targets X and Y that are in physical proximity such that, for example, when a targeting moiety (to X) and therapeutic agent (to Y) are conjugated through a linker, and both X and Y are bound to their respective targets, the conjugate induces a desired biological or medical response different from and superior to that induced by either X or Y alone. In one embodiment, the biological or medical response achieved is greater than that observed by either the targeting moiety or therapeutic agent alone. In another embodiment, the biological or medical response achieved is greater than that observed by the additive effects of the targeting moiety and therapeutic agent. For example, when X and Y are located on different molecules, but the molecules are present in the same multi-molecular complex, the targets are in "close proximity" as defined herein. In another example, when X and Y are on the same cell within 200 or fewer Angstroms from one another and act in concert to transmit a signal or otherwise generate a biochemical response, the targets are in "close proximity" to one another as defined herein. When X and Y are on different cells (and/or do not interact with one another), they are not in "close proximity" as defined herein.

The term "effective amount" refers to an amount of EDC, either alone or as a part of a pharmaceutical composition, that is capable of having any detectable, positive therapeutic effect on any symptom, aspect, parameter or characteristics of a disease state or condition when administered to a subject. Such effect need not be absolute to be beneficial.

The term "epitope" refers to groupings of molecules such as amino acid residues or sugar side chains at the surface of antigens that usually have specific three dimensional structural characteristics, as well as specific charge characteristics, and that are capable of specific binding by a monoclonal antibody.

The terms "extracellular" and "cell surface" refers to proteins, antigens, or epitopes located on the external portion of a cell membrane or in the fluids of the circulatory structure (for example, angiotensin converting enzyme is an extracellular protein).

The term "extracellular target" refers to a target that is not a Na,K-ATPase, such as a protein, ganglioside, antigen, and/or epitope located on the cell membrane or in the fluids of the circulatory structure. For example and without limitation, the following are extracellular targets: cell surface receptors, cell surface ion channels, CD (cluster of differentiation or designation) abbreviated proteins. More specifically, and again without limitation, the CD38 is an extracellular targets.

The term "extracellular-targeted drug conjugate" or "EDC" refers to a drug conjugate of the present disclosure in which an antibody or other targeting moiety that targets an extracellular target is linked via a stable or non-cleavable linker to a drug or other agent that binds to an extracellular target. In various embodiments of the present disclosure, the EDC targets CD38 via a targeting moiety that is a CD38 antibody or binding fragment thereof and targets the Na,K-ATPase via an agent that is a cardiotonic steroid.

"Immune disorder" refers to any inflammatory disease or other disease or undesirable condition in which the immune system is improperly functioning. The EDC of the present disclosure are generally useful in treating immune disorders. Many cancers involve an immune disorder. Other immune disorders include disease of the lung, in which inflammation is a causative factor or undesired symptom. Various EDC of the present disclosure are useful in treating immune disorders of the lung, including asthma.

The term "intact antibody" comprises at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as $LCVR^X$ or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, $CDR_1$, $FR_2$, $CDR_2$, $FR_3$, $CDR_3$, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. Examples of binding fragments include, but are not limited to, (i) a Fab fragment, a monovalent fragment consisting of the $V_L$, $V_H$, CL and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature 341: 544-546, 1989), which consists of a $V_H$ domain; and (vi) an isolated complementarily determining region (CDR). As used herein, any general reference to an antibody refers to an intact antibody of any type (naturally occurring, recombinant, chimeric, or humanized) as well as binding fragments.

The term "modified antibodies" refers to antibodies, such as monoclonal antibodies, chimeric antibodies, and humanized antibodies, which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Multiple molecules of a therapeutic agent or multiple different agents can be coupled to one antibody molecule. For example, different moieties can be coupled to an antibody molecule via the same linker, or multiple linkers that provide multiple sites for attachment (e.g., dendrimers) can be used. Any general reference to "antibody" implies a reference to "a modified antibody".

The term "modulate" refers to an interaction of EDC with an extracellular target and the Na,K-ATPase so as to alter, either directly or indirectly, a cell signaling pathway including, for example, to limit or reduce (e.g., inhibit) or increase the activity of the cell signaling pathway.

The term "monoclonal antibody" refers to a preparation of antibody molecules of single molecular composition. A monoclonal antibody composition displays a single binding specificity and affinity for a particular epitope. The term "human monoclonal antibody" refers to antibodies displaying a single binding specificity which have variable and constant regions (if present) derived from human germline immunoglobulin sequences. Human monoclonal antibodies can be produced by a hybridoma which includes a B cell obtained from a transgenic non-human animal, e.g., a transgenic mouse, having a genome comprising a human heavy chain transgene and a light chain transgene fused to an immortalized cell, although the term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology. Any reference to "antibody" implies a reference to "monoclonal antibody".

The terms "non-internalizing targeting moiety" or "non-internalizing antibody" refer to a targeting moiety or antibody, respectively, that has the property of reacting (binding) under physiological conditions (at 37° C. and pH 7) in vivo or in vitro, to antigens outside of a cell, within the circulatory structure, or on a cell surface, and that, when bound to its target antigen, does not enter the cell and become degraded in the lysosome (see *Cancer Res* 2009; 69(6) 2358-64). In this context, "internalizing" and "internalization" refer to the process by which materials enter cells and become degraded, releasing unconjugated agent. In one embodiment, the targeting moiety or antibody, when bound to its target antigen, does not enter the cell and become internalized in an endosome. The target of a "non-internalizing targeting moiety" or "non-internalizing antibody" is referred to herein as a "non-internalizing target," which is a target that does not get internalized into the lysosome as a result of binding to a targeting moiety or antibody. Non-internalizing targets may, however, become internalized into the cell in other biological processes. Examples of non-internalizing targets include, but are not limited to CD38.

The term "non-internalizing agent" refers to an agent (e.g., a therapeutic agent such as a drug) that has the property of reacting in physiological conditions (at 37° C. and pH 7) in vivo or in vitro, with its target (typically, via binding to its receptor) without being internalized into cells.

The terms "pharmaceutically effective amount" and "effective amount" in the context of an amount of drug delivered refer to an amount of a drug that can induce a desired biological or medical response in a tissue, system, animal, or human.

The term "polyclonal antibody" refers to a preparation of more than one (two or more) different antibodies to an antigen. Such a preparation includes antibodies binding to a range of different antigen binding sites.

The term "receptor" refers to an extracellular target protein molecule, embedded in either the plasma membrane or the cytoplasm of a cell, to which one or more specific kinds of signaling molecules may bind. Each cell typically has many receptors, of many different kinds.

The term "stable in the circulatory structure" refers to the property of a compound, such as an EDC, to resist degradation and means that, for example, less than about 50%, or less than about 20%, or typically less than about 2%, of the compound is degraded or cleaved in the circulating blood at about 37° C. for at least about 2 hours.

The term "substantially simultaneously" refers to two or more events that occur at the same time or within a relatively narrow time frame. In various embodiments, substantially simultaneously refers to two or more events that occur within about 60, about 40, about 30, about 20, about 10, about 5, about 2 or about 1 second or less than about one second of each other. For example, EDC of the present disclosure have properties such that targeting moiety binding and agent (drug) action happen substantially simultaneously.

The term "synergistically" refers to an effect of two or more agents when used in combination that is greater than the sum of the effects of both agents when used alone. For example, in the EDC of the present disclosure, the combined therapeutic effects of the interaction of the targeting moiety and the agent (drug) when linked through a linker are greater than the combined individual effects of the targeting moiety and agent when used alone. "Effects" can refer either to binding, therapeutic effect, and/or specificity.

The term "target" refers to the protein, glycoprotein, antigen, carbohydrate or nucleic acid to which a targeting moiety binds and also refers to the protein, glycoprotein, antigen, carbohydrate or nucleic acid to which a therapeutic agent binds. The agent and targeting moiety may bind to different targets in a "target complex", where "target complex" refers to two or more molecules, such as the different subunits of a multi-subunit protein or two different proteins in a multi-protein complex, that are in close physical proximity with one another in vivo.

The term "target cells" refers to the cells that are involved in a pathology and so are preferred targets for therapeutic activity. Target cells can be, for example and without limitation, one or more of the cells of the following groups: primary or secondary tumor cells (the metastases), stromal cells of primary or secondary tumors, neoangiogenic endothelial cells of tumors or tumor metastases, macrophages, monocytes, polymorphonuclear leukocytes and lymphocytes, and polynuclear agents infiltrating the tumors and the tumor metastases.

The interchangeable terms "targeting moiety" and "targeting agent" refer to an antibody, aptamer, peptide, or other substance that binds specifically to a target. A targeting moiety may be an antibody targeting moiety (e.g. antibodies or fragments thereof that bind specifically to a target (i.e., binding fragments thereof) or a non-antibody targeting moiety (e.g. aptamers, peptides, or other substances that bind specifically to a target).

The term "target tissue" refers to target cells (e.g., tumor cells) and cells in the environment of the target cells.

The terms "therapeutic agent" and "drug" and "agent" are used interchangeably herein to refer to a compound that, when present in a therapeutically effective amount, upon binding to a site of action, produces a therapeutic effect, and whose site of action is located or whose effect will be exerted on the surface or inside target cells. By way of example, a therapeutic agent may be a chemical agent, such as an antibiotic or anti-cancer agent, a polypeptide, a protein, or a nucleic acid.

The term "therapeutic effect" refers to the reduction, elimination, and/or prevention of a disease, symptoms of the disease, or side effects of a disease in a subject.

The term "to increase the half-life time" means to increase the mean residence time of a compound, typically a therapeutic agent, in the blood or to reduce the blood or plasmatic clearance compared to a reference compound.

The terms "treating" and "treatment" are used interchangeably to refer to the administration of a therapeutic agent or composition to a patient who has a disease or disorder (e.g., cancer or metastatic cancer), a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease. "Treating" or "treatment" of cancer or metastatic cancer refers to the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters, including the results of an examination by a physician. Accordingly, the term "treating" includes the administration of a therapeutic agent to prevent or delay, to alleviate, or to arrest or inhibit development of the symptoms or conditions associated with a disease, including but not limited to neoplastic disease.

The term "tumor specific antigen" refers to proteins or other molecules that are unique to a tumor or is at least more abundant on tumor cells, relative to normal cells.

II. Na,K-ATPase and Cell Signaling Pathways

The Na,K-ATPase functions as an ion channel and a signal transducer. The Na,K-ATPase is an integral transmembrane protein enzyme that initially was only thought to import potassium ions and export sodium ions against a concentration gradient but more recently has been shown to also transmit signals across the cell membrane. The enzyme is made of three subunits: the alpha, which is the catalytic core and the main target for steroidal compounds; the beta subunit, which is believed to traffic the alpha subunit to specific cell surface locations and is required for alpha subunit activity; and the gamma subunit, which is an auxiliary subunit and which exists in a variety of cell type specific isotypes. The main binding site of cardiac (cardioactive) glycosides to the Na,K-ATPase is located in a cavity formed by the transmembrane helices M1, M2, M4, M5, and M6 [Proc. Natl. Acad. Sci., 2009, 106, 13742-13747]. Cardiac glycosides target the Na,K-ATPase. The therapeutic window of cardiac glycosides, however, is small. In fact, the approved cardiac glycosides (e.g. digoxin or proscillaridin) can cause death in patients at only 2-3 times the level approved for administration Anesth Prog. 2007 Spring; 54(1): 19-24.

The present disclosure arises in part from the discovery that the Na,K-ATPase closely associates (complexes) with CD38 and acts in concert with it to modulate cell signaling pathways and that EDC targeting such complex have remarkable therapeutic activity, particularly in the treatment of cancer and immune disorders, such as asthma. Targeting moieties useful in EDC of the present disclosure are described in the following section.

III. Targeting Moieties

In many embodiments of the EDC of the present disclosure, the targeting moiety may be, without limitation, a human, murine, humanized, or chimeric antibody that does not induce internalization upon target binding and thus is not internalized into a lysosome once bound to its extracellular target.

The EDC of the present disclosure are more selective and/or less toxic than the drug they contain. In the EDC of the present disclosure, the targeting moiety and/or linker can effectively prevent or dramatically reduce the therapeutic (and so reduce toxic, off-target) effect of the drug until the targeting moiety binds to its target. This is an especially important aspect of the present disclosure, given the discovery that the Na,K-ATPase interacts with a myriad of other signaling proteins, creating the potential for significant, undesired "off-target" effects. Thus, the EDC present disclosure the present disclosure are primarily active only when the targeting moiety is bound to its target and in close proximity to the therapeutic agent's target and when the EDC is intact. Taken together, these characteristics allow for more specific and less toxic EDC because the potential of acting on the Na,K-ATPase is only significantly high when the antibody binds to its target. The EDC of the present disclosure are more selective, because both agent and antibody target sites need to be present, and in close proximity to one another, for the EDC to exert a therapeutic effect. The EDC of the present disclosure are less toxic because the agent is linked through a stable linker to the targeting moiety that will selectively bind to its target, keeping the agent in close proximity and thus only able to act on Na,K-ATPases in that close proximity The targeting moieties of EDCs target antigens, such as CD38, that associate with the Na,K-ATPase to modulate a cell signaling pathway.

CD38 (also known as cyclic ADP ribose hydrolase) is a 300 amino acid (45 kD) glycoprotein found on the surface of many immune cells and is encoded by the CD38 gene. CD38 is a type II transmembrane glycoprotein, the extracellular domain acting as an ectoenzyme, catalyzing the conversion of nicotinamide adenine dinucleotide into nicotinamide, adenosine diphosphate-ribose, and cyclic adenosine diphosphate-ribose. In chronic lymphocytic leukemia (CLL), CD38 expression signifies a poor prognosis. CLL is a deadly disease for which more effective treatments are needed. The present disclosure meets this need. CD38 is upregulated in many hematopoeitic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are CD38 negative. CD38 expression in hematopoietic malignancies and its correlation with disease progression makes CD38 an attractive target for antibody therapy (J. Biol. Chem. 2011, 286:22170-22177).

CD38 has been reported to be involved in $Ca^{2+}$ mobilization (M. Morra et al., 1998, FASEB J., 12: 581-592; M. T. Zilber et al., 2000, Proc Natl Acad Sci USA, 97: 2840-2845) and in the signal transduction through tyrosine phosphorylation of numerous signaling molecules, including phospholipase C-γ, ZAP-70, syk, and c-cbl, in lymphoid and myeloid cells or cell lines (A. Funaro et al., 1993, Eur J Immunol, 23: 2407-2411; M. Morra et al., 1998, FASEB J., 12: 581-592; A. Funaro et al., 1990, J Immunol, 145: 2390-2396; M. Zubiaur et al., 1997, J Immunol, 159: 193-205; S. Deaglio et al., 2003, Blood 102: 2146-2155; E. Todisco et al., 2000, Blood, 95: 535-542; M. Konopleva et al., 1998, J Immunol, 161: 4702-4708; M. T. Zilber et al., 2000, Proc Natl Acad Sci USA, 97: 2840-2845; A. Kitanaka et al., 1997, J Immunol, 159: 184-192; A. Kitanaka et al., 1999, J Immunol, 162: 1952-1958; R. Mallone et al., 2001, Int Immunol, 13: 397-409). On the basis of these observations, CD38 was proposed to be an important signaling molecule in the maturation and activation of lymphoid and myeloid cells during their normal development.

The exact role of CD38 in signal transduction and hematopoiesis is still not clear in the literature, especially since most of these signal transduction studies have used cell lines ectopically overexpressing CD38 and anti-CD38 monoclonal antibodies, which are non-physiological ligands. Because the CD38 protein has an enzymatic activity that produces cADPR, a molecule that can induce $Ca^{2+}$ mobilization (H. C. Lee et al., 1989, J Biol Chem, 264:1608-1615; H. C. Lee and R. Aarhus, 1991, Cell Regul, 2: 203-209), it has been proposed that CD38 ligation by monoclonal antibodies triggers $Ca^{2+}$ mobilization and signal transduction in lymphocytes by increasing production of cADPR (H. C. Lee et al., 1997, Adv Exp Med Biol, 419: 411-419). Contrary to this hypothesis, the truncation and point-mutation analysis of CD38 protein showed that neither its cytoplasmic tail nor its enzymatic activity is necessary for the signaling mediated by anti-CD38 antibodies (A. Kitanaka et al., 1999, J Immunol, 162: 1952-1958; F. E. Lund et al., 1999, J Immunol, 162: 2693-2702; S. Hoshino et al., 1997, J Immunol, 158, 741-747).

CD38 knockout mice have been generated. These animals show an almost complete loss of tissue associated NADase activity. Yet, these animals are viable, leading to the conclusion that CD38 and its activities are not necessary for life. These mice do however exhibit a defect in their innate immunity and a reduced T-cell dependent humoral response due to a defect in dendritic cell migration (S. Partida-Sanchez et al., 2004, *Immunity*, 20: 279-291; S. Partida-Sanchez et al., 2001, *Nat Med*, 7: 1209-1216).

In spite of the recent progress in the discovery and development of anti-cancer agents, many forms of cancer involving CD38-expressing tumors still have a poor prognosis. CD38 is expressed at high epitope density by a variety of lymphoid tumors, including most cases of myeloma some cases of AIDS-associated lymphoma and many cases of posttransplant lymphoproliferations. The marked quantitative differences in cell surface expression between normal cells and their leukemic counterparts made CD38 an attractive target for immunotherapy treatment.

CD38 is also involved in main features of asthma such as bronchial hyper-responsiveness and airway inflammation and could represent a new potential therapeutic target for asthma. Abnormal CD38 activity and/or expression may exaggerate airway narrowing observed in patients with asthma. CD38 may have a role in the regulation of different inflammatory genes, such as IL-6 and RANTES which are important in the pathogenesis of asthma. Pro-asthmatic cytokines such as TNFα and IFNs synergistically increase both CD38 protein and mRNA levels by NF-κB activation. On the other hand, CD38 expression is decreased by anti-inflammatory glucocorticoids via inhibition of NF-kB. CD38 expression is also involved in inflammation-associated steroid resistance. CD38 regulation and its correlation with asthma and other inflammatory diseases makes CD38 an attractive target for the development of novel CD38 therapies which could influence the pathophysiology of diseases beyond asthma, like chronic obstructive pulmonary disease and pulmonary fibrosis. There are currently no CD38 specific drugs for asthma at this time.

In certain embodiments, because EDC of the present disclosure target CD38 and can be linked to agents that act to decrease inflammation and/or kill cells expressing CD38, EDC of the present disclosure would be useful in treating patients with various types of asthma including exacerbated asthma that upregulate CD38 on their surfaces. In certain embodiments, because agents of the EDC of the present disclosure also block the activation of NF-κB (nuclear factor kappa-light-chain-enhancer of activated B cells), EDCs of the present disclosure may have use in treating diseases such as those associated with inflammatory and autoimmune diseases, septic shock, viral infection, and improper immune development (2000 Cancer Res. 60, pp 3838-3847 and (2003 Biochem. Pharmacol. 66 pp 2223-2239). In certain embodiments, because agents of the EDC of the present disclosure also reduce cytokine production such as interferon-beta, IL-1 and IL-8, EDCs of the present disclosure can lead to treatment, prevention or amelioration of a number of disorders which are characterized by elevated levels of such cytokines (Circulation. 1997; 96: 1501-1506).

According to certain embodiments, because agents of the EDC of the present disclosure may also reduce inflammation, inflammation associated disorders or diseases could also be treated using the EDC described herein (PNAS 2005 vol. 102 no. 27, 9631-9636, US20140088056 A1). Such disorders or diseases characterized by inflammation may comprise, but are not limited to, asthma, autoimmune diseases, chronic prostatitis, glomerulonephritis, inflammatory bowel disease, pelvic inflammatory disease, reperfusion injury, arthritis, silicosis, vasculitis, inflammatory myopathies, hypersensitivities, migraine, psoriasis, gout, arteriosclerosis, and any combinations thereof.

Exemplary inflammatory diseases include, but are not limited to, rheumatoid arthritis, inflammatory bowel disease, pelvic inflammatory disease, ulcerative colitis, psoriasis, systemic lupus erythematosus, multiple sclerosis, type 1 diabetes mellitus, multiple sclerosis, psoriasis, vasculitis, and allergic inflammation such as allergic asthma, atopic dermatitis, and contact hypersensitivity. Other examples of auto-immune-related diseases or disorders, include but should not be construed to be limited to, rheumatoid arthritis, multiple sclerosis (MS), systemic lupus erythematosus, Graves' disease (overactive thyroid), Hashimoto's thyroiditis (underactive thyroid), Type 1 diabetes mellitus, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anemia, polyarthritis in dogs, Reiter's syndrome, Takayasu's arteritis, warm autoimmune hemolytic anemia, Wegener's granulomatosis, fibromyalgia (FM), autoinflammatory PAPA syndrome, Familial Mediterranean Fever, familial cold autoinflammatory syndrome, Muckle-Wells syndrome, and the neonatal onset multisystem inflammatory disease.

As used herein, an anti-inflammation treatment aims to prevent or slow down (lessen) an undesired physiological change or disorder, such as the development or progression of the inflammation. Beneficial or desired clinical results include, but are not limited to, alleviation of symptoms, diminishment of extent of disease, stabilized (i.e., not worsening) state of disease, delay or slowing of inflammation disease progression, amelioration or palliation of the disease state, and remission (whether partial or total), whether detectable or undetectable. An anti-inflammation treatment can also mean prolonging survival as compared to expected survival if not receiving treatment. An anti-inflammation treatment can also completely suppress the inflammation response.

Multiple attempts to make and use antibodies (monoclonal and bispecific) as well as antibody drug conjugates for treating cancer have been made and shown to be active at killing certain types of human cancer cells (U.S. Pat. No. 8,153,765). Some of the anti-CD38 antibodies have been shown to be able to trigger apoptosis in CD38 positive cells but only in the presence of stroma cells or stroma-derived cytokines. An agonistic anti-CD38 antibody (IB4) has been reported to prevent apoptosis of human germinal center (GC) B cells (S. Zupo et al. 1994, Eur J Immunol, 24: 1218-1222), and to induce proliferation of KG-1 and HL-60 AML cells (M. Konopleva et al. 1998, J Immunol, 161: 4702-4708), but induces apoptosis in Jurkat T lymphoblastic cells (M. Morra et al. 1998, FASEB J, 12: 581-592). Another anti-CD38 antibody T16 induced apoptosis of immature lymphoid cells and leukemic lymphoblast cells from an ALL patient (M. Kumagai et al. 1995, J Exp Med, 181: 1101-1110), and of leukemic myeloblast cells from AML patients (E. Todisco et al. 2000, Blood, 95: 535-542), but T16 induced apoptosis only in the presence of stroma cells or stroma-derived cytokines (IL-7, IL-3, stem cell factor). On the other hand, some CD38 specific antibodies induce apoptosis after cross-linking, but are totally devoid of any apoptotic activity when incubated alone (WO 2006/099875). The SAR650984 like antibodies are capable of killing CD38 positive cells by three different cytotoxic mechanisms: induction of apoptosis, ADCC, and CDC (US20120156218).

In spite of some promising results, these investigations have yet to lead to clinical applications. This is mainly due to negative therapeutic indices when antibody drugs were administered to humans. These effects may be related to CD38's widespread distribution in lymphoid, myeloid, and epithelial cells as well as in specialized tissues and organs including the eyes. Combination therapies have been attempted to increase the therapeutic window (i.e., retinoic acid which up-regulates CD38) yet significant side effects in patients were observed. Thus, if CD38 is to be used as a target for treating cancer, there needs to be a better understanding of how it functions and the discovery of more precise methods of delivering drugs to it such that the drug targets specific diseased cells that express CD38. The EDCs described here where the targeting moiety is an antibody to a CD38 and the drug is a steroid show that certain cells that express CD38 are resistant to the EDC while other cells that also express CD38 are quite sensitive, thus giving evidence that the EDC has the ability to act precisely on cells expressing the complex between the two targets of the EDC.

In view of the multiple functions of human CD38 and the fact that naked CD38 antibodies alone do not provide specificity above the binding of various epitopes on CD38, there is a need for new therapeutics that more specifically modulate particular functions of CD38 on diseased cells.

There are a number of antibodies that bind CD38, some of which are currently being investigated in clinical trials. Table 1 provides a list, without limitation, of antibodies that target CD38, which antibodies, or fragments or derivatives thereof, may be useful in various embodiments of the present disclosure. Many more antibodies that can serve as CD38 targeting moieties of various EDCs of the present disclosure can be found at: [http://www99.mh-hannover.de/aktuelles/projekte/hlda7/hldabase/select.htm] and a list of clinical antibodies at [http://www.imgt.org/mAb-DB/index].

TABLE 1

| Antibody Name | Target Protein | Potential Indications | Reference |
|---|---|---|---|
| HB7, OKT10, Daratumumab, SAR650984, IB4, SUN4B7, IB6, AT1, AT2, UM16, 5D2, BB51, GR7A4, HI157, HIT2, HIT3, MOR202, | CD38 | Cancer, autoimmune and (chronic) inflammatory diseases, such as Type 1 and 2 diabetes, thyroiditis, Graves disease, arthritis, neuroinflammation and asthma. | The Journal of Immunology, 2011, 186: 1840-1848., Blood, 2004; 104 (13) 4269-78, US patent applications US20130209355, US20120156218, |

TABLE 1-continued

| Antibody Name | Target Protein | Potential Indications | Reference |
|---|---|---|---|
| KKIB5, KK9H4 | | | WO2006099875, EP20000202597 BMC Immunology 2004, 5: 21 |

Other examples of antibodies that specifically bind CD38 include, without limitation, the antibodies listed above in Table 1, such as SUN4B7, OKT10, HB7, IB4, AT1, SAR650984 (or 38SB19), Daratumumab, IB6, AT2, UM16, 5D2, BB51, GR7A4, HI157, HIT2, HIT3, and MOR202. Table 2 below provides additional information about various anti-CD38 antibodies listed in Table 1, including their CD38 epitope (binding site) and cross reactivity with macaque CD38.

TABLE 2

| Name | Type | CD38 Epitope (amino acids) | Cross-reacts with Macaque CD38? | Refs* |
|---|---|---|---|---|
| SUN4B7 | IgG1 | 254-275 | YES | 1 |
| OKT10 | IgG1 | 280-298 | YES | 1 |
| HB7 | IgG1 | 254-275 | NO | 1, 2 |
| IB4 | IgG2a | 220-241 and 273-285 | NO | 1 |
| IB6 | IgG2b | ND* | NO | 1 |
| AT1 | IgG1 | 254-275 | YES | 1 |
| SAR650984 or 38SB19 | IgG1 (human) | 107-120, 125, 146, 155, 189, 193, 194 and 226 | ND* | 3 |
| Daratumumab | IgG1 (human) | 233-246 and 267-280 | ND* | 4 |
| MOR202 | IgG1 (human) | ND* | ND* | 5 |

Refs* = references;
ND* = not determined;
1) Tissue Antigens 2000: 56: 539-547 and BMC Immunology 2004, 5: 21;
2) J. Biol. Chem. 2011, 286: 22170-22177;
3) U.S. Pat. No. 8,153,765 and Clin Cancer Res 2014; 20(17); 4574-83;
4) J Immunol 2011; 186: 1840-1848;
5) U.S. Pat. No. 8,877,899.

Human CD38 consists of a short intracytoplasmic tail (21 amino acids), a transmembrane domain (23 amino acids) and a major extracellular domain (256 amino acids). The CD38 extracellular domain, where both receptor and enzymatic activities reside, harbours a twelve cysteine/six disulfide signature common to members of this family, which helps to stabilize the overall structure of the protein (see *BMC Immunol.* 2004; 5:21). The six disulfides of CD38 have previously been shown to be important for its catalytic activities. An epitope map of human CD38 was previously generated using a panel of six specific anti-CD38 monoclonal antibodies, IB4, 1B6, SUN4B7, OKT10, AT1, and AT2 (see *Tissue Antigens* 2000; 56(6):539-47, which is hereby incorporated by reference in its entirety). Results indicated that the monoclonal antibodies may be separated into two broad groups, which recognize totally or partially overlapping epitopes. IB4, AT2 and IB6 antibodies bound one side of CD38, whereas, OKT10, SUN4B7 and AT1 bound the other side of CD38.

Characterization of human CD38 and cynomolgus macaque CD38 using monoclonal antibodies identified additional structural-functional characteristics of CD38 (see *BMC Immunol.* 2004; 5:21, which is hereby incorporated by reference in its entirety). A panel of monoclonal antibodies raised against human CD38, including IB4, 1B6, OKT10, SUN4B7, AT1, and HB7, was assessed for binding to human CD38 and for cross-reactivity to cynomolgus macaque CD38 (*Macaca fascicularis*), which has 92% amino acid sequence identity and 94% similarity with human CD38. Results showed that IB4, IB6, OKT10, SUN4B7, AT1, and HB7 antibodies all bound human CD38. However, only OKT10, SUN4B7, and AT1 antibodies bound to cynomolgus CD38, whereas IB4, IB6 and HB7 antibodies did not bind cynomolgus CD38. The study identified two different epitopes on human CD38 located in two C-terminal disulfide loops. The OKT10 CD38 epitope binding site was mapped to the last (6th) disulfide loop of human CD38 involving residues $Cys^{287}$-$Cys^{296}$ of CD38. Whereas, the SUN4B7 and AT1 CD38 epitope binding site was mapped to the penultimate (5th) C-terminal disulfide loop involving residues $Cys^{254}$-$Cys^{275}$ of human CD38. A homology model of human CD38 derived from Aplyusia ADPR cyclase was generated illustrating footprints of the antibodies near the two C-terminal disulfide loops. Other studies have identified additional CD38 epitopes that are recognized by different monoclonal antibodies.

According to certain embodiments, an example of a targeting moiety in the EDC may be an antibody targeting moiety that specifically binds CD38. The polynucleotide sequence of human CD38 is provided in SEQ ID NO: 1, which encodes the CD38 amino acid sequence provided in SEQ ID NO: 2. In certain embodiments, the targeting moiety in the EDC may be an antibody targeting moiety that specifically binds CD38, which is encoded by the polynucleotide sequence comprising, consisting of, or consisting essentially of SEQ ID NO: 1. In certain embodiments, the targeting moiety in the EDC may be an antibody targeting moiety that specifically binds CD38, which comprises, consists of, or consists essentially of SEQ ID NO: 2. In certain embodiments, the antibody targeting moiety may specifically bind to an epitope located in the extracellular domain of CD38 (i.e., SEQ ID NO: 2). In certain embodiments, the antibody targeting moiety may have the same binding specificity to CD38 (i.e., SEQ ID NO: 2) as any of the antibodies listed in Tables 1 or 2. In certain embodiments, the antibody targeting moiety may bind to the same or substantially similar CD38 epitope as as any of the antibodies listed in Tables 1 or 2. Those of skill in the art will recognize that antibodies to be used in the EDCs described herein can be generated that bind to the same or substantially similar CD38 epitope as any of the antibodies listed in Tables 1 or 2. In various embodiments, the antibody targeting moiety in the EDC is an antibody that may be, for example, a monoclonal antibody. In certain embodiments, the antibody targeting moiety may be, without limitation, a murine antibody, a human antibody, a chimeric antibody, or a humanized antibody of one of the antibodies found in Table 1 or 2 above. In one embodiment, the humanized antibody may be, for example, a humanized form of an anti-CD38 antibody from any non-human source, e.g. murine. In one embodiment, the humanized antibody may be, for example, a humanized form of one of the antibodies found in Table 1 or 2 above. In one embodiment, the humanized antibody may be constructed from heavy and light chain variable sequences that recognizes CD38 on the cell surface. In one embodiment, the antibody may be an antibody fragment, e.g. a Fab fragment. In various embodiments, the antibody of the EDC binds specifically to the extracellular portion of a nucleotide-metabolizing (ecto)-enzymes family member protein such as CD38.

In various embodiments, the EDCs described herein comprise a targeting moiety that targets CD38. In various embodiments, the EDCs described herein comprise a targeting moiety that is an antibody targeting moiety that specifically binds CD38. In various embodiments, the antibody targeting moiety in the EDC is the anti-CD38 murine monoclonal antibody SUN4B7 (IgG1, κ) (see *BMC Immunol.* 2004; 5:21; *Tissue Antigens* 2000; 56(6):539-47). As shown in the Examples below, when comparing targeting moieties, EDCs constructed using SUN4B7 displayed preferred activity since this targeting moiety produced EDCs with the lowest comparable half maximal effective concentration ($EC_{50}$) values and the longest in vivo half-life as determined by PK activity testing. The study provided in Example 5 demonstrates that SUN4B7 is an exemplary targeting moiety for the EDCs provided herein as the EDCs produced with SUN4B7 were the most potent at inducing apoptosis specifically in the cell lines expressing CD38. The SUNB47 epitope binding site on human CD38 was previously characterized in one study as mapping to the 5th C-terminal disulfide loop of human CD38 involving $Cys^{254}$-$Cys^{275}$ (i.e., the disulfide loop includes amino acids 254-275) of the extracellular domain of CD38 (i.e., SEQ ID NO: 2) (see *BMC Immunol.* 2004; 5:21). Additionally, this study indicated that SUN4B7 also bound cynomolgus macaque CD38. In certain embodiments, the antibody targeting moiety in the EDC that specifically binds CD38 may specifically bind to an epitope comprising a disulfide bond of CD38 formed by amino acids 254 (i.e., $Cys^{254}$) and 275 (i.e., $Cys^{275}$) of CD38 (i.e., SEQ ID NO: 2). In certain embodiments, the epitope may comprise the 5th C-terminal disulfide loop of CD38 comprising amino acids 254-275 of CD38 (i.e., SEQ ID NO: 2). In certain embodiments, the epitope may comprise one or more of amino acids 254-275 of CD38 (i.e., SEQ ID NO: 2). In certain embodiments, the antibody targeting moiety may have the same binding specificity to CD38 (i.e., SEQ ID NO: 2) as the SUN4B7 monoclonal antibody. In certain embodiments, the antibody targeting moiety may bind to the same or substantially similar CD38 epitope as SUN4B7. In certain embodiments, the antibody targeting moiety may specifically bind both human CD38 (i.e., SEQ ID NO: 2) and cynomolgus macaque CD38 (i.e., SEQ ID NO: 3). In all of the embodiments described herein, the antibody targeting moiety may be selected from, without limitation, a murine, human, chimeric, humanized antibody or binding fragment thereof.

In certain embodiments, the antibody in the EDC that specifically binds CD38 may be AT1, a monoclonal antibody of the isotype subclass IgG1. The CD38 epitope that is recognized by AT1 is the same epitope recognized by SUN4B7, which is located close to the carboxyl terminus of CD38 mapping to the 5th C-terminal disulfide loop of human CD38 involving $Cys^{254}$-$Cys^{275}$ (i.e., the disulfide loop includes amino acids 254-275) of the extracellular domain of CD38 (i.e., SEQ ID NO: 2) (see *BMC Immunol.* 2004; 5:21). It was previously shown that AT1 also bound cynomolgus CD38. Id. In certain embodiments, the antibody targeting moiety that specifically binds CD38 may specifically bind to an epitope comprising a disulfide bond of CD38 formed by amino acids 254 (i.e., $Cys^{254}$) and 275 (i.e., $Cys^{275}$) of CD38 (i.e., SEQ ID NO: 2). In certain embodiments, the epitope may comprise the 5th C-terminal disulfide loop of CD38 comprising amino acids 254-275 of CD38 (i.e., SEQ ID NO: 2). In certain embodiments, the antibody targeting moiety may have the same binding specificity to CD38 (i.e., SEQ ID NO: 2) as the AT1 monoclonal antibody. In certain embodiments, the antibody targeting moiety may bind to the same or substantially similar CD38 epitope as the AT1 monoclonal antibody. In certain embodiments, the antibody targeting moiety may specifically bind both human CD38 (i.e., SEQ ID NO: 2) and cynomolgus macaque CD38 (i.e., SEQ ID NO: 3). In all of the embodiments described herein, the antibody targeting moiety may be selected from, without limitation, a murine, human, chimeric, humanized antibody or binding fragment thereof.

As shown in the Examples below, EDCs having SUN4B7 as the antibody targeting moiety provided optimal results. Those of skill in the art will recognize that antibodies can be generated that bind to the same or substantially similar CD38 epitope as SUN4B7 (i.e., the 5th C-terminal disulfide loop of CD38 involving $Cys^{254}$-$Cys^{275}$ including amino acids 254-275 of the extracellular domain of CD38 (i.e., SEQ ID NO: 2)). Additionally, in certain embodiments, antibodies for use in the EDC may be generated that bind to the same or substantially similar CD38 epitope as SUN4B7 and also specifically bind cynomolgus macaque CD38 (i.e., SEQ ID NO: 3). In all of the embodiments described herein, the antibodies for use in the EDC may be selected from, without limitation, a murine, human, chimeric, humanized antibody or binding fragment thereof.

Other antibodies that are also useful in the present disclosure have been reported to have the same CD38 epitope binding site as SUN4B7 (i.e., the 5th C-terminal disulfide loop of human CD38 involving $Cys^{254}$-$Cys^{275}$), but do not bind cynomolgus macaque CD38 (i.e., SEQ ID NO: 3). For example, the specificity of HB7 for CD38 was previously established by x-ray crystallography and site-directed mutagenesis studies showing that HB7 directly binds an epitope on human CD38 mapping to a specific disulfide formed by residues $Cys^{254}$ and $Cys^{275}$ of CD38 (see *J Bio. Chem.* 2011; 286(25):22170-7, which is hereby incorporated by reference in its entirety), which is the same epitope binding site that was reported for SUN4B7. Additional studies showed that HB7 does not bind cynomolgus CD38 (see *BMC Immunol.* 2004; 5:21). HB7 (Mouse IgG1, κ) is produced using the hybridoma cell line that has been deposited at the American Type Culture Collection (ATCC) under the deposit number HB-136 (see *Tissue Antigens.* 1984; 24(3):140-9). In certain embodiments, the antibody targeting moiety may have the same binding specificity to CD38 (i.e., SEQ ID NO: 2) as the HB7 monoclonal antibody. In certain embodiments, the antibody targeting moiety may bind to the same or substantially similar CD38 epitope as the HB7 monoclonal antibody. In certain embodiments, the antibody targeting moiety specifically binds human CD38 (i.e., SEQ ID NO: 2), but does not specifically bind cynomolgus macaque CD38 (i.e., SEQ ID NO: 3).

Antibodies useful in the EDCs provided herein may also include any antibody listed in Tables 1 and 2 or binding fragment thereof, or any antibody or binding fragment thereof that binds to the same or substantially similar CD38 epitope as any of the antibodies listed in Tables 1 or 2. In all of the embodiments described herein, the antibody targeting moiety may be selected from, without limitation, a murine, human, chimeric, humanized antibody or binding fragment thereof.

In certain embodiments, the antibody in the EDC that specifically binds CD38 may be OKT10, a monoclonal antibody directed against CD38 that is produced using the hybridoma cell line that was deposited on Nov. 21, 1979 at the ATCC under the deposit number CRL-8022 (see U.S. Pat. No. 4,364,935, which is hereby incorporated by reference in its entirety, for a description of OKT10 and methods of producing OKT10). As shown in Example 5 below, ATRA enhanced cell sensitivity of all cells expressing CD38 that were tested with the EDC constructed with OKT10. Previous studies showed that the CD38 epitope that is recognized by OKT10 is located close to the carboxyl terminus of CD38 and was mapped to the last (6th) disulfide loop of human CD38 involving residues 287-296 of CD38 (see *Tissue Antigens* 2000; 56(6):539-47; *BMC Immunol.* 2004; 5:21). Additionally, it was indicated that OKT10 also bound cynomolgus CD38. In certain embodiments, the antibody targeting moiety may specifically bind to an epitope comprising a disulfide bond of CD38 (i.e., SEQ ID NO: 2) formed by amino acids 287 (i.e., $Cys^{287}$) and 296 (i.e., $Cys^{296}$) of CD38 (i.e., SEQ ID NO: 2). In certain embodiments, the antibody targeting moiety may specifically bind to an epitope comprising the 6th C-terminal disulfide loop comprising amino acids 287-296 of CD38 (i.e., SEQ ID NO: 2). In certain embodiments, the antibody targeting moiety may have the same binding specificity to CD38 (i.e., SEQ ID NO: 2) as the OKT10 monoclonal antibody. In certain embodiments, the antibody targeting moiety may bind to the same or substantially similar CD38 epitope as the OKT10 monoclonal antibody.

In certain embodiments, the antibody in the EDC that specifically binds CD38 may be the anti-CD38 antibody IB4 (see *J. Immunol.* 1997; 158(2):741-7) that is produced using the hybridoma cell line that has been deposited at the ATCC under the deposit number HB-10164. It was previously established that IB4 binds to an epitope located close to the carboxyl terminus of CD38 spanning amino acids 273-285 of human CD38 (see *J. Immunol.* 1997; 158(2):741-7, which is hereby incorporated by reference) and also amino acids 220-241 of human CD38 (see *Tissue Antigens* 2000; 56(6): 539-47, Table 1). Additional studies showed that IB4 does not bind cynomolgus CD38 (see *BMC Immunol.* 2004; 5:21). In certain embodiments, the antibody targeting moiety may specifically bind to an epitope comprising amino acids 220-241 of CD38 (i.e., SEQ ID NO: 2). In certain embodiments, the antibody targeting moiety may specifically bind to an epitope comprising amino acids 273-285 of CD38 (i.e., SEQ ID NO: 2). In certain embodiments, the antibody targeting moiety may specifically bind to an epitope comprising amino acids 220-241 and 273-285 of CD38 (i.e., SEQ ID NO: 2). In certain embodiments, the antibody targeting moiety may have the same binding specificity to CD38 (i.e., SEQ ID NO: 2) as the IB4 monoclonal antibody. In certain embodiments, the antibody targeting moiety may bind to the same or substantially similar CD38 epitope as the IB4 monoclonal antibody as described in *Tissue Antigens* 2000; 56(6):539-47.

In certain embodiments, the antibody in the EDC that specifically binds CD38 may be the anti-CD38 antibody IB6, that is of the isotype subclass, IgG2b (see *Tissue Antigens* 2000; 56(6):539-47). A previous study showed that IB6 does not bind cynomolgus CD38 (see *BMC Immunol.* 2004; 5:21). In certain embodiments, the antibody targeting moiety may have the same binding specificity to CD38 (i.e., SEQ ID NO: 2) as the IB6 monoclonal antibody. In certain embodiments, the antibody targeting moiety may bind to the same or substantially similar CD38 epitope as the IB6 monoclonal antibody.

In certain embodiments, the antibody in the EDC that specifically binds CD38 may be SAR650984 (also known as 38SB19), a humanized monoclonal antibody directed against CD38, which is currently in clinical development. SAR650984 is produced using the hybridoma cell line that has been deposited at the ATCC under the deposit number PTA-7670 (*Clin Cancer Res* 2014; 20(17)4574-83, which is hereby incorporated by reference in its entirety) (also see U.S. Pat. No. 8,153,765, which is hereby incorporated by reference in its entirety, for a description of the 38SB19 antibody and other anti-CD38 antibodies and their sequences including the heavy chain, light chain, and CDR sequences and methods of producing the antibodies). SAR650984 recognizes an epitope on CD38 comprising amino acids 107-120, 125, 146, 155, 189, 193, 194 and 226 of CD38 (see Clin Cancer Res 2014; 20(17); 4574-83, which is hereby incorporated by reference in its entirety). In certain embodiments, the antibody targeting moiety may bind to an epitope comprising amino acids 107-120, 125, 146, 155, 189, 193, 194 and 226 of CD38 (i.e., SEQ ID NO: 2). In certain embodiments, the antibody targeting moiety may bind to an epitope comprising one or more of amino acids 107-120, 125, 146, 155, 189, 193, 194 and 226 of CD38 (i.e., SEQ ID NO: 2). In certain embodiments, the antibody targeting moiety may have the same binding specificity to CD38 (i.e., SEQ ID NO: 2) as the SAR650984 monoclonal antibody. In certain embodiments, the antibody targeting moiety may bind to the same or substantially similar CD38 epitope as the SAR650984 monoclonal antibody. In certain embodiments, the antibody targeting moiety may have the same binding specificity to CD38 (i.e., SEQ ID NO: 2) as any of the anti-CD38 antibodies set forth in U.S. Pat. No. 8,153,765. In certain embodiments, the antibody targeting moiety may comprise one or more of a heavy chain, light chain and CDR of any of the anti-CD38 antibodies set forth in U.S. Pat. No. 8,153,765.

In certain embodiments, the antibody in the EDC that specifically binds CD38 may be daratumumab, a human monoclonal antibody directed against CD38 that is currently in clinical development (see *J Immunol* 2011; 186(3):1840-8, which is hereby incorporated by reference in its entirety). Daratumumab recognizes an epitope on CD38 that is localized to two beta strands in the extracellular domain of CD38 comprising amino acids 233-246 and 267-280 (see *J Immunol* 2011; 186(3):1840-8). In certain embodiments, the antibody targeting moiety may bind to an epitope comprising one or more of amino acids 233-246 and 267-280 of CD38 (i.e., SEQ ID NO: 2). In certain embodiments, the antibody targeting moiety may have the same binding specificity to CD38 (i.e., SEQ ID NO: 2) as the daratumumab monoclonal antibody. In certain embodiments, the antibody targeting moiety may bind to the same or substantially similar CD38 epitope as the daratumumab monoclonal antibody.

In certain embodiments, the antibody in the EDC that specifically binds CD38 may be MOR202, a fully human monoclonal antibody directed against CD38 (see U.S. Pat. No. 8,877,899, which is hereby incorporated by reference in its entirety, for information regarding the MOR202 antibody and other anti-CD38 antibodies and their sequences including the heavy chain, light chain, and CDR sequences and methods of producing the antibodies). In certain embodiments, the antibody targeting moiety may have the same binding specificity to CD38 (i.e., SEQ ID NO: 2) as the MOR202 monoclonal antibody. In certain embodiments, the antibody targeting moiety may bind to the same or substantially similar CD38 epitope as the MOR202 monoclonal antibody. In certain embodiments, the antibody targeting moiety in the EDC that specifically binds CD38 may comprise one or more of a heavy chain, a light chain, and a CDR of the MOR202 antibody or other anti-CD38 antibodies as provided in U.S. Pat. No. 8,877,899.

Antibody targeting moieties in the EDC of the present disclosure typically retain the antigen binding capability of their native, unconjugated counterparts. Thus, antibodies useful in the EDC of the present disclosure are capable of binding specifically to antigens while covalently linked to an agent that acts on the Na,K-ATPase (e.g. scillarenin) through a stable (and, in some embodiments, non-cleavable) linker. Such antigens include proteins or targets that are associated with and in close proximity to the Na,K-ATPase in cells or tissues being targeted for therapeutic intervention (or diagnosis).

Various methods have been employed to produce monoclonal antibodies (MAbs), and these methods are applicable to the production of antibodies for use in the EDC of the present disclosure and so are briefly reviewed below. Hybridoma technology, which refers to a cloned cell line that produces a single type of antibody, uses the cells of various species, including mice (murine), hamsters, rats, and humans. Other methods to prepare MAbs, including chimeric and humanized antibodies, employ genetic engineering, e.g. recombinant DNA techniques.

Polyclonal antibodies may be raised in animals by multiple subcutaneous (sc) or intraperitoneal (ip) injections of the relevant antigen and an adjuvant. Monoclonal antibodies are obtained from a population of substantially homogeneous antibodies, e.g., the individual antibodies comprising the population are identical except for possible naturally occurring mutations that may be present in minor amounts.

Human myeloma and mouse-human heteromyeloma cell lines also have been described for the production of human monoclonal antibodies (Kozbor, (1984) J. Immunol., 133: 3001, and Brodeur et al., Monoclonal Antibody Production Techniques and Applications, pp. 51-63 (Marcel Dekker, Inc., New York, 1987)). Culture medium in which hybridoma cells are growing is assayed for production of monoclonal antibodies directed against the antigen. Binding specificity of monoclonal antibodies produced by hybridoma cells may be determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al (1980) Analyt. Biochem. 107:220.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells (see U.S. Pat. App. Pub. Nos. US20050048572 and US20040229310). Review articles on recombinant expression in bacteria of DNA encoding the antibody include Skerra et al (1993) Curr. Opinion in Immunol. 5:256-262 and Pluckthun (1992) Immunol. Revs. 130:151-188.

In a further embodiment, monoclonal antibodies or antibody fragments can be isolated from antibody phage libraries generated using the techniques described in McCafferty et al (1990) Nature 348:552-554; Clackson et al (1991) Nature 352:624-628; and Marks et al (1991) J. Mol. Biol., 222:581-597 describe the isolation of murine and human antibodies, respectively, using phage libraries. Subsequent publications describe the production of high affinity (nM range) human antibodies by chain shuffling (Marks et al (1992) Bio/Technology 10:779-783), as well as combinatorial infection and in vivo recombination as a strategy for constructing very large phage libraries (Waterhouse et al (1993) Nuc. Acids. Res. 21:2265-2266). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567); and Morrison et al (1984) Proc. Natl. Acad. Sci. USA 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production (Jakobovits et al., (1993) Proc. Natl. Acad. Sci. USA, 90:2551; Jakobovits et al., (1993) Nature 362:255-258; Bruggermann et al., (1993) Year in Immuno. 7:33; and U.S. Pat. Nos. 5,591,669; 5,589,369; and 5,545,807).

Alternatively, phage display technology (McCafferty et al., (1990) Nature 348:552-553) can be used to produce human antibodies and antibody fragments in vitro, from immunoglobulin variable (V) domain gene repertoires from unimmunized donors (Johnson et al., (1993) Curr. Opin. Structural Biol. 3:564-571). A repertoire of V genes from unimmunized human donors can be constructed and antibodies to a diverse array of antigens (including self-antigens) can be isolated essentially (Marks et al., (1991) J. Mol. Biol. 222:581-597; Griffith et al., (1993) EMBO J. 12:725-734; U.S. Pat. Nos. 5,565,332 and 5,573,905). Human antibodies may also be generated by in vitro activated B cells (U.S. Pat. Nos. 5,567,610 and 5,229,275). Human anti-ErbB2 antibodies have been described (U.S. Pat. No. 5,772,997 and PCT Pub. No. WO 97/00271).

Various techniques have been developed for the production of antibody fragments. Traditionally, these fragments were derived via proteolytic digestion of intact antibodies (see Morimoto et al., (1992) J. Biochem. Biophys. Methods 24:107-117; and Brennan et al., (1985) Science 229:81). Antibody fragments can also be produced directly by recombinant host cells and the antibody phage libraries discussed above. Fab'-SH fragments can be directly recovered from E. coli and chemically coupled to form F(ab')$_2$ fragments (Carter et al (1992) Bio/Technology 10:163-167). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (v (sFv) dimers (Gruber et al., (1994) J. Immunol. 152:5368). Techniques for generating bispecific antibodies from antibody fragments have also been described, such as using chemical linkage wherein intact antibodies are proteolytically cleaved to generate F(ab')$_2$ fragments (Brennan et al., (1985) Science 229:81). Fab'-SH fragments can be recovered from E. coli and chemically coupled to form bispecific antibodies (Shalaby et al., (1992) J. Exp. Med. 175:217-225. The "diabody" technology provides an alternative method for making bispecific antibody fragments (Hollinger et al., (1993) Proc. Natl. Acad. Sci. USA 90:6444-6448).

Antibodies with more than two valencies can be employed in various embodiments of the EDC of the present disclosure. Multivalent, "Octopus" antibodies with three or more antigen binding sites and two or more variable domains can be readily produced by recombinant expression of nucleic acid encoding the polypeptide chains of the antibody (US Pat. App. Pub. No. US2002/0004586 and PCT Pub. No. WO 01/77342). For example, trispecific antibodies can be prepared (Tutt et al., (1991) J. Immunol. 147:60).

Amino acid sequence modification(s) of antibodies are contemplated by the present disclosure. For example, mutants and various isoforms of antibodies which bind to tumor-associated or other antigens are contemplated to improve the binding affinity and/or other biological properties of the antibody and/or allow for site specific conjugation of the linker and/or therapeutic agent to the antibody. Amino acid sequence variants of an antibody are prepared by introducing appropriate nucleotide changes into the nucleic acid encoding the antibody, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is "alanine scanning mutagenesis" (Cunningham and Wells (1989) Science 244:1081-1085) where an amino acid residue, or group of target residues, are identified (e.g., charged residues such as arg, asp, his, lys, and glu) and replaced by a neutral or negatively charged amino acid, such as alanine or polyalanine, to optimize the interaction of the amino acids with antigen. Amino acid sequence insertions include amino- and/or carboxyl-terminal fusions ranging in length from one residue to polypeptides containing a hundred or more residues, as well as intrasequence insertions of single or multiple amino acid residues.

The amino acid sequence of an antibody is usually altered by altering the underlying nucleic acid sequence. Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (see US Pat. App. Pub. No. US20030190311, and U.S. Pat. Nos. 6,821,505; 6,165,745; 5,834,597; 5,648,260; and 5,624,821). PEGylation can also be used to increase the half life of an EDC of the present disclosure.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), or the extent of glycosylation. Antibodies may be glycosylated at conserved positions (N-linked or O-linked) in their constant regions (Hse et al., (1997) J. Biol. Chem. 272:9062-9070; Jefferis and Lund, (1997) Chem. Immunol. 65:111-128; Wright and Morrison, (1997) TibTECH 15:26-32). The oligosaccharide side chains of the immunoglobulins affect the protein's function (Boyd et al., (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner (1996) Current Opin. Biotech. 7:409-416). Oligosaccharides may also serve to target a given glycoprotein to certain molecules based upon specific recognition structures (Malhotra et al., (1995) Nature Med. 1:237-243; Umana et al., (1999) Nature Biotech. 17:176-180). Removal of the oligosaccharides may optimize antigen binding and other properties of the antibody (Boyd et al., (1996) Mol. Immunol. 32:1311-1318).

Factors which affect glycosylation during recombinant production of antibodies include growth mode, media formulation, culture density, oxygenation, pH, purification schemes and the like (U.S. Pat. Nos. 5,047,335; 5,278,299; and 5,510,261). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-.beta.-galactosidase), elimination using harsh alkaline environment to release mainly O-linked structures, and chemical methods using anhydrous hydrazine to release both N- and O-linked oligosaccharides.

The antibodies in the EDC of the present disclosure can be for example and without limitation monoclonal antibodies, polyclonal antibodies, modified antibodies, chimeric antibodies or improved antibodies as described in the definitions provided above. For example, modern alternative strategies now allow for the production of fully humanized antibodies to reduce the immunogenicity of the antibody. In addition, smaller antibody fragments can be engineered, including antigen binding Fabs, Fvs, scFv, and minibodies, and the antibody can also be enhanced to increase the antibody's affinity, stability, and expression level (see Nat Med. 2003 January; 9(1):129-34).

In an alternative embodiment of the present disclosure, the targeting moiety of the EDC of the present disclosure is not an antibody but is instead a peptide or protein or peptidomimetic that is the functional equivalent, in terms of targeting, of an antibody. For example and without limitation, the antibody can be replaced by any of a number of small and robust non-immunoglobulin "scaffolds" that can be equipped with prescribed binding functions using the methods of combinatorial protein design. Such scaffolds are described in various reviews (see, e.g. "Engineered protein scaffolds as next-generation antibody therapeutics" in Curr Opin Chem Biol. 2009 June; 13(3):245-55 and "Engineered affinity proteins for tumour-targeting applications" in Biotechnol Appl Biochem. 2009 May; 53(Pt 1): 1-29).

In another alternative embodiment of the present disclosure, the targeting moiety of the EDC of the present disclosure is not an antibody but is instead a DNA, RNA, or oligonucleotide mimetic that is the functional equivalent, in terms of targeting, of an antibody. For example, SELEX methods can be used to identify DNA or RNA or modifications thereof with prescribed binding functions. Aptamers are polymers of RNA or DNA oligonucleotides or modifications thereof that are isolated by the systematic evolution of ligands like the exponential enrichment SELEX process (see Hicke and Stephens, 2000, "Escort Aptamers: A Delivery Service for Diagnosis and Therapy," J. Clin. Invest., 106(8), pp. 923-928).

Typically, the targeting moiety (the anti-CD38 antibody or binding fragment thereof or other targeting moiety) will be purified, often to greater than 95% by weight (as determined, for example, by the Lowry method), and often to more than 99% by weight prior to use in forming an EDC of the present disclosure. Once a targeting moiety or suitable portion thereof for use in the desired synthetic route for the EDC of interest is available, it can be linked to a therapeutic agent, which may be for example and without limitation a cardiotonic steroid, by any of a variety of linkers and linking technologies, as discussed in the following section.

IV. Linker Portion

In an EDC of the present disclosure, the agent is coupled to the targeting moiety portion via a stable linker. The linker is long (generally at least about 50 Angstroms in length and more typically 100 Angstroms in length, or as long as about 200 Angstroms or even 300 Angstroms in length or longer), flexible and extendable, and in some embodiments positively charged, including by the presence of one or more heteroatoms (e.g., nitrogen) in an alkyl chain that forms all or part of the linker portion and is attached to the agent. In one important aspect, the present disclosure provides new linkers for linking anti-CD38 antibodies or other targeting moieties to cardiotonic steroids, cardiac glycosides, and other agents that target the Na,K-ATPase and other agents generally, and compositions and compounds in purified form useful in their synthesis, methods for which are also provided by the present disclosure. Coupling of a linker (e.g., as a completed linker portion) or formed step-wise, for example by coupling a targeting moiety bound to a first portion of the linker and then with either further portions of the linker or directly to an agent portion, which may optionally be in a synthetic intermediate in which the agent is bound to a second portion of the linker.

The linkers employed in the EDC of the present disclosure are stable. For example, after administration, the EDC is stable and remains intact, e.g. the targeting moiety remains linked to the agent via the linker. The linkers are stable outside the target cell and remain uncleaved for efficacy. An effective linker will: (i) maintain the specific binding properties of the antibody; (ii) allow delivery of the conjugate or agent; (iii) remain stable and intact, e.g. not cleaved, for as long as the antibody and/or agent remains stable and intact; and (iv) maintain a cytotoxic, cell-killing effect or a cytostatic effect of the agent while the EDC is intact. By way of example, stable linkers are those that, when in an EDC of the present disclosure, show minimal (e.g., less than 10%) cleavage while present in the circulatory structure, at the surface of target tissue, at the surface of target cell, or in the extracellular matrix for a period of at least 4 to 8 hours or longer, such as 8 to 24 hours, or 1 to 10 days or longer; non-cleavable linkers are stable in these conditions for longer periods, including periods as long as 20 days or longer (Durcy, L. et. al. Bioconjugate Chem. 2010, 21, 5-13).

The length of a suitable linker may be determined by experimental measurements, for example by testing multiple linker lengths in the assay used to determine activity of the resulting EDC of the present disclosure. For example, if linker length is too short (not allowing the drug and targeting moiety to reach their binding sites simultaneously), one can readily identify and correct the problem to provide an EDC of the present disclosure. Typically, the linker length will be in the range of about 50 to about 300 Angstroms, or about 50 to about 200 Angstroms. The linker length and composition is selected to ensure that the EDC remains stable in the circulatory structure where enzymes and other environmental substances may otherwise break it down and to reflect the distance from where the targeting moiety binds to its antigen and where the agent acts on its target. A wide variety of linkers that comply with these requirements are available or can be synthesized, which creates a very large class of EDC provided by the present disclosure, particularly when one considers the wide variety of linkers, therapeutic agents and targeting moieties that can be employed in the EDC of the present disclosure.

The linker, if conceptualized as a discrete entity instead of part of an EDC, is a monofunctional or multifunctional moiety that can be used to link one or more drugs to an antibody to form an EDC. EDC can be conveniently prepared using a linker having reactive functionality for binding to the drug and to the antibody. For example, a cysteine thiol, or an amine, e.g. a sulfur atom of a reduced disulfide bond, or an N-terminus or amino acid side chain such as lysine or histidine, of an antibody can form a bond with a functional group of a linker reagent or drug-linker reagent (composed of the agent and linker).

In some embodiments, the linker includes one or more ethylene glycol units (e.g., a polyethylene glycol). Without wishing to be bound by theory, it is believed that the presence of ethylene glycol units in the linker imparts flexibility, tunable spacing between the agent and the targeting moiety, and desirable solubility characteristics to the EDCs. In some embodiments, the linker includes the ethylene glycol unit(s) in close proximity to the targeting moiety, for example bound directly to the targeting moiety or bound to the targeting moiety by a short alkyl chain (e.g., a functionalized alkyl chain having from 2 to about 20 atoms). In some embodiments, the linker includes a polyethylene glycol sub-unit having from about 6 to about 60 ethylene glycol repeat units, for example about 6, about 12, about 24, about 36, about 48, or about 60 ethylene glycol repeat units. In some preferred embodiments, the linker includes 24 ethylene glycol repeat units (also referred to herein as "PEG24"). In other preferred embodiments, the linker includes 36 ethylene glycol units ("PEG36").

In some embodiments, the linker includes a second portion which includes at least one heteroatom (e.g., nitrogen). Without wishing to be bound by theory, it is believed that the presence of the heteroatom(s) such as nitrogen in the linker enhances the solubility properties of the EDCs at physiological pH. Accordingly, the optimum linker, including the optimum number of heteroatoms included therein, may vary for different combinations of agent portions and targeting moiety portions.

In some embodiments, the heteroatom(s) are included in an alkyl chain (e.g., a functionalized heteroalkyl chain). The heteroalkyl chain may be bound to the agent at any suitable location such that the activity of the agent is not substantially diminished (e.g., through the C3 carbon when the agent is a cardiotonic agent). In some embodiments, the heteroalkyl chain is bound to the targeting moiety directly, but in preferred embodiments the heteroalkyl chain is bound to the targeting moiety by one or more ethylene glycol units (e.g., a polyethylene glycol such as PEG24). In some embodiments, the linker includes a least one glycoside residue (e.g., an aminoglycoside), which is typically attached to the agent of the EDC.

In some embodiments, linkers of the present disclosure have a formula consistent with that of Formula (II):

Formula (II)

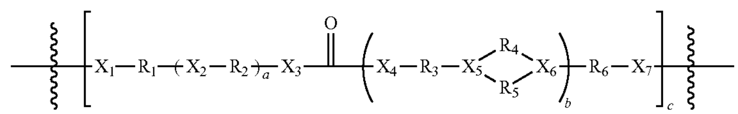

wherein:

$X_1$ is optionally present and, when present, may include (before coupling with the targeting moiety) a group reactive with a portion of the targeting moiety. For example and without limitation, when the targeting moiety is an antibody, antibody fragment, protein or peptide, the linker (before coupling with the targeting moiety) may include an electrophilic group, such as a maleimide, to enable coupling with the targeting moiety through a nucleophilic atom, such as a sulfur atom from a reduced disulfide bond, or a nitrogen atom from a lysine or histidine residue. Thus, in some embodiments, $X_1$ of Formula (II) may be

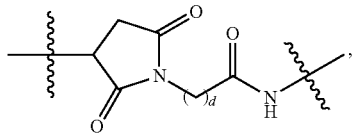

wherein d is 0 to 6;

each of $X_2$, $X_3$ and $X_4$ may optionally be present and may individually be selected from alkyl, ketone, —C(O)NH—, —C(O)NR$_8$—, —O—, —S—, —NH—, —NR$_9$—, wherein $R_8$ and $R_9$ are individually selected from alkyl (e.g., methyl), heteroalkyl, aryl, and heteroaryl;

$X_5$ and $X_6$ are each individually selected from CR$_{10}$ and N, wherein R$_{10}$ is H, branched alkyl, unbranched alkyl, saturated alkyl, or unsaturated alkyl;

$X_7$ is optionally present and may be selected from —C(O)—, —OC(O)—, —NHC(O)—, —NR$_{11}$C(O)—, wherein R$_{11}$ is H, branched alkyl, unbranched alkyl, saturated alkyl, or unsaturated alkyl;

$R_1$ is optionally present and may be selected from branched alkyl, unbranched alkyl, saturated alkyl, or unsaturated alkyl;

each of $R_2$, $R_3$ and $R_6$ may optionally be present and may individually be selected from branched alkyl, unbranched alkyl, saturated alkyl, and unsaturated alkyl;

each of $R_4$ and $R_5$ are optionally present and may be selected from branched alkyl, unbranched alkyl, saturated alkyl, or unsaturated alkyl, with the proviso that at least one of $R_4$ and $R_5$ must be present;

a is 0 to 99;
b is 0 to 99; and
c is 0 to 99.

In some preferred embodiments, the linker has a formula of Formula (II) wherein $X_1$ is

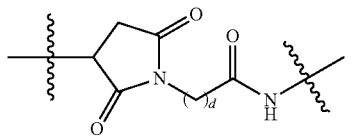

and d is 2; $X_2$ is —O—; $X_3$ is null; $X_4$ is —NH—; $X_5$ and $X_6$ are each N; $X_7$ is —NHC(O)—; $R_1$ is —CH$_2$CH$_2$—; $R_2$ is —CH$_2$CH$_2$—; $R_3$ and $R_6$ are each —CH$_2$CH$_2$CH$_2$—; $R_4$ and $R_5$ are each —CH$_2$CH$_2$—; a is 1-50; b is 1-10; and c is 1-10.

In one particularly preferred embodiment, the linker has a formula of Formula (II) wherein: $X_1$ is

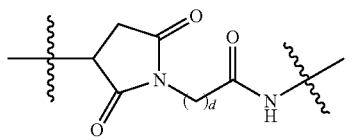

and d is 2; $X_2$ is —O—; $X_3$ is null; $X_4$ is —NH—; $X_5$ and $X_6$ are each N; $X_7$ is —NHC(O)—; $R_1$ is —CH$_2$CH$_2$—; $R_2$ is —CH$_2$CH$_2$—; $R_3$ and $R_6$ are each —CH$_2$CH$_2$CH$_2$—; $R_4$ and $R_5$ are each —CH$_2$CH$_2$—; a is 24 or 36; b is 1; and c is 1.

In another particularly preferred embodiment, the linker has a formula of Formula (II) wherein: $X_1$ is

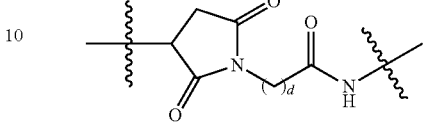

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24 or 36; b is 1; and c is 1.

In another particularly preferred embodiment, the linker has a formula of Formula (II) wherein: $X_1$ is

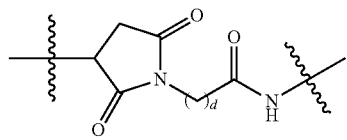

and d is 2; $X_2$ is —O—; $X_3$ is null; $X_4$ and $X_5$ are each —NH—; $X_6$ is null; $N_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24 or 36; b is 1; and c is 1.

V. Agent Portion

A wide variety of agents are suitable for use in the EDC of the present disclosure. Generally, the agent binds to Na,K-ATPase, or is otherwise capable of affecting pump activity (e.g., reduces pump activity or stops pump activity). Typically, the agent is a "non-internalizing therapeutic agent" that acts directly on the Na,K-ATPase, e.g., at the alpha subunit. In other embodiments of the present disclosure, the agent acts to inhibit the interaction of the Na,K-ATPase and a cell surface pathway signaling protein associated therewith. In various embodiments of the present disclosure, the agent may be a steroid, a modified steroid, a steroid derivative (e.g., a functionalized steroid), a cardiotonic steroid, a cardiac glycoside, or a cardenolide. In some embodiments, the agent is bufalin, scillarenin, or digitoxigenin. In other embodiments, the agent is a cardiac glycoside or an aglycone of a cardiac glycoside, such as digitoxin, digoxin, ouabain or proscillaridin.

In preferred embodiments of the present disclosure, the agent is a cardenolide, cardiotonic steroid or cardiac glycoside of Formula (III) below:

Formula (III)

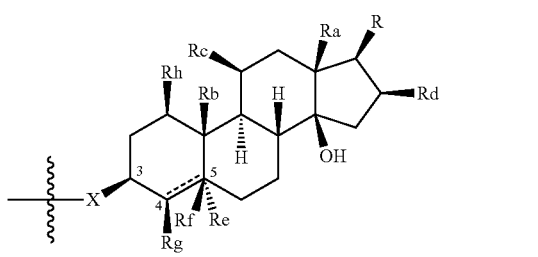

where the steroidal rings are either saturated, unsaturated or a combination thereof,

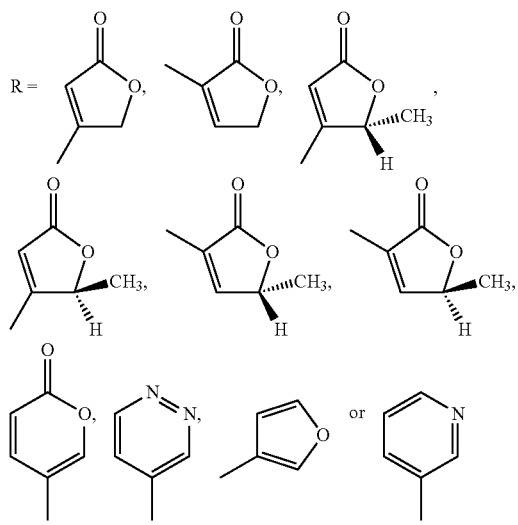

or R is a side chain found on various corticosteroids such as CHOCH$_3$, O, OH or a branched alkane. $R_a$ is CH$_3$; $R_b$ is CH$_3$, CH$_2$OH, or CHO; $R_c$ is H, OH or CH$_3$COO; $R_d$ is H, OH or CH$_3$COO; $R_e$ is H, or $R_e$ is no group when $R_f$ is H or OH or when a double bond exists between carbons C4 and C5; $R_f$ is H or OH or, when $R_e$ is H or a double bond exists between carbons C4 and C5, $R_f$ is no group; $R_g$ is H or, when $R_e$ is H or a double bond exists between carbons C4 and C5, $R_g$ is no group; $R_h$ is H or OH; X has a general formula of "—Y—Z—" wherein Y is covalently bound to carbon C3 and is selected from O, S, N(OR'), N(SR'), and N(NR'), and Z is null or a glycoside such as a 3-amino-riboside, a 4-amino-riboside, a 3-amino-xyloside, and/or a 4-amino-xyloside; and R' is an alkyl or aryl group.

In some embodiments, the agent is a pharmaceutically acceptable ester, derivative, conjugate, hydrate, solvate, prodrug, or salt of a cardenolide, cardiotonic steroid, or cardiac glycoside of Formula (III), or mixture of any of the foregoing.

In some embodiments, the agent portion of an EDC is bufalin. In other embodiments, the agent portion of an EDC is scillarenin. In still other embodiments, the agent portion of an EDC is digitoxigenin.

VI. EDC Construction, Screening, and Specific Embodiments

The present disclosure provides EDCs that generally comprise a targeting moiety, such as an anti-CD38 antibody, linked to an agent portion, such as a cardiotonic steroid, via a stable (and, in some embodiments, non-cleavable) linker.

Generally, in EDC of the present disclosure, the site where the agent portion is attached to the linker is at a position where the linker attachment only minimally interferes or does not interfere at all with the agent's desired activity in the EDC, e.g., binding to the Na,K-ATPase. While embodiments of the present disclosure illustrate the linker bound through C3 of these cardiotonic steroids, other attachments points are possible and within the scope of the present disclosure.

Generally, the linker portion is attached to the targeting moiety through a reactive group of the peptide, such as a thiol (e.g., obtained by first reducing a disulfide bond) or an amine (e.g., from a lysine or histidine residue). In some preferred embodiments, the reactive group or atom of the targeting moiety is a sulfur atom in a hinge region of the antibody (e.g., anti-CD38 antibody).

Accordingly, in some embodiments the EDCs of the present disclosure have a structure as shown in Formula (IV), below:

Formula (IV)

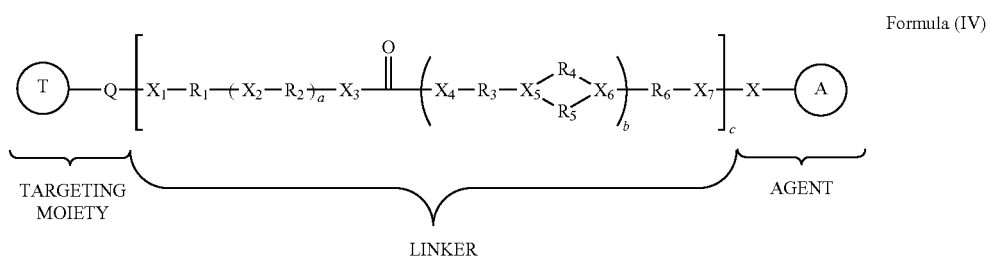

wherein Q is a reactive atom of the targeting moiety, such as a sulfur or a nitrogen atom, and wherein the linker and the agent (including substituent X of the agent) are as described above.

In some embodiments, the EDC has a structure as shown in Formula (IVa) below:

Formula (IVa)

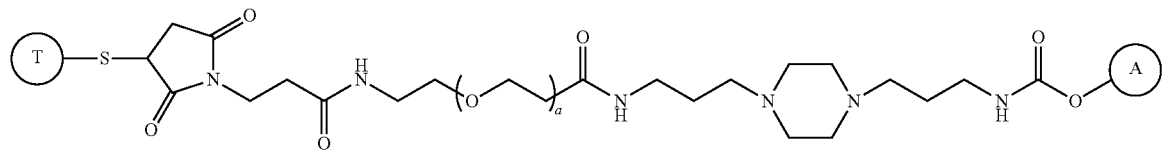

wherein

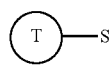

is the targeting moiety portion as described above,

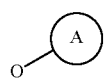

is the agent portion as described above, and a is as defined above with respect to the linker portion.

In some embodiments, the present disclosure provides an EDC of Formula (IV) wherein the agent is bufalin; the linker has a structure of Formula (II), wherein: $X_1$ is

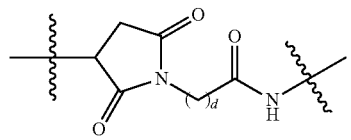

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —CH$_2$CH$_2$—, $R_3$ and $R_6$ are each —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is bufalin; the linker has a structure of Formula (II), wherein: $X_1$ is

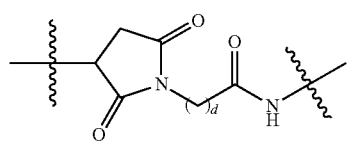

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —CH$_2$CH$_2$—, $R_3$ and $R_6$ are each —CH$_2$CH$_2$CH$_2$—; a is 36; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is bufalin; the linker has a structure of Formula (II), wherein: $X_1$ is

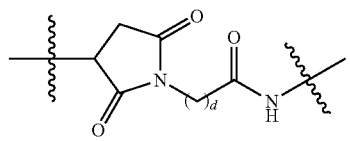

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —CH$_2$CH$_2$—, $R_3$ and $R_6$ are each —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is digitoxigenin; the linker has a structure of Formula (II), wherein: $X_1$ is

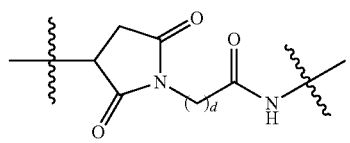

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —CH$_2$CH$_2$—, $R_3$ and $R_6$ are each —CH$_2$CH$_2$CH$_2$—; a is 36; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is digitoxigenin; the linker has a structure of Formula (II), wherein: $X_1$ is

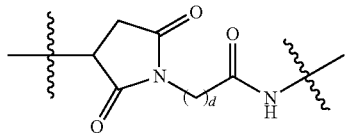

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —$CH_2CH_2R_3$ and $R_6$ are each —$CH_2CH_2CH_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

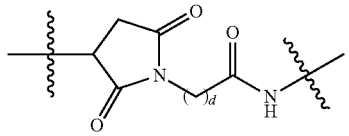

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —$CH_2CH_2$—, $R_3$ and $R_6$ are each —$CH_2CH_2CH_2$—; a is 36; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

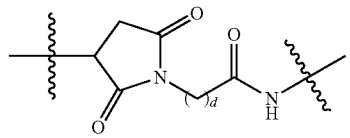

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —$CH_2CH_2$, $R_3$ and $R_6$ are each —$CH_2CH_2CH_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

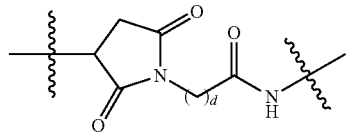

and d is 2; $X_2$ is —O—; $X_3$ is null; $X_4$ is —NH—; $X_5$ and $X_6$ are each N; $X_7$ is —NHC(O)—; $R_1$, $R_2$, $R_4$ and $R_5$ are each —$CH_2CH_2$, $R_3$ and $R_6$ are each —$CH_2CH_2CH_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is bufalin; the linker has a structure of Formula (II), wherein: $X_1$ is

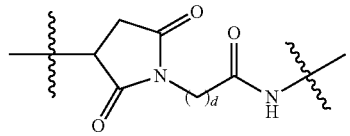

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is bufalin; the linker has a structure of Formula (II), wherein: $X_1$ is

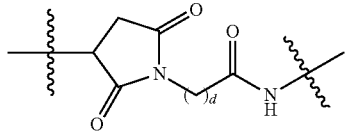

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 36; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

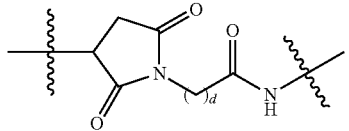

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

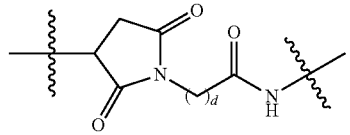

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 36; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is digitoxigenin; the linker has a structure of Formula (II), wherein: $X_1$ is

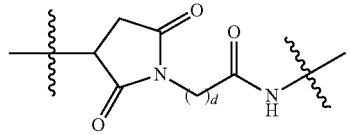

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is digitoxigenin; the linker has a structure of Formula (II), wherein: $X_1$ is

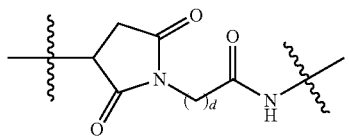

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 36; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is bufalin; the linker has a structure of Formula (II), wherein: $X_1$ is

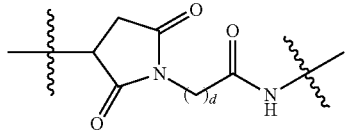

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is bufalin; the linker has a structure of Formula (II), wherein: $X_1$ is

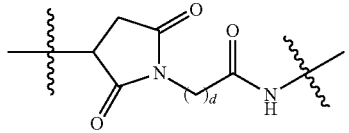

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

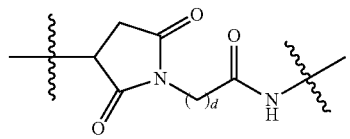

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is scillarenin; the linker has a structure of Formula (II), wherein: $X_1$ is

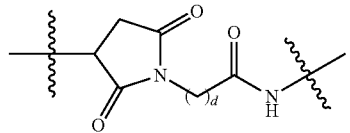

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is digitoxigenin; the linker has a structure of Formula (II), wherein: $X_1$ is

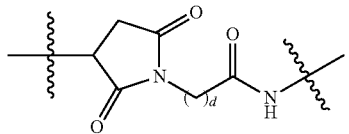

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

In some embodiments, the present disclosure provides an EDC of Formula (IV) wherein the agent is digitoxigenin; the linker has a structure of Formula (II), wherein: $X_1$ is

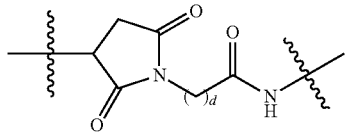

and d is 2; $X_2$ is —O—; $X_3$ is null; $X_4$ is —NH—; $X_5$ is —N(CH$_3$)—; $X_6$ is null; $X_7$ is —NHC(O)—; $R_1$ is —CH$_2$CH$_2$—; $R_2$ is —CH$_2$CH$_2$—; $R_3$ is —CH$_2$CH$_2$CH$_2$—; $R_4$ is null; $R_5$ and $R_6$, taken together, are —CH$_2$CH$_2$CH$_2$—; a is 24; b is 1; and c is 1; and the targeting moiety includes an antibody targeting moiety that binds a CD38 epitope selected from the group consisting of SUN4B7, HB7, OKT10, IB4, AT1, SAR650984, 38SB19, daratumumab, MOR202 antibodies and any binding fragment thereof. In some embodiments, the antibody targeting moiety is a human or chimeric SUN4B7 antibody or binding fragment thereof, or an antibody or binding fragment thereof that binds to the same or substantially similar CD38 epitope as SUNB47. In some embodiments, the targeting moiety is an AT1 antibody or binding fragment thereof, or an antibody or binding fragment thereof that binds to the same or substantially similar CD38 epitope as AT1.

An EDC of the present disclosure may be prepared step-wise by any of several routes, employing organic chemistry reactions, conditions, and reagents known to those skilled in the art, including: (1) reaction of the agent portion to a sub-unit of the linker including the heteroatom(s) such as nitrogen, followed by reaction of the terminal portion of the linker sub-unit to the remainder of the linker portion (e.g., to a polyethylene glycol) and finally reacting the targeting moiety to the terminal end of the linker to form the EDV; (2) reaction of the agent portion to a sub-unit of the linker including the heteroatom(s) such as nitrogen, reaction of the targeting moiety to the remaining portion of the linker portion, and finally coupling the terminal ends of the linker sub-units to form the EDC; (3) reaction of the targeting moiety with a sub-unit of the linker portion (e.g., a PEG polymer) followed by reaction of the terminal end of the linker sub-unit with the remaining sub-unit of the linker portion and finally reaction with the agent portion to form the EDC; (4) reaction of the sub-unit of the linker including the heteroatom(s) (e.g., nitrogen) with the PEG subunit to form the complete linker portion, followed by reaction of the completed linker portion with the agent portion to form an agent-linker sub-unit, and finally reaction of the agent-linker sub-unit with the targeting moiety to form the EDC; and/or (5) reaction of the sub-unit of the linker including the heteroatom(s) (e.g., nitrogen) with the PEG subunit to form the complete linker portion, followed by reaction of the completed linker portion with the targeting moiety portion to form an targeting moiety-linker sub-unit, and finally reaction of the targeting moiety-linker sub-unit with the agent portion to form the EDC.

Methods of coupling targeting moiety portion (e.g., antibodies) to a PEG-type linker sub-unit are known to those skilled in the art and can be found, for example, in the Examples that follow and in WO 2012/178173, the contents of which are incorporated herein by reference in their entirety.

In one embodiment, an EDC of the present disclosure is formed by reacting an activated form of the agent portion (e.g., a steroid-type agent having a 4-nitrophenyl carbamate group bound to the 3-hydroxyl oxygen atom) with an alkylamine sub-unit of the linker, followed by coupling with a protected PEG polymer (e.g., MAL-PEG24-TFP ester, product no. 10554, Quanta Biodesign Ltd, Plain City, Ohio, USA) to form the agent-(protected)linker (e.g., MAL-PEG24-alkylamine-agent). The agent-(protected)linker is then conjugated with the targeting moiety (e.g., with an antibody such as a murine, a human, chimeric, or humanized anti-CD38 antibody or binding fragment thereof such as SUN4B7, optionally reduced by reaction with a reducing agent such as tris(2-carboxyethyl)phosphine), to form the EDC through nucleophilic addition to the maleimide portion of the agent-(protected)linker.

Nucleophilic groups on antibodies and other targeting moieties for example include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. In addition, the disulfide bridge can be crosslinked by the linker portion of the EDC of the present disclosure such that the linker-agent is covalently attached to the antibody while maintaining a closed linked between the two cysteines thus stabilizing the antibody (WO 2013/085925A1 and Bioconjugate Chem., Vol. 1, No. 1, 1990 pp 36-50). Additional nucleophilic groups can be introduced into antibodies through the reaction of lysines with 2-iminothiolane (Traut's reagent) resulting in conversion of an amine into a thiol.

EDC may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Certain targeting moieties, such as antibodies, may include more than one site reactive to the linker portion of the agent-linker sub-unit. In such embodiments, more than one agent may be bound to a single targeting moiety. Agent loading refers to the average number of agents per targeting moiety (e.g., antibody) in a EDC. Where each linker is linked to one agent, the average number of agents will equal the average number of linkers on the targeting moiety. Agent loading for EDCs of the present disclosure typically ranges from 1 to 8 agents per targeting moiety, if the targeting moiety is an antibody (Ab), e.g. where 1, 2, 3, 4, 5, 6, 7, or 8 therapeutic agents are covalently attached to the antibody. Thus, compositions of EDCs include collections of antibodies conjugated with a range of drugs, from 1 to 8. The average number of drugs per antibody in preparations of EDC from conjugation reactions may be characterized by conventional means such as mass spectroscopy, ELISA assay, electrophoresis, and HPLC. By ELISA, the averaged value of therapeutic agents in a particular preparation of EDC may be determined (Hamblen et al (2004) *Clinical Cancer Res.* 10:7063-7070; Sanderson et al (2005) *Clinical Cancer Res.* 11:843-852). However, it is not possible to identify the location of therapeutic agents and/or linkers conjugated to antibodies by ELISA based methods. In some instances, separation, purification, and characterization of homogeneous EDC (where the number of therapeutic agents is the same but the location on the antibody may be different) may be achieved by means such as reverse phase HPLC or electrophoresis.

In some embodiments, the EDC consisting of an agent portion, a linker portion and a targeting moiety portion is purified away from uncoupled agent, linker and/or targeting moiety using standard affinity, size exclusion, filtration, or other methods known to one skilled in the art.

In various embodiments, the EDC of the present disclosure are generally useful for the treatment of cancer, immune disorders (e.g., asthma), and other diseases. Examples of diseases for cancer treatment include breast cancer, colorectal cancer, liver cancer, lung cancer, prostate cancer, ovarian cancer, brain cancer, and pancreatic cancer. Specifically, treatment for one of the following tumor types can be effected: B-cell lymphoblastic leukemia, T-cell lymphoblastic leukemia, lymphoma, including Hodgkin's lymphoma and non-Hodgkin's lymphoma, follicular lymphoma, Burkitt lymphoma, melanoma, ocular melanoma, cutaneous melanoma, colon adenocarcinomas, hepatocellular carcinomas, renal cell carcinoma, ovarian carcinoma, prostate adenocarcinoma, liver carcinoma, transitional cell carcinoma, pancreatic adenocarcinoma, lung carcinoma, breast carcinoma, and colon carcinoma.

VII. Pharmaceutical Formulations

The administration of the compounds or formulations according to the present disclosure (e.g., compounds or formulations comprising the disclosed EDC) can be done by any of the administration methods accepted for the therapeutic agents and generally known in the art. These processes include, but are not limited to, systemic administration, for example by parenteral, oral, nasal, or topical administration (e.g., by patch). Parenteral administration is done generally by subcutaneous, intramuscular or intravenous injection, or by perfusion. In general, antibody based therapeutics are typically administered intravenously. The injectable compositions can be prepared in standard forms, either in suspension or liquid solution or in solid form that is suitable for an extemporaneous dissolution in a liquid. In one embodiment, parenteral administration uses the installation of a system with slow release or extended release that ensures the maintenance of a constant dose level. For intranasal administration, it is possible to use suitable intranasal vehicles that are well known to those skilled in the art. The oral administration can be done by means of tablets, capsules, soft capsules (including formulations with delayed release or extended release), pills, powders, granules, elixirs, dyes, suspensions, syrups and emulsions. This form of presentation is more particularly suited for the passage of the intestinal barrier.

The dosage for the administration of compounds or formulations according to the present disclosure is selected according to a variety of factors including the type, strain, age, weight, sex and medical condition of the subject; the severity of the condition to be treated; the method of administration; the condition of the renal and hepatic functions of the subject and the nature of the particular compound or salt that is used and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations. For example, a normally experienced doctor will easily determine and prescribe the effective amount of the desired compound to prevent, disrupt or stop the progress of the medical condition that is to be treated. By way of examples, when given parenterally, the effective levels of the compounds according to the present disclosure will be in the range of from about 0.002 to about 500 mg per kg of body weight, more particularly from about 0.02 mg to about 50 mg per kg of body weight and administered daily, weekly, or biweekly.

The compounds or formulations according to the present disclosure can be administered in the form of single daily doses, or the total daily dosage can be administered in doses (e.g., divided doses) of two, three, four or more doses per day. Such dose(s) may be administered intermittently, e.g. every week or every three weeks (e.g. such that the patient receives from about two to about twenty, e.g. about six doses, of the composition or formulation). An initial higher loading dose, followed by one or more lower doses, may be administered. An exemplary dosing regimen comprises administering an initial loading dose followed by a weekly maintenance dose. However, other dosage regimens may be useful. More specifically, the dosage can in some embodiments be similar in the range of 1-20 mgs/meter squared (mgs/m$^2$) body surface area (bsa), and the doses can be administered weekly or every two weeks. For solid tumors the dosage may in some embodiments be higher, e.g., an initial dose in the range of 200 to 600 mgs/m$^2$ bsa or ~0.01 to 20 mgs/kg (given, e.g., through a 120-minute intravenous infusion) and 150-350 mgs/m$^2$ or 1-10 mgs/kg (given through 60-minute intravenous infusion). Therefore the dosing range of the compounds according to the present disclosure can be daily to weekly dosages of 1 mgs/m$^2$ to 500 mgs/m$^2$ bsa.

The compositions or formulations according to the present disclosure can be sterilized and/or can contain one or more of: non-toxic adjuvants and auxiliary substances such as agents for preservation, stabilization, wetting or emulsification; agents that promote dissolution; and salts to regulate osmotic pressure and/or buffers. In addition, they can also contain other substances that offer a therapeutic advantage. The compositions are prepared, respectively, by standard processes of mixing, granulation or coating well known to those skilled in the art.

The compounds or formulations of the present disclosure herein can be administered concurrently, sequentially, or alternating with the second drug or upon non-responsiveness with other therapy. Thus, the combined administration of a second drug includes coadministration, using separate formulations or a single pharmaceutical formulation, and consecutive administration in either order, wherein preferably there is a time period while both (or all) therapies simultaneously exert their biological activities. Multiple second drugs may be used in combination the compounds of the present disclosure.

In another embodiment of the present disclosure, articles of manufacture containing materials useful for the treatment of the disorders described above are provided. In one aspect, the article of manufacture comprises (a) a container comprising the compounds or formulations herein (preferably the container comprises the EDC and a pharmaceutically acceptable carrier or diluent within the container); and (b) a package insert with instructions for treating the disorder in a patient.

Therapeutic EDC of the present disclosure may be administered by any route appropriate to the condition to be treated. The EDC will typically be administered parenterally, e.g. infusion, subcutaneous, intramuscular, intravenous, intradermal, intrathecal, bolus, intratumor injection or epidural (Shire et al (2004) J. Pharm. Sciences 93(6):1390-1402). Pharmaceutical formulations of EDC are typically prepared for parenteral administration with a pharmaceutically acceptable parenteral vehicle and in a unit dosage injectable form. An EDC having the desired degree of purity is optionally mixed with pharmaceutically acceptable diluents, carriers, excipients or stabilizers, in the form of a lyophilized formulation or an aqueous solution (Remington's Pharmaceutical Sciences (1980) 16th edition, Osol, A. Ed.).

Acceptable parenteral vehicles, diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference. An exemplary formulation of an EDC contains about 100 mg/ml of trehalose (2-(hydroxymethyl)-6-[3,4,5-trihydroxy-6-(hydroxymethyl)tetrahydropyran-2-yl]oxy-tetrahydropyran-3,4,5-triol; $C_{12}H_{22}O_{11}$; CAS Number 99-20-7) and about 0.1% TWEEN™ 20 (polysorbate 20; dodecanoic acid 2-[2-[3,4-bis(2-hydroxyethoxy)tetrahydrofuran-2-yl]-2-(2-hydroxyethoxy)et-hoxy]ethyl ester; $C_{26}H_{50}O_{10}$; CAS Number 9005-64-5) at approximately pH 6.

Pharmaceutical formulations of a therapeutic EDC may contain certain amounts of unreacted agent portion, targeting moiety-linker intermediate, and/or agent-linker intermediate, as a consequence of incomplete purification and separation of excess reagents, impurities, and by-products, in the process of making the EDC; or time/temperature hydrolysis or degradation upon storage of the bulk EDC or formulated EDC composition. For example, it may contain a detectable amount of agent-linker or various intermediates. Alternatively, or in addition to, it may contain a detectable amount of the un-linked free targeting moiety. An exemplary formulation may contain up to 10% molar equivalent of the agent of agent-linker as it was determined by the in vitro cellular proliferation assays that in some cases the agent-linker conjugate less potent in cell killing than free agent.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the EDC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions contain the active materials (EDC) in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of EDC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 µg of the active ingredient per milliliter of solution in order that infusion of a suitable volume at a rate of about 30 mL/hr can occur. Subcutaneous (bolus) administration may be effected with about 1.5 ml or less of total volume and a concentration of about 100 mg EDC per ml. For EDC that require frequent and chronic administration, the subcutaneous route may be employed, such as by pre-filled syringe or autoinjector device technology.

As a general proposition, the initial pharmaceutically effective amount of EDC administered per dose will be in the range of about 0.01-100 mg/kg, namely about 0.1 to 20 mg/kg of patient body weight per day, with the typical initial range of compound used being 0.3 to 15 mg/kg/day. For example, human patients may be initially dosed at about 1.0 mg EDC per kg patient body weight. The dose may be escalated to the maximally tolerated dose (MTD). The dosing schedule may be about every 3 weeks, but according to diagnosed condition or response, the schedule may be more or less frequent. The dose may be further adjusted during the course of treatment to be at or below MTD which can be safely administered for multiple cycles, such as about 4 or more.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are generally disfavored due to poor bioavailability due to limited absorption, hydrolysis or denaturation in the gut, formulations of EDC suitable for oral administration may be prepared as discrete units such as capsules, cachets or tablets each containing a predetermined amount of the EDC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

The present disclosure further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The EDCs of the present disclosure may be used to treat various diseases or disorders, such as cancer and autoimmune conditions or other immune disorders in human or animal subjects. In one embodiment, the subject is a human. In another embodiment, the subject is a non-human animal (e.g dog, cat, horse, bird, etc.). Exemplary conditions or disorders include benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders, including but not limited to asthma.

The EDC compounds which are identified in the animal models and cell-based assays can be further tested in tumor-bearing higher primates and human clinical trials. Human clinical trials can be designed similar to the clinical trials testing efficacy. The clinical trial may be designed to evaluate the efficacy of an EDC in combination with known therapeutic regimens, such as radiation and/or chemotherapy involving known chemotherapeutic and/or cytotoxic agents (Pegram et al (1999) Oncogene 18:2241-2251). In one embodiment, the combination therapeutic agent is selected from ATRA, Velcade, Arsenic trioxide, Thalidomide, Buclasine, ABT-199, Geldanamycin, mTOR inhibitors, Butyrate, (MG132, velcade, other (proteasome inhibitors), Anisomycin, D-cAMP, Berberine, Calciferol or other vitamin D derivatives, Bafilomycin A1, (Rocaglamide or other flavaglines), Bevacizumab; Carboplatin; Cisplatin; Cyclophosphamide; Docetaxel injection; Doxorubicin; Etoposide; Etoposide Phosphate; Gemzar (gemcitabine HCL); Hycamtin (topotecan hydrochloride); Ifosfamide; Iressa (gefitinib); Irinotecan injection; Methotrexate injection; Mitomycin; Paclitaxel; Photofrin, QLT; Premetrexed; Procarbazine; Streptozocin; Tarceva (erlotinib); Vinblasine; Vincristine; and Vinorelbine tartrate.

Examples of cancer to be treated using EDCs of the present disclosure include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the appropriate dosage of an EDC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g., 0.1-20 mg/kg including, for example, 1 mg/kg to 15 mg/kg) of molecule is an initial candidate dosage for administration to the patient, whether, for example, by one or more separate administrations, or by continuous infusion. A typical daily dosage might range from about 1 µg/kg to 100 mg/kg (e.g., 1 mg/kg to 100 mg/kg) or more, depending on the factors mentioned above. An exemplary dosage of EDC to be administered to a patient is in the range of about 0.1 to about 10 mg/kg of patient weight.

An EDC of the present disclosure may be combined in a pharmaceutical combination formulation, or dosing regimen as combination therapy, with a second compound having anti-cancer properties. The second compound of the pharmaceutical combination formulation or dosing regimen preferably has complementary activities to the EDC of the combination such that they do not adversely affect each other.

The second compound may be a chemotherapeutic agent, cytotoxic agent, cytokine, growth inhibitory agent, anti-hormonal agent, aromatase inhibitor, protein kinase inhibitor, lipid kinase inhibitor, anti-androgen, antisense oligonucleotide, ribozyme, gene therapy vaccine, anti-angiogenic agent and/or cardioprotectant. Such molecules are suitably present in combination in amounts that are effective for the purpose intended. A pharmaceutical composition containing an EDC may also have a therapeutically effective amount of a chemotherapeutic agent such as a tubulin-forming inhibitor, a topoisomerase inhibitor, or a DNA binder.

Other therapeutic regimens may be combined with the administration of an anticancer agent identified in accordance with this present disclosure. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

In one embodiment, treatment with an EDC of the present disclosure involves the combined administration of an anti-cancer agent identified herein, and one or more chemotherapeutic agents or growth inhibitory agents, including coadministration of cocktails of different chemotherapeutic agents. Chemotherapeutic agents include taxanes (such as paclitaxel and doxetaxel) and/or anthracycline antibiotics. Preparation and dosing schedules for such chemotherapeutic agents may be used according to manufacturers's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The anticancer agent may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide an effect achieved when the active ingredients used together is greater than the sum of the effects that results from using the compounds separately. The effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, an effect may be attained when the compounds are administered or delivered sequentially, e.g.

by different injections in separate syringes. In general, during alternation therapy, an effective dosage of each active ingredient is administered sequentially, e.g. serially, whereas in combination therapy, effective dosages of two or more active ingredients are administered together.

Also falling within the scope of this disclosure are the in vivo metabolic products of the EDC compounds described herein, to the extent such products are novel and unobvious over the prior art. Such products may result for example from the oxidation, reduction, hydrolysis, amidation, esterification, enzymatic cleavage, and the like, of the administered compound. Accordingly, the present disclosure includes novel and unobvious compounds produced by a process comprising contacting a compound of this present disclosure with a mammal for a period of time sufficient to yield a metabolic product thereof.

Metabolite products may be identified by preparing a radiolabelled EDC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the EDC compounds.

Metabolites include the products of in vivo cleavage of the EDC where cleavage of any bond occurs that links the drug moiety to the antibody. Metabolic cleavage may thus result in the naked antibody, or an antibody fragment. The antibody metabolite may be linked to a part, or all, of the linker. Metabolic cleavage may also result in the production a drug moiety or part thereof. The drug moiety metabolite may be linked to a part, or all, of the linker.

In another embodiment, an article of manufacture, or "kit", containing EDC and materials useful for the treatment of the disorders described above is provided. The article of manufacture comprises a container and a label or package insert on or associated with the container. Suitable containers include, for example, bottles, vials, syringes, or blister pack. The containers may be formed from a variety of materials such as glass or plastic. The container holds an EDC composition which is effective for treating the condition and may have a sterile access port (for example the container may be an intravenous solution bag or a vial having a stopper pierceable by a hypodermic injection needle). At least one active agent in the composition is an EDC. The label or package insert indicates that the composition is used for treating the condition of choice, such as cancer. For example, the cancer may be one which overexpresses one of the targets of the EDC of the present disclosure. The label or package insert may also indicate that the composition can be used to treat cancer, wherein the cancer is not characterized by overexpression of one of the targets of the EDC of the present disclosure. In other embodiments, the package insert may indicate that the EDC composition can be used also to treat hormone independent cancer, prostate cancer, colon cancer or colorectal cancer.

The article of manufacture may comprise a container with a compound contained therein, wherein the compound comprises an EDC of the present disclosure. The article of manufacture in this embodiment may further comprise a package insert indicating that the EDC can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1

Synthesis of Linker-Ready Therapeutic Agents, Preparation of EDCs, and Assessment of Biological Activity This example describes the synthesis of the "linker-ready" agent CEN010-105 in its thiol reactive form (Part A) and the conjugation of the steroid scillarenin to antibodies to form various EDCs of the present disclosure (Part B). This example also describes various methods that can be used to assess EDC activity (Part C).

Part A Synthesis of "Linker-Ready" Agent

This example describes a synthetic protocol for attaching a steroid drug to a linker to produce a "linker-ready" agent that can be readily attached to an antibody, as described herein. By linking the amino acid cysteine to the thiol reactive form of the "linker-ready" agent, the capped "linker-ready" agent can also be used to investigate activity of a potential EDC breakdown product, as may be generated by EDC degradation by proteases in vivo.

CEN010-105 is a "linker-ready" scillarenin that comprises scillarenin, a linker and an active group used to form a covalent stable attachment to the antibody. The general synthetic steps for the preparation of CEN010-105 are as follows.

2,3-di-O-benzoyl-4-azido-4-deoxy-L-xylopyranoside-1-trichloroacetimidate

1-Allyl-2,3-di-O-benzoyl-4-azido-4-deoxy-L-ribopyranoside (11.9 g, 28.1 mmol) was dissolved in dichloromethane/methanol (80 mL, 90:10) under argon, and PdCl$_2$ (0.5 g, 2.8 mmol) was added to the solution. The mixture was stirred overnight at room temperature, filtered through a pad of Celite and concentrated under reduced pressure. The residue was filtered through a pad of silica gel (hexane/EtOAc, 70:30). The resulting compound (8.38 g, 21.83 mmol) was dissolved in dry dichloromethane (170 mL) under argon. CCl$_3$CN (21.9 mL, 218.3 mmol) was added, followed by dropwise addition of DBU (1.63 mL, 10.91 mmol) at 0° C. The reaction was stirred for 1 h at 0° C. The solvent was removed under reduced pressure. The crude product was filtered through a pad of silica gel (hexane/EtOAc, 60:40 to 40:60) to afford 2,3-di-O-benzoyl-4-azido-4-deoxy-L-ribopyranoside-1-trichloroacetimidate as a yellow oil (9.7 g, 65%). The compound was carried forward without further purification. R$_f$ 0.37 (silica gel, hexane/EtOAc, 80:20).

Scillarenin-2,3-di-O-benzoyl-4-azido-4-deoxy-L-xylopyranoside 2,3-di-O-benzoyl-4-azido-4-deoxy-L-xylopyranoside-1-trichloroacetimidate (0.483 g, 0.915 mmol) was added to a suspension of activated 4 Å molecular sieves (90 mg) in dry dichloromethane (15 mL) under argon at 0° C. Scillarenin (0.182 g, 0.474 mmol) was then added to the mixture. After 5 minutes, Zn(OTf)$_2$ (17 mg, 0.047 mmol) was added and the reaction mixture was stirred for an additional 30 minutes at 0° C. An additional amount of scillarenin (0.182 g, 0.474 mmol) was added. The reaction mixture was stirred for 30 minutes at 0° C. The reaction was quenched with few drops of Et$_3$N. The mixture was filtered and the solvent was removed under reduced pressure. The crude product was purified by flash chromatography (hexane/EtOAc, 75:25 to 50:50) to afford scillarenin-2,3-di-O-benzoyl-4-azido-4-deoxy-L-xylopyranoside as a white powder (0.521 g, 76%) R$_f$ 0.35 (silica gel, hexane/EtOAc, 50:50). $^1$H-NMR (300 MHz, CDCl$_3$) δ, 0.68 (s, 3H), 0.90-2.17 (m, 21H), 2.39-2.44 (m, 1H), 3.47 (dd, 1H, J=12.0, 9.5 Hz, H-5b), 3.79-3.87 (m, 1H, H-4), 4.17-4.22 (m, 2H, H-5a), 4.78 (d, 1H, J=6.8 Hz, H-1), 5.26 (dd, 1H, J=8.6, 6.8 Hz, H-2), 5.33 (s, 1H), 5.49 (dd, 1H, J=8.7 Hz, H-3), 6.22 (dd, 1H, J=9.7, 0.6 Hz), 7.18-7.19 (m, 1H), 7.33-7.39 (m, 4H), 7.47-7.53 (m, 2H), 7.80 (dd, 1H, J=9.7, 2.6 Hz), 7.92-7.97 (m, 4H); $^{13}$C-NMR (75 MHz, CDCl$_3$) δ 16.7, 19.0, 21.4, 25.8, 28.7, 28.8, 32.4, 32.8, 35.2, 37.6, 40.8, 42.9, 48.4, 50.2, 51.2, 59.2, 63.1, 71.6, 72.9, 76.1, 85.2, 100.0, 115.5, 121.7, 122.8, 128.5, 128.6, 129.1, 129.5, 129.9, 130.1, 133.4, 133.6, 146.9, 147.6, 148.7, 162.5, 165.3, 165.7.

Scillarenin-4-azido-4-deoxy-L-xylopyranoside

Scillarenin-2,3-di-O-benzoyl-4-azido-4-deoxy-L-xylopyranoside (0.351 g, 0.468 mmol) was dissolved in methanol (21 mL). Et$_3$N (7 mL) and H$_2$O (7 mL) were added. The reaction mixture was stirred for 2 days at room temperature. The mixture was filtered and the solvent was stripped under reduced pressure. The crude product was purified by flash chromatography (CH$_2$Cl$_2$/MeOH, 98:2 to 95:5) to afford scillarenin-4-azido-4-deoxy-L-xylopyranoside as a yellow powder (40 mg, 24%) R$_f$ 0.31 (CH$_2$Cl$_2$/MeOH, 95:5); $^1$H-NMR (300 MHz, CD$_3$OD) δ, 0.74 (s, 3H), 1.03-2.21 (m, 21H), 2.52-2.57 (m, 1H), 3.12-3.20 (m, 2H), 3.40-3.44 (m, 2H), 3.87-3.92 (m, 1H), 4.17-4.23 (m, 1H), 4.31 (d, 1H, J=7.7 Hz, H-1), 5.35 (s, 1H), 6.28 (dd, 1H, J=9.7, 0.8 Hz), 7.43 (d, 1H, J=1.5 Hz), 7.99 (dd, 1H, J=9.7, 2.6 Hz).

Scillarenin-4-amino-4-deoxy-L-xylopyranoside

Scillarenin-4-azido-4-deoxy-L-xylopyranoside (1.61 g, 2.34 mmol) was dissolved in THF/H$_2$O (2.8 mL, 90:10). PPh$_3$ polymer-bound (79 mg, 3 mmol·g$^{-1}$) was added. The reaction mixture was stirred for 2 hours at 40° C. The mixture was then filtered and the solvent was removed under reduced pressure. The crude product was purified by flash chromatography (CH$_2$Cl$_2$/MeOH, 90:10 to 80:20) to afford scillarenin-4-amino-4-deoxy-L-xylopyranoside as a yellow powder (23 mg, 58%) R$_f$ 0.2 (CH$_2$Cl$_2$/MeOH, 80:20). $^1$H-NMR (300 MHz, CD$_3$OD) δ, 0.74 (s, 3H), 1.06-2.19 (m, 21H), 2.52-2.57 (m, 1H), 2.75-2.86 (m, 1H, H-4), 3.14-3.24 (m, 2H, H-2, H-3), 3.64-3.72 (m, 1H, H-5b), 3.87-3.91 (m, 1H, H-5a), 4.19-4.24 (m, 1H), 4.36 (d, 1H, J=7.1 Hz, H-1), 5.38 (s, 1H), 6.28 (dd, 1H, J=9.7, 0.6 Hz), 7.42 (d, 1H, J=1.6 Hz), 7.99 (dd, 1H, J=9.7, 2.5 Hz); $^{13}$C-NMR (75 MHz, CD$_3$OD) δ 17.4, 19.6, 22.5, 26.8, 29.9, 30.1, 33.3, 33.6, 36.6, 38.8, 41.8, 43.5, 49.4, 51.7, 52.2, 75.3, 76.5, 78.9, 79.3, 79.8, 85.8, 103.7, 115.6, 123.4, 125.1, 148.4, 149.4, 150.5, 164.9.

CEN010-105.

To a solution of Scillarenin-4-amino-4-deoxy-L-xylopyranoside (18.5 mg, 0.0359 mmol) in DMF (1 mL) at room temperature was added NHS-PEG$_{24}$-Maleimide (50 mg, 0.0359 mmol). Then Et$_3$N (0.025 mL, 0.18 mmol) was added. The reaction was stirred at room temperature for 2 hours. The solvent was removed under reduced pressure. The crude material was purified by flash chromatography (CH$_2$Cl$_2$/MeOH, 95:5 to 80:20) to afford CEN010-105 as a yellow oil (48 mg, 75%) R$_f$ 0.66 (CH$_2$Cl$_2$/MeOH, 80:20). HPLC analysis [Luna C18, 250×4.60 mm, 5 μm, 5% to 95% ACN over 32 minutes, 1 ml·min$^{-1}$] indicated a product which was >95% pure. HRMS-ESI (m/z): calculated for C$_{87}$H$_{147}$N$_3$O$_{35}$ [M+K$^+$]$^+$: 1832.9452. found 1832.9777.

Part B Preparation of Immunoconjugates (EDCs and Control)

The EDCs described in Examples 2 through 10 and a control conjugate (contains antibody 4F12, a mouse IgG kappa, which does not bind cell human cells) were prepared by the following method, involving reduction of antibody interchain disulfides. Briefly, antibody at concentrations between 1-10 mg/ml in PBS (20 mM sodium phosphate pH 7 and 150 mM NaCl) were reduced in the presence of 1 mM diethylenetriamine pentaacetic acid (DTPA) (MP Biomedical LLC) and 8 molar equivalents of tris(2-carboxyethyl) phosphine (TCEP) (cat. number: HR2-651, Hampton Research) at 37° C. for 2 hours then transferred to wet ice. Then 9.6 equivalents of CEN010-105 ("linker-ready" agent) were added and allowed to react for 30 min on ice. The reaction was quenched by the addition of 1.5 equivalents of L-cysteine over CEN010-105 and allowed to react 30 minutes at RT. The antibody conjugates were then separated from unconjugated CEN010-105 by repeated centrifugal concentration using Amicon Ultra 30,000 MWCO (Millipore, Billerica, Mass.) and DPBS buffer exchange. The conjugates were stored at 2-8° C. in PBS at concentrations ranging from 1-10 mg/ml.

Agent loading for EDCs (number of agents per antibody) with scillarenin as the agent is determined by the following method. Once the extinction coefficient of the agent is determined at a wavelength outside ±10 nm of 280 nm, this method can be used for any EDC comprising a steroid drug. The method entails measuring absorbance of the conjugates, the antibodies (Ab) and scillarenin (drug) at both 280 nm and, in the case of scillarenin, 299 nm. First, the absorbance of free antibody is measured at both 280 nm (A$_{280}$Ab) and 299 nm (A$_{299}$Ab) to determine antibody constant [Constant Ab]. Next, the absorbance of free drug is measured at both 280 nm (A$_{280}$drug) and 299 nm (A$_{299}$drug) to determine drug constant [Constant Drug]. Finally, the absorbance of antibody drug conjugate is measured [A$_{280}$Conj and A$_{299}$Conj]. The antibody molar extinction coefficient at 280 nm=204,000 M$^{-1}$cm$^{-1}$.

Part C Cytotoxic Activity Assessment

Cells and culture conditions: Cell lines H460, HT29, A549, PANC-1, MB231, FaDu, H69 and H929 were obtained from the American Type Culture Collection (ATCC), Manassas, Va. The malignant melanoma cell line LOX IMVI was obtained from the DCTD Tumor Repository, National Cancer Institute, Frederick, Md., The cell lines were maintained in the recommended media formulations and subcultured every 3 to 4 days. To activate expression of certain targets to which the drug moiety bind and/or to form Na,K-ATPase complexes with certain proteins, cells can be cultured in recommended media plus additives such as phorbol esters, various growth factors and cytokines such as VEGF, fibroblast growth factors, human growth factors, interleukins, and tumor necrosis factors. In addition, cells can be cocultured with other cells like human fibroblasts. Additionally, microtiter plates can be coated with various proteins like fibrinogen.

In vitro cytotoxicity assessment: Cells were plated at a density between 1250 and 3333 per well of a 384-well white tissue culture treated microtiter plate in 20 ul complete media, then grown for 24 hour at 37° C. with 7% $CO_2$ in a humidified incubator before conjugate or small molecule agent addition. Cells were incubated in the presence of test compound for 72 hr prior to cell viability testing. Cell viability testing was performed using the CellTiter-Glo luminescent cell viability assay (Promega, Madison, Wis.). EC50 values of the test compounds for each cell line were determined using GraphPad Prism 5 software.

Example 2

Synthesis of Various Agents and Agent-Linker Intermediates i. 4-Nitrophenyl carbamate-3-O-bufalin Synthesis 36.08 (93.3 μmol) of bufalin was weighed and dissolved in 2 mL of DCE. 38 μL (467 μmol) of pyridine and 57.5 mgs (285.3 μmol) of 4-nitrophenyl chloroformate was added to the bufalin and stirred overnight (~16 hours). TLC showed the reaction was ~50% complete. An additional 38 μL (467 μmol) of pyridine and 68.5 mgs (340 μmol) of 4-nitrophenyl chloroformate was added along with 4 Å Molecular Sieves. The reaction was stirred for 30 minutes at room temperature. 2 mL of Glacial Acetic Acid was added to 198 mL of nanopure water to create a 1% Acetic Acid solution. 60-70 mL of DCM was added to the reaction and was poured into a separatory funnel. An extraction was performed by adding 50 mL of the 1% acetic acid solution to the separatory funnel. This was repeated 3 more times. The aqueous layer was then discarded. 1.4 g (11.63 mmol) of MgSO4 was added to the organic layer. The mixture was stirred for 20 minutes and gravity filtered, followed by rotary evaporation of the solvent. The material was dissolved in a minimal amount of DCM and a flash column was run using silica gel (Pore Size=0.015-0.040 μm). The appropriate fractions were collected and the solvent was evaporated off 41.34 mgs (74.67 μmol) of product was obtained corresponding to an 80.03% yield. TLC: 75:25 DCM:EtOAc; Rf2=0.46; $^1$H-NMR (400 MHz, DMSO-d6): δ 8.3 (d, 2H, H23, 24), 7.92 (s, 1H, H21), 7.56 (d, 2H, H22,25), 7.51 (s, 1H, H14), 6.28 (d, 1H, H20), 4.17 (s, 1H, H10), 4.13 (s, 1H, H13), 3.87 (s, 1H, H3), 2.1-1.1 (multiple peaks, 22H, H1,2,4,5,6,7,8,9,11,1215,16,17), 0.89 (s, 3H, H18), 0.59 (s, 3H, H19). IUPAC Name: Unknown ii. 4-Nitrophenyl carbamate-3-O-Digitoxigenin Synthesis 695.5 mgs (3.45 mmol) of 4-nitrophenyl chloroformate containing 2.914 g of 4 Å Molecular Sieves was dissolved in 12 mL of DCE. 2.914 g of 4 Å Molecular Sieves and 461.2 μL (5.702 mmol) of pyridine was added to the reaction. 211.85 mgs (570.2 umol) of digitoxigenin (3) was then added to the reaction and allowed to stir overnight (~16 hours). The solvent was decanted, placed in a round bottom flask and rotary evaporated off. The remaining solid was resuspended in DCM (12 mL) and placed on a flash column (75:25 DCM:EtOAc; pore size=0.015-0.040 μm). The purified fractions were combined and the solvent was rotary evaporated off 272 mgs (505 μmol) of 4-nitrophenyl carbamate-3-O-digitoxigenin was obtained for a % Yield of 88.56%. TLC: 75:25 DCM:EtOAc; Rf4=0.57. HPLC Analysis: C18 Column: Atlantis®T3; 3 um; 4.6×150 mm; Gradient: 0-2 min=90:20 (A:B); 1-16 min=0:100 (A:B); 16-25 min=0:100 (A:B); Flow Rate: 1 mL/min; Rt4=21.22 min (λmax=271 nm). IUPAC Name: Unknown iii. CEN-371 Synthesis 10 mgs (18.1 μmol) of 4-nitrophenyl carbamate-3-O-bufalin was reacted with 200 μL (971.5 μmol) of 1,4-Bis(3-aminopropyl)piperazine by stirring at room temperature for 35 minutes. The material was purified by reverse-phase HPLC (Buffer A=1% Acetic Acid in $H_2O$; Buffer B=1% Acetic Acid in ACN). The solvent of the collected material was rotary evaporated off. The material was frozen and lyophilized overnight. 4.87 mgs (7.95 μmol) of CEN-371 was obtained for a % Yield of 43.9%. TLC: 75:25 DCM:EtOAc; RfCEN-371=0.0; Ninhydrin positive; HPLC Analysis: C18 Column: Atlantis®T3; 3 um; 4.6×150 mm; Gradient: 0-1 min=80:20 (A:B); 1-19 min=10:90 (A:B); Flow Rate: 1 mL/min; RtCEN-371=9.27 min (λmax=300 nm). $^1$H-NMR (400 MHz, DMSO-d6): δ 7.92 (d, 1H, H21), 7.52 (s, 1H, H14), 7.03 (s, 1H, H26), 6.28 (d, 1H, H20), 4.78 (s, 1H, H3), 4.13 (s, 1H, H13), 3-1.1 (multiple peaks, 44H, H1,2,4-9,11,12,15-17,27-37), 0.89 (s, 3H, H18), 0.59 (s, 3H, H19). $^{13}$C NMR (500 MHz, CDCl$_3$): δ 177.02, 162.37, 156.28, 148.51, 146.8, 122.67, 115.25, 85.26, 70.11, 57.46, 56.43, 52.8, 52.59, 51.20, 48.32, 42.29, 40.82, 40.40, 35.78, 35.15, 32.75, 30.73, 30.54, 28.70, 26.43, 25.81, 25.34, 23.83, 23.28, 22.93, 21.39, 21.29, 16.52. TOF-MS (ESI): MWobs=613.44 g/mol; MWcalc.=613.84 g/mol. IUPAC Name: 4-(3-{(1 S,2S,5S,7R,10R,11S,14S,15R)-11-Hydroxy-2,5,14,15-tetramethyl-14-(6-oxo-3-pyranyl)tetracyclo[8.7.0.02,7.011,15]heptadec-5-yloxycarbonylamino}propyl)-1-(3-aminopropyl)piperazine.

iv. CEN-372 Synthesis 31.8 mgs (57.44 μmol) of 4-nitrophenyl carbamate-3-O-bufalin was dissolved in 1 mL of DCM and 1 mL of MTBE. 46.3 μL (287.2 μmol) of 3,3'-diamino-N-methyldipropylamine was added and stirred at room temperature. After 90 minutes 4 mL of MTBE was added and stirred for an additional 30 minutes. The solvent was decanted off, leaving a yellow precipitate behind. The precipitate was washed with a minimal amount of MTBE. The MTBE was decanted off and placed with the previously decanted material. The decanted solvent was rotary evaporated off. The material was washed 4 times with 10 mL of hexanes. 5 mL of $H_2O$ was added and the precipitate was suction filtered. The precipitate was washed 3 times with 10-15 mL of $H_2O$. To the precipitate (16.5 mgs) was added 1 mL of MeOH. The material was centrifuged with the solvent being decanted off. The decanted material was rotary evaporated off 14.21 mgs (25.48 umol) of CEN-372 was obtained for a % Yield of 44.4%. TLC: 75:25 DCM:EtOAc; RfCEN-372=0.0; Ninhydrin positive; HPLC Analysis: C18 Column: Atlantis®T3; 3 um; 4.6×150 mm; Gradient: 0-2 min=90:10 (A:B); 2-15 min=0:100 (A:B); Flow Rate: 1 mL/min; RtCEN-372=11.60 min (λmax=300 nm). $^1$H-NMR (400 MHz, DMSO-d6): δ 7.92 (d, 1H, H21), 7.51 (s, 1H, H14), 6.95 (s, 1H, H26), 6.27 (d, 1H, H20), 4.78 (s, 1H, H3), 4.15 (s, 1H, H13), 3-1.1 (multiple peaks, 39H, H1,2,4-9,11,12,15-17,27-34), 0.87 (s, 3H, H18), 0.59 (s, 3H, H19). TOF-MS (ESI): MWobs=558.39 g/mol; MWcalc.=558.84 g/mol. IUPAC Name: 5-[(1S,2S,5S,7R,10R,11S,14S,15R)-5-{3-[N-Methyl (3-aminopropyl)amino]propylaminocarbonyloxy}-11-hydroxy-2,15-dimethyltetracyclo[8.7.0.02,7.011,15]heptadec-14-yl]-2-pyranone v. CEN-373 Synthesis 21 mgs (37.93 µmol) of 4-nitrophenyl carbamate-3-O-bufalin was dissolved in 2 mL of DCM and 1.4 mL of MTBE. 26.6 µL (190 µmol) of Bis(3-aminopropyl)amine was added and stirred at room temperature. After 25 minutes 5 mL of MTBE was added and stirred for an additional 30 minutes. The precipitate was suction filtered off and washed with 10 mL MTBE. The precipitate was washed with 20 mL of DCM. The filtrate was rotary evaporated off 5 mL H$_2$O was added and suction filtered. The precipitate was washed with 30 mL of H$_2$O. The precipitate was dissolved in 1:1 DCM:MeOH mix (~5 mL) and the solvent was evaporated off 100 µL of H$_2$O was added to the material which was frozen and placed on a lyophilizer overnight. 9.57 mgs (17.6 µmol) of CEN-373 was obtained for a percent yield of 46.4%. TLC: 75:25 DCM:EtOAc; RfCEN-373=0.0; Ninhydrin positive; HPLC Analysis: C18 Column: Atlantis®T3; 3 um; 4.6×150 mm; Gradient: 0-2 min=90:10 (A:B); 2-15 min=0:100 (A:B); Flow Rate: 1 mL/min; RtCEN-373=11.70 min (λmax=300 nm). 1H-NMR (400 MHz, DMSO-d6): δ 7.92 (d, 1H, H21), 7.51 (s, 1H, H14), 6.99 (s, 1H, H26), 6.28 (d, 1H, H20), 4.79 (s, 1H, H3), 4.15 (s, 1H, H13), 3-1.1 (multiple peaks, 37H, H1,2,4-9,11,12,15-17,27-34), 0.85 (s, 3H, H18), 0.59 (s, 3H, H19). TOF-MS (ESI): MWobs=544.38 g/mol; MWcalc.=544.82 g/mol. IUPAC Name: 5-{(1S,2S,5S,7R,10R,11S,14S,15R)-5-[3-(3-Aminopropylamino)propylaminocarbonyloxy]-11-hydroxy-2,15-dimethyltetracyclo[8.7.0.02,7.011,15]heptadec-14-yl}-2-pyranone.

vi. CEN-375 Synthesis
(Activated-PEG24-CEN-371)

4.05 mgs (6.62 µmol) of CEN-371 in 170 µL of DMSO was added to 10.65 mgs (7.28 µmol) of MAL-PEG24-TFP ester (e.g., MAL-dPEG$_{24}$-TFP ester, 2,3,5,6-tetrafluorophenyl 1-(2,5-dioxo-2,5-dihydro-1H-pyrrol-1-yl)-3-oxo-7,10, 13,16,19,22,25,28,31,34,37,40,43,46,49,52, 55,58,61,64,67, 70,73,76-tetracosaoxa-4-azanonaheptacontan-79-oate, C$_{64}$H$_{108}$F$_4$N$_2$O$_{29}$, prod. no. 10554, Quanta Biodesign Ltd, Plain City, Ohio, USA) in 100 µL of DMSO. The reaction was stirred at room temperature for 90 minutes. After 90 minutes, an additional 5 mgs (3.42 µmol) of MAL-PEG24-TFP ester was added and allowed to react overnight. 15 mL of ether and 2 mL of DCM was added to the reaction, followed by 25 mL of hexanes. The reaction was placed at −20° C. for 1 hour. The material did not precipitate, so the solvent was rotary evaporated off. The reaction was resuspended in DMSO and purified by reverse-phase HPLC (Buffer A=1% Acetic Acid in H$_2$O; Buffer B=1% Acetic Acid in ACN). The solvent of the collected material was rotary evaporated off. The material was frozen and lyophilized overnight. 6.21 mgs (3.28 µmol) of CEN-375 was obtained for a % Yield of 49.6%. HPLC Analysis: C18 Column: Atlantis®T3; 3 um; 4.6×150 mm; Gradient: 0-1 min=80:20 (A:B); 1-19 min=10:90 (A:B); Flow Rate: 1 mL/min; RtCEN-375=12.87 min (λmax=301 nm). 1H-NMR (400 MHz, DMSO-d6): δ 8.05, (s, 1H, H42), 7.92 (d, 1H, H21), 7.8 (s, 1H, H37), 7.52 (s, 1H, H14), 7.03 (s, 1H, H26), 6.7 (d, 2H, H45,46), 6.28 (d, 1H, H20), 4.78 (s, 1H, H3), 4.13 (s, 1H, H13), 3.7-3.2 (m, PEG peaks), 3-1.1 (multiple peaks, 44H, H1,2,4-9,11,12,15-17,27-37), 0.89 (s, 3H, H18), 0.59 (s, 3H, H19). 13C NMR (500 MHz, CDCl3): δ 174.43, 173.28, 171.06, 170.73, 170.44, 169.59, 169.13, 162.29, 160.94, 156.24, 149.61, 148.49, 146.71, 134.17, 122.87, 122.60, 115.28, 86.07, 85.28, 78.63, 77.57, 70.6, 70.52, 70.47, 70.45, 70.34, 70.22, 70.19, 70.12, 69.61, 69.55, 68.81, 67.30, 64.32, 63.00, 56.95, 56.78, 53.40, 53.23, 53.06, 51.19, 49.71, 48.29, 44.83, 42.33, 42.01, 41.77, 40.82, 40.65, 40.50, 39.21, 38.60, 38.58, 38.37, 37.11, 36.92, 35.78, 35.67, 35.40, 35.15, 34.49, 34.26, 33.32, 32.75, 32.22, 30.75, 30.54, 28.68, 27.27, 26.41, 25.84, 25.81, 25.36, 25.32, 23.84, 21.39, 21.28, 21.23, 21.08. 16.50, 16.46. IUPAC Name: N/A.

vii. CEN-376 Synthesis
(Activated-PEG24-CEN-372)

8.2 mgs (14.7 µmol) of CEN-372 was dissolved in 300 µL of DMSO. 26.77 mgs (18.29 µmol) of MAL-PEG24-TFP ester was added to the reaction which was stirred at room temperature for 80 minutes. 7.5 mL of MTBE was added to the reaction along with 1 mL DCM. The reaction was placed at −20° C. After 1 hour the solution was removed and the solvent was decanted into a round bottom flask and removed through rotary evaporation. 450 µL of nanopure water was added to the material which contained unpurified product. This material was frozen and placed on a lyophilizer overnight. The material was resuspended in acetonitrile and purified by reverse-phase HPLC (Buffer A=1% Acetic Acid in H$_2$O; Buffer B=1% Acetic Acid in ACN). The solvent of the collected material was rotary evaporated off. The material was frozen and lyophilized overnight. 0.89 mgs (0.484 µmol) of CEN-376 was obtained for a % Yield of 3.3%. HPLC Analysis: C18 Column: Atlantis®T3; 3 um; 4.6×150 mm; Gradient: 0-2 min=90:10 (A:B); 2-15 min=0:100 (A:B); Flow Rate: 1 mL/min; RtCEN-376=12.65 min (λmax=300 nm). IUPAC Name: N/A.

viii. CEN-377 Synthesis
(Activated-PEG24-CEN-373)

4.0 mgs (7.36 µmol) of CEN-373 in 200 µL of DMSO was added to 12.0 mgs (8.26 µmol) of MAL-PEG24-TFP ester. The reaction was stirred at room temperature for 90 minutes. 7.5 mL of MTBE was added to the reaction which was then placed at −20° C. for 2 hours. The liquid was decanted off and the precipitate was washed 4 times with 10 mL of MTBE. The solvent was rotary evaporated off and resuspended in 120 µL DMSO. The material was purified by HPLC. The solvent of the collected fractions were removed through rotary evaporation. 400 µL of H$_2$O was added. The solution was frozen and placed on a lyophilizer overnight. 0.6 mgs (0.329 µmol) of CEN-377 was obtained. for a % Yield of 4.47%. HPLC Analysis C18 Column: Atlantis®T3; 3 um; 4.6×150 mm; Gradient: 0-2 min=90:10 (A:B); 2-15 min=0:100 (A:B); Flow Rate: 1 mL/min; RtCEN-377=12.47 min (λmax=300 nm). IUPAC Name: N/A.

ix. CEN-381 Synthesis 161.35 mgs (300 µmol) of 4-nitrophenyl carbamate-3-O-digitoxigenin § was reacted with 88.94 µL (432 µmol) of 1,4-Bis(3-aminopropyl)piperazine by stirring at room temperature for 2 hours in 20.77 mL DCE, 14.23 mL DCM and 35 mL of Hexanes. The reaction was placed at 4° C. for 2 days. The precipitate was removed through suction filtration and washed with ~20 mL of hexanes. To the filtrate was added 24.94 µL (432 µmol) of glacial acetic acid. The solvent was rotary evaporated off and resuspended in MeOH. The material was purified by reverse-phase HPLC (Buffer A=1% Acetic Acid in $H_2O$; Buffer B=1% Acetic Acid in ACN). The solvent of the collected material was rotary evaporated off. The material was frozen and lyophilized overnight. 109.43 mgs (182.13 µmol) of CEN-381 was obtained for a % Yield of 60.71%. TLC: 75:25 DCM:EtOAc; RfCEN-381=0.0; Ninhydrin positive; HPLC Analysis: C18 Column: Atlantis®T3; 3 um; 4.6×150 mm; Gradient: 0-2 min=90:10 (A:B); 2-14 min=0:100 (A:B); Flow Rate: 1 mL/min; RtCEN-381=11.53 min (λmax=220 nm). IUPAC Name: 4-(3-{(1S,2S,5S,7R,10R,11S,14R,15R)-11-Hydroxy-2,5,14,15-tetramethyl-14-(5-oxo-2H-fur-3-yl)tetracyclo[8.7.0.02,7.011,15]heptadec-5-yloxycarbonylamino}propyl)-1-(3-aminopropyl)piperazine.

x. CEN-382 Synthesis
(Activated-PEG24-CEN-381)

15 mgs (24.97 µmol) of CEN-381 was dissolved in 1.6 mL of DCM. 42.46 mgs (29.01 µmol) of MAL-PEG24-TFP ester was added to the reaction. The reaction was stirred at room temperature for 3 hours. An additional 2 mgs (1.37 µmol) of MAL-PEG24-TFP ester was added and allowed to react for 30 minutes. The reaction was heated to ~40-50° C. and the cap removed to help facilitate evaporation of the DCM. The material was resuspended in 300 µL of MeOH and purified by reverse-phase HPLC (Buffer A=1% Acetic Acid in $H_2O$; Buffer B=1% Acetic Acid in ACN). The solvent of the collected material was rotary evaporated off. The material was frozen and lyophilized overnight. 39.38 mgs (20.94 µmol) of CEN-382 was obtained for a % Yield of 83.86%. HPLC Analysis: C18 Column: Atlantis®T3; 3 um; 4.6×150 mm; Gradient: 0-2 min=90:10 (A:B); 2-16 min=0:100 (A:B); Flow Rate: 1 mL/min; RtCEN-382=13.20 min (λmax=218 nm). IUPAC Name: N/A.

xi. Synthesis of SUN4B7-PEG24-CEN-371

SUN4B7 Buffer Exchange: ~0.8 mL (1.2 mgs) of SUN4B7 in PBS buffer was added to 30 k MWCO centrifugal filters and spun down to ~35-45 µL. The filtrate was discarded and 0.4 mL of 150 mM sodium acetate (pH=6.5) was added to the SUN4B7. The centrifugation process was repeated two more times, with the filtrate discarded each time. The SUN4B7 was removed and the filter was washed two times with ~60-70 µL each time with 150 mM sodium acetate (pH=6.5). The total working volume is ~140 µL. UV-VIS determination showed a concentration of 8.80 mg/mL (~1.2 mgs). 0.67 µL of DTPA was added to the SUN4B7 followed by the addition of 140 µL of 150 mM sodium acetate/1.2M sodium citrate (pH=7.8). The final concentration of SUN4B7 was 4.40 mg/mL with a final buffer of 150 mM sodium acetate/600 mM sodium citrate (pH=7.5).

SUN4B7 Reduction: The SUN4B7 (4.40 mg/mL; 8.21 nmol) was placed at 0-8° C. for ~5 minutes. 4.11 µL (41.1 nmol; 5 eq to SUN4B7) of a 10 mM TCEP solution in nanopure water was added followed by slight agitation for 5-10 seconds. The solution was heated to 37° C. over 30 minutes. When the solution had reached 37° C., the reaction was allowed to react for an additional 2 hours. The reduced SUN4B7 was removed from 37° C. and placed at room temperature.

CEN-375 Conjugation to SUN4B7: 21 µL (84 nmol; 10.2 eq to SUN4B7) of a 4 mM solution of CEN-375 in a solution of IPA:$H_2O$ (1:1) containing 25 mM sodium acetate (pH=5.5) was added to reduced SUN4B7. The reaction was agitated slightly for 5-10 seconds and allowed to sit for 2 hours at room temperature. 360 µL of 150 mM sodium acetate (pH=6.5) was added to the reaction and was allowed to sit for an additional 20 minutes. The reaction was placed into 30 k MWCO centrifugal filters where it was spun down to ~35-40 µL. 0.4 mL of DPBS was added and centrifuged down to 35-40 µL. This was repeated 4 more times. The final product was placed in a vial and the centrifugal filter was washed with ~340 µL DPBS buffer. The final volume of SUN4B7(CEN-375) in DPBS was 360 µL. UV-VIS analysis showed a drug-to-antibody ratio (DAR) of 5.02 at a concentration of 3.33 mg/mL (22.18 µM). Hydrophobic Interaction Chromatography (HIC) analysis showed a DAR value of 5.36 with 4.86% consisting of unlabeled SUN4B7. UV-VIS (299/280) showed a DAR value of 5.02 at a concentration of 3.33 mg/mL (22.18 uM).

CEN-382 Conjugation to SUN4B7: A similar procedure to "CEN-375 Conjugation to SUN4B7" described immediately above was performed with similar results.

Example 3

Cytotoxicity of Agents and Agent-Linker Intermediates in In Vitro Models

Cytotoxicities of select agents and agent-linker intermediates were assessed using an in vitro cancer cell cytotoxicity analysis. Cells were plated in 384-well white tissue culture treated microtiter plates in 20 µL of complete media with or without 250 nM all-trans-retinoic acid (ATRA) at the following densities: 2000 (Ramos, SU-DH-8, HL60) cells per well, 1500 (Hut78) cells per well, and 1333 (H929) cells per well. These cells where equilibrated for 24 hour at 37° C. with 5% $CO_2$ in a humidified incubator before addition of test compounds. Compounds and/or mouse plasma samples were serially diluted in complete media at 5× final working concentrations, and 5 µL of each were added to the cells used in the assay. Treated cells were incubated for 3 days before cell viability testing. Cell viability testing used the CellTiter-Glo luminescent cell viability assay (Promega, Madison, Wis.). EC50 values of the agents to each cell line were determined using GraphPad Prism 5 software and are shown in Table 3.

TABLE 3

Cytotoxicities of Select Agents and Agent-Linker Intermediates

| Agent/Agent-Linker Intermediate | Structure | EC50 in picoM (% viab.) | |
|---|---|---|---|
| | | Ramos | SUDHL8 |
| CEN09-106 | | 1,900 (0) | 2,070 (0) |
| CEN-319 | | 5,800 (0) | 8,400 (ND) |
| CEN-371 | | 7,805 (0) | 11,000 (0) |
| CEN-372 | | 3,600 | 4,400 |

TABLE 3-continued
Cytotoxicities of Select Agents and Agent-Linker Intermediates
| Agent/Agent-Linker Intermediate | Structure | EC50 in picoM (% viab.) | |
| --- | --- | --- | --- |
| | | Ramos | SUDHL8 |
| CEN-373 | 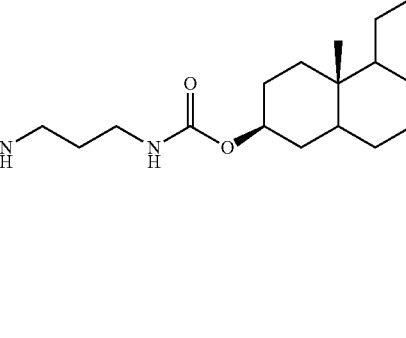 | 4,000 | 5,900 |
| CEN-381 | 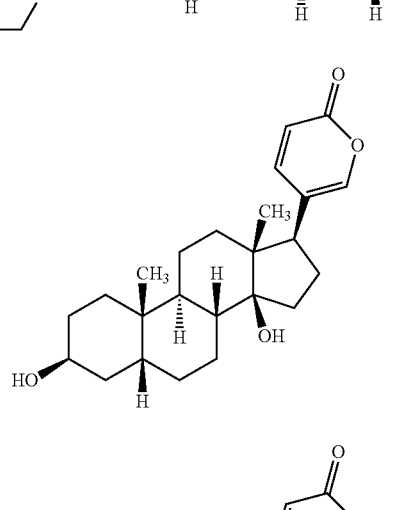 | >50,000 | >50,000 |
| Bufalin | 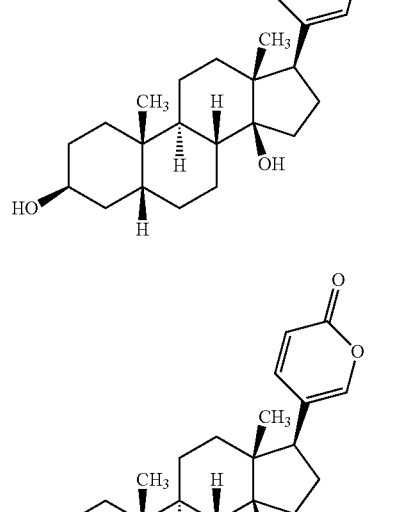 | 7,300 | 16,000 |
| Scillarenin | 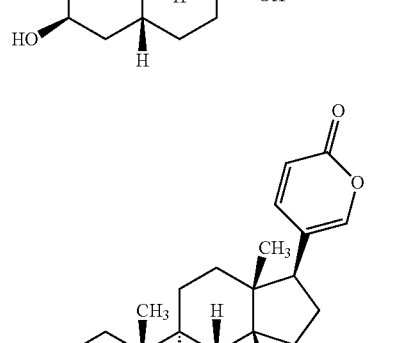 | 17,000 | 18,000 |

TABLE 3-continued

Cytotoxicities of Select Agents and Agent-Linker Intermediates

| Agent/Agent-Linker Intermediate | Structure | EC50 in picoM (% viab.) | |
|---|---|---|---|
| | | Ramos | SUDHL8 |
| Digitoxigenin | [structure of digitoxigenin] | >50,000 | >50,000 |

Example 4

Cytotoxicity of Select EDCs

Cytotoxicities of select EDCs of Formula (I) were assessed using an in vitro cancer cell cytotoxicity analysis. Structures for each of the EDCs listed in Table 4 are shown in FIG. 1. Agent loading was determined to be approximately 4. Cells were plated in 384-well white tissue culture treated microtiter plates in 20 μL of complete media with or without 250 nM all-trans-retinoic acid (ATRA) at the following densities: 2000 (Ramos, SU-DH-8, HL60) cells per well, 1500 (Hut78) cells per well, 1333 (H929) and 1500 (MV-4-11) cells per well. These cells where equilibrated for 24 hour at 37° C. with 5% $CO_2$ in a humidified incubator before addition of test compounds. Compounds and/or mouse plasma samples were serially diluted in complete media at 5× final working concentrations, and 5 μL of each were added to the cells used in the assay. Treated cells were incubated for 3 days before cell viability testing. Cell viability testing used the CellTiter-Glo luminescent cell viability assay (Promega, Madison, Wis.). EC50 values of the agents to each cell line were determined using GraphPad Prism 5 software and are shown in Table 4. Select data is also shown graphically (logarithmic transform) in some cases compared to unconjugated SUN4B7, unconjugated therapeutic agents, unconjugated bufalin, and/or control EDC manufactured with antibody 4F12, in FIGS. 2, 3, 4, 9 and 10.

TABLE 4

Cytotoxicities of Select EDCs

| Targeting Moiety | Linker-Agent Includes: | EC50 in picoM (% viab.) | |
|---|---|---|---|
| | | Ramos | SUDHL8 |
| SUN4B7 | PEG24, CEN09-106 | 120 (0) | 38 (0) |
| SUN4B7 | PEG36, CEN09-106 | 43 (0) | 14 (0) |
| SUN4B7 | PEG24, CEN-319 | 1,400 (17) | 280 (50) |

TABLE 4-continued

Cytotoxicities of Select EDCs

| Targeting Moiety | Linker-Agent Includes: | EC50 in picoM (% viab.) | |
|---|---|---|---|
| | | Ramos | SUDHL8 |
| SUN4B7 | PEG36, CEN-319 | 160 (3) | 45 (15) |
| SUN4B7 | PEG24, CEN-371 | 90 (0) | 139 (0) |
| SUN4B7 | PEG24, CEN-381 | 3,300 (50) | 6,200 (50) |

Example 5

Cytotoxicity of Select EDCs to Cells Expressing CD38

To determine if the epitope for the targeting moiety is important for EDC of the present disclosure, and to determine if all-trans-retinoic acid (ATRA) can enhance the activity of EDC of the invention, the following studies were conducted. Four different anti-CD38 antibodies specific to different CD38 epitopes were conjugated to CEN09-106 via PEG36 containing linkers. The general structure for the resulting EDCs is shown in FIG. 1. Agent loading was determined to be about 4. Each EDC was tested on six human blood cancer cell types (HL60, U937, MV411, Hut78, H929, and RAMOS). All-trans retinoic acid (ATRA) is a known inducer of CD38 (Ferrero E, Malavasi F. (2002) *A Natural History of the Human CD38 Gene.* Kluwer Academic Publishers, Norwell, Mass., pp. 81-99). Therefore these EDCs were tested for cytotoxic activity in vitro on a variety of cell types with and without ATRA induction and the EC50's in picomolar and the percent viable cells after 72 hours of EDC exposure are shown (see Table 5).

TABLE 5

EC50 Cyctotoxicities of Select [TM]-PEG36-CEN09-106 EDCs

| | [TM] Targeting Moiety | | | | | | | |
|---|---|---|---|---|---|---|---|---|
| | SUN4B7 | | OKT10 | | IB4 | | HB7 | |
| Cell Line | NO ATRA | ATRA | NO ATRA | ATRA | NO ATRA | ATRA | NO ATRA | ATRA |
| HL60 (AML) | N/A | 80 (15) | N/A | 800 (20) | N/A | N/A | N/A | N/A |
| U937 (AML) | N/A | 140 (5) | N/A | 1090 (10) | N/A | N/A | N/A | N/A |
| MV411 (AML) | N/A | 100 (0) | ND* | ND* | ND* | ND* | ND* | ND* |
| Hut78 (CTCL) | N/A | 120 (5) | N/A | 310 (5) | N/A | 210 (10) | N/A | 290 (10) |
| H929 (MM) | 140 (10) | 80 (0) | 1900 (20) | 440 (0) | 1300 (30) | 180 (20) | 49000 (50) | 330 (30) |
| RAMOS | 40 (0) | 40 (0) | 140 (0) | 120 (0) | 140 (0) | 120 (0) | 200 (0) | 160 (0) |

N/A = No activity observed.
ND* = Not Determined.
( ) = percent viable cells after exposure.

In this study, all naked antibodies under all conditions were found to be inactive under all conditions. In this study, ATRA alone slowed cell growth on all cell lines tested except RAMOS and adding ATRA to RAMOS cells did not increase their sensitivity to and EDC tested. In this study and as determined by antibody cell staining, and with the exception of HL-60 cells, all cells expressed various levels of cell surface CD38 prior to ATRA addition. With the exception of RAMOS, all cell lines tested in this study increased CD38 expression and thus displayed enhanced activity to EDC (lower EC50 values and fewer remaining cells viable).

These data demonstrate that EDCs produced with SUN4B7 were the most potent at inducing apoptosis in the cell lines expressing CD38 on the cell surface. These data also demonstrate that ATRA can enhance cell sensitivity to the EDCs.

Example 6

In Vivo Pharmacokinetics of Select EDCs

Figure 5:
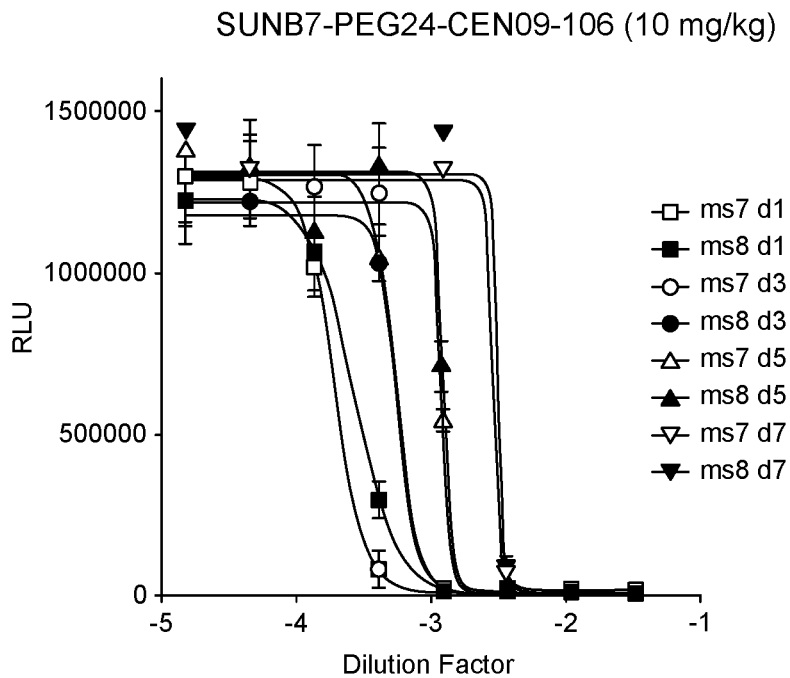
FIG. 5 is a pharmacokinetic plot for one EDC (SUN4B7-PEG24-CEN09-106) according to the present disclosure.
Figure 6:
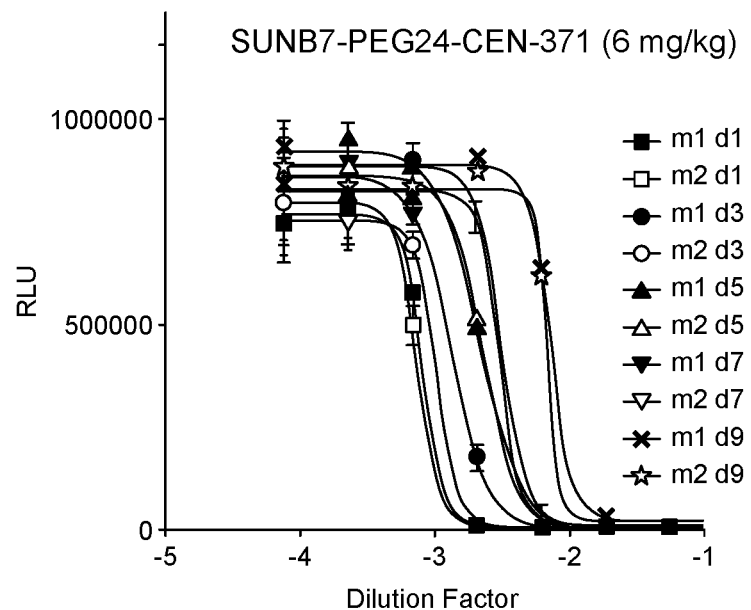
FIG. 6 is a pharmacokinetic plot for one EDC (SUN4B7-PEG24-CEN371) according to the present disclosure.

To examine the pharmacokinetics of various EDCs of the present disclosure, three EDCs were administered to laboratory mice and the blood examined for the presence of active EDC at various time points post administration. EDCs SUN4B7-PEG24-CEN-319, SUN4B7-PEG24-CEN09-106 and SUN4B7-PEG24-CEN-317 (agent loading: about 4 for each EDC) were separately administered to 2 mice each at a single IP dose of 6 mg/kg and the blood draw and various time points and tested for the presence of active EDC by in vitro testing. The results of this study are shown graphically in FIGS. 5-6. The in vivo half-life of SUN4B7-PEG24-CEN-319, SUN4B7-PEG24-CEN09-106 and SUN4B7-PEG24-CEN-317 were not able to be calculated, 37 hours or 69 hours, respectively. In addition the results showed that SUN4B7-PEG24-CEN09-106 and SUN4B7-PEG24-CEN-317 maintained their full activity (ability to kill >99% of the cells) during the time points tested, while SUN4B7-PEG24-CEN-319 lost its activity after 24 hours (i.e., more than 30% of the cells remained viable). These data indicate that SUN4B7-PEG24-CEN-317 is a preferred EDC. This means that an EDC could be administered at 0.1 to 10 mgs/kg and as infrequently as once every two weeks.

Example 7

In Vivo Efficacy of Select EDCs

To examine the in vivo efficacy of various EDCs disclosed herein, two EDCs constructed using SUN4B7 as the targeting moiety (SUN4B7-PEG24-CEN-319 and SUN4B7-PEG24-CEN09-106; agent loading: about 4 for each EDC) compared to unconjugated SUN4B7, CHOP (a standard of care for lymphoma consisting of a mixture of cyclophosphamide, doxorubicin, vincristine and prednisone), and a vehicle group.

Laboratory mice were implanted with Ramos tumor cells and bearing tumors averaging in size around 250 mm$^3$ were monitored. After tumors reached an average size of 250 mm$^3$, five mice in each group were each administered an EDC (diluted in PBS and administered at 10 mg/kg every 5 days four times), unconjugated SUN4B7 (diluted in PBS and administered at 10 mg/kg every 5 days four times), vehicle (PBS administered at 10 mg/kg every 5 days four times), or CHOP one time at 30 mg/kg cyclophosphamide, 2.475 mg/kg doxorubicin, 0.375 mg/kg vincristine and P every day five times at 0.15 mg/kg prednisone.

Figure 7:
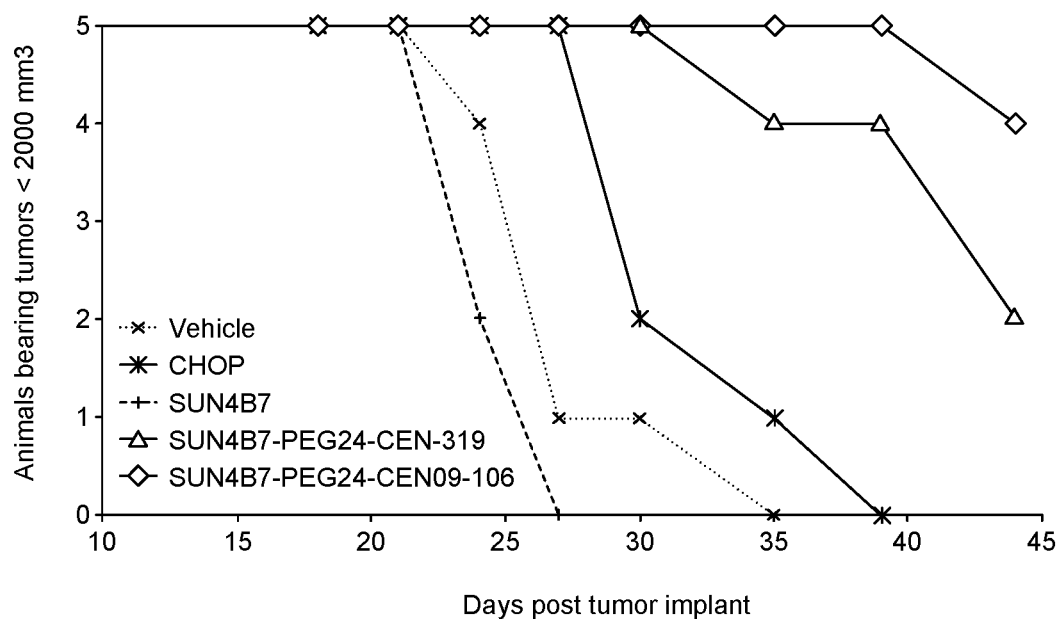
FIG. 7 is a plot of the number of tumor-induced animals having tumors less than 2,000 $mm^3$ in size as a function of the number of days post-tumor implant for various EDCs of the present disclosure.
Figure 8:
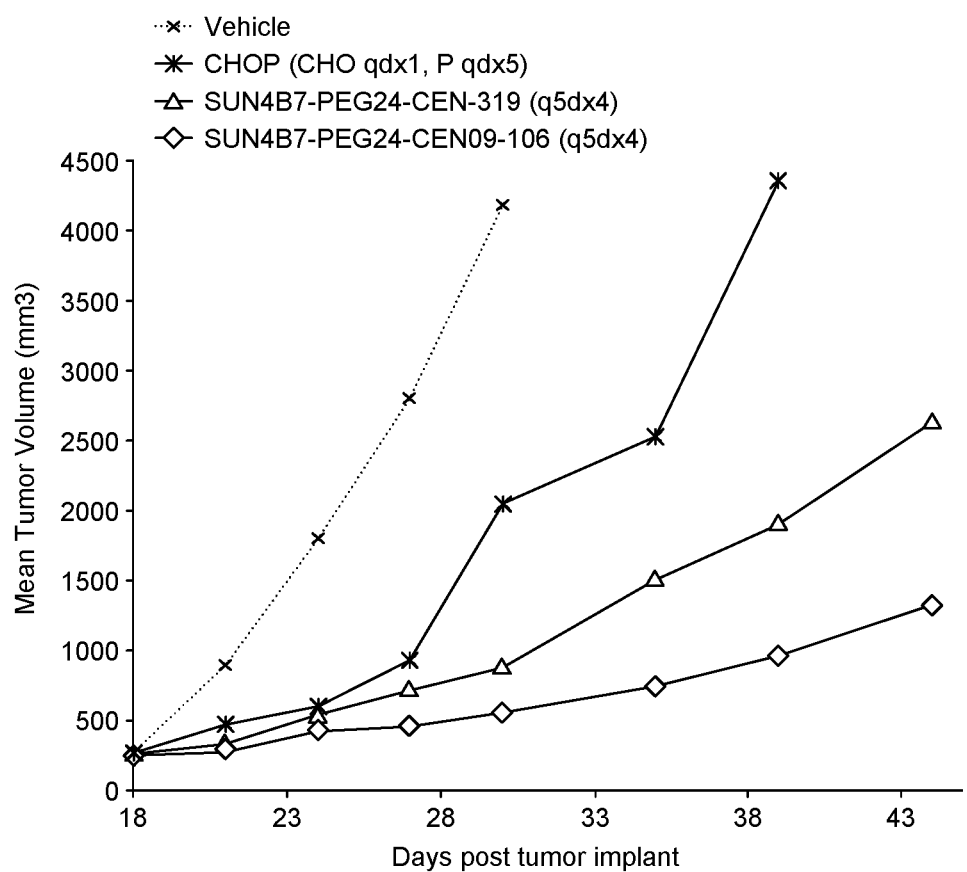
FIG. 8 is a plot of mean tumor volume as a function of the number of days post-tumor implant for various EDCs of the present disclosure.
Figure 9:
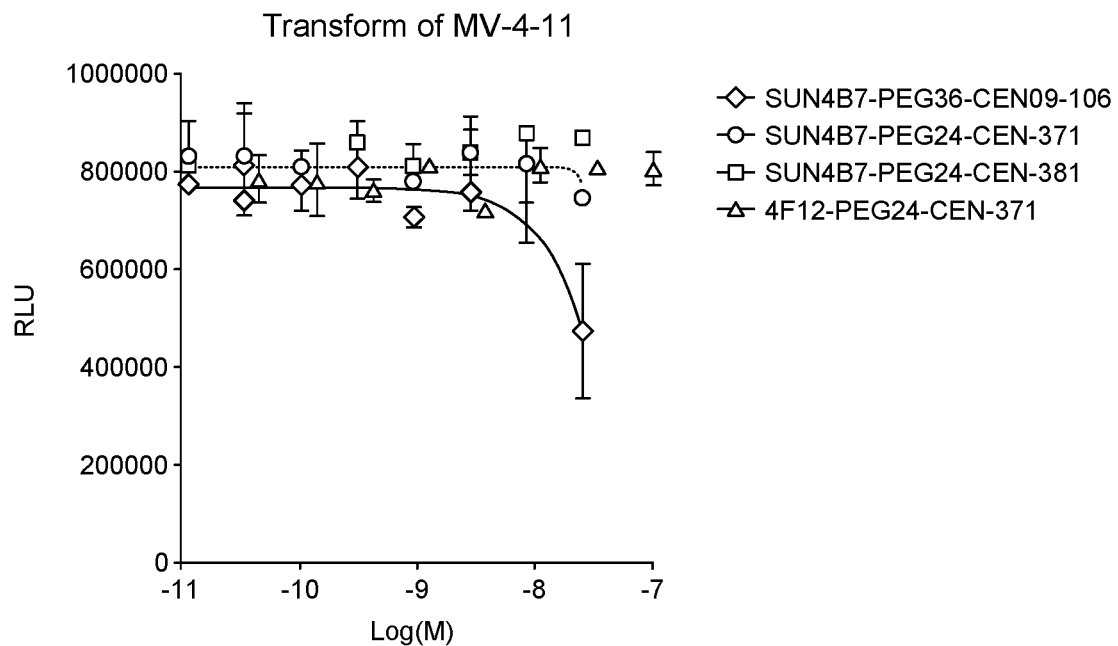
FIG. 9 is a comparison of in vitro activities for anti-CD38 targeted EDCs of the present disclosure in human acute myeloid leukemia cell line MV4-11 without the addition of ATRA.
Figure 10:
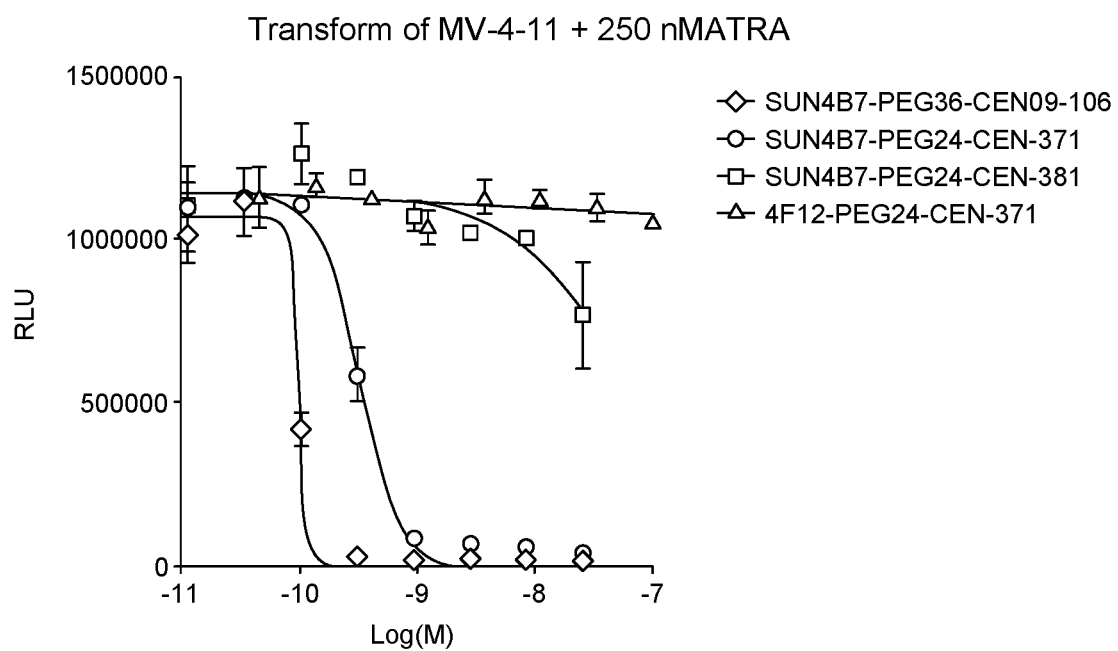
FIG. 10 is a comparison of in vitro activities for anti-CD38 targeted EDCs of the present disclosure in cell line MV4-11 with the addition of ATRA.

As shown in FIG. 7, when comparing animals in the five groups, groups receiving an EDC bore tumors smaller than 2,000 mm$^3$ after 45 days day than did groups receiving CHOP, unconjugated SUN4B7 or vehicle. Similarly, as shown in FIG. 8, tumors grew much more slowly in groups administered an EDC compared to groups administered CHOP, unconjugated SUN4B7 or vehicle.

These data indicate that both EDCs reduce tumor growth in a superior manner when compared to CHOP, the standard of care and administered at a safe dose to mice.

Cell lines and cell culture: Cell lines Ramos (ATCC number—CRL-1596), SU-DHL-8 (ATCC number—CRL-2961), U937 (ATCC number—CRL-1596.2), Hut78 (ATCC number—TIB-161), H929 (ATCC number—CRL-9078), HL60 (ATCC number—CCL-240) and MV-4-11 (ATCC number CRL-9591) were maintained in complete media [RPMI medium 1640 supplemented with 10% (wt/vol) fetal bovine serum and gentamycin (30 μg/ml)] at a density between 1×10$^5$ and 1×10$^6$ cells per mL at 37° C. with 5% CO$_2$ in a humidified incubator.

In vitro cancer cell cytotoxicity analysis: Cells were plated in 384-well white tissue culture treated microtiter plates in 20 uls complete media with or without 250 nM all-trans-retinoic acid (ATRA) at the following densities: 2000 (Ramos, SU-DH-8, HL60), 1500 (Hut78), 1333 (H929) and 1500 (MV-4-11) cells per well. These cells where equilibrated for 24 hour at 37° C. with 5% CO$_2$ in a humidified incubator before addition of test compounds. Compounds and/or mouse plasma samples were serially diluted in complete media at 5× final working concentrations, and 5 μl added to the cells used in the assay. Treated cells were incubated for 3 days before cell viability testing. Cell viability testing used the CellTiter-Glo luminescent cell viability assay (Promega, Madison, Wis.). EC50 values of the agents to each cell line were determined using GraphPad Prism 5 software.

Pharmacokinetics. The pharmacokinetics of SUN4B7-PEG-24-CEN-319, SUN4B7-PEG-24-CEN09-106, and SUN4B7-PEG-24-CEN-371 (agent loading: about 4 for each EDC) were evaluated in Balb/c mice. Balb/c mice (n=2) were administered 10 mg/kg test material (SUN4B7-PEG-24-CEN-319) or 6 mg/kg (SUN4B7-PEG-24-CEN09-106 and SUN4B7-PEG-24-CEN-371) by intraperitoneal (IP) injection. Blood samples were collected from each mouse via retro-orbital bleed using heparinized hematocrit tubes at 24 hours, 72 hours, 120 hours, and 168 hours after injection. Blood was centrifuged (5,000×g, 5 minutes) to isolate plasma. Persistence of active conjugate in mouse blood was assayed by establishing the plasma dilution factor (for each bleed) that yielded an EC50 in a cytotoxicity assay of the B-cell lymphoma cell line Ramos, half-life was then calculated as the time required for cytotoxic activity of the of compound present in mouse blood to decrease by half.

Efficacy: Ramos lymphoma cells ($10^7$) in phosphate buffered saline were injected subcutaneously into the flank of 5 to 7 week-old female Crl:SHO-PrkdcscidHrhr mice (Charles River Laboratories, Wilmington, Mass.) in a volume of 0.1 mL/mouse. Treatment was initiated when the tumor volume in groups of 5 animals averaged ~250 mm$^3$ (18 days post tumor implantation). SUN4B7, SUN4B7-PEG24-CEN-319, and SUN4B7-PEG24-CEN09-106 were dosed at 10 mg/kg q5dx4. CHOP treatment consisted of a single intraperitoneal injection of 30 mg/kg cyclophosphamide, 2.475 mg/kg doxorubicin, 0.375 mg/kg vincristine, and daily dosing of prednisone at 0.15 mg/kg for 5 days. Tumor volumes were measured twice weekly for each group using vernier calipers and tumor volumes were calculated using the formula $V=(W^2 \times L)/2$; where V is tumor volume, W is tumor width, L is tumor length.

The invention claimed is:

1. An extracellular-targeted drug conjugate (EDC) comprising a targeting moiety linked by a PEG24 or PEG36 linker to an agent, wherein the targeting moiety binds a CD38 epitope and is daratumamab, SUN4B7, HB7 or AT1 and the agent is selected from bufalin, digitoxigenin, and scillarenin.

2. The EDC of claim 1 wherein the EDC is capable of binding to a CD38-Na,K-ATPase complex on a cancer cell surface.

3. An extracellular-targeted drug conjugate (EDC) comprising a targeting moiety linked by a PEG24 or PEG36 linker to an agent, wherein the targeting moiety is daratumamab or monoclonal, humanized or chimeric SUN4B7, the agent comprises bufalin, digitoxigenin, or scillarenin and wherein the EDC is capable of binding to a CD38-Na,K-ATPase complex on a cancer cell surface.

4. An extracellular-targeted drug conjugate (EDC) comprising a targeting moiety linked by a PEG24 to an agent, wherein the targeting moiety comprises humanized, monoclonal or chimeric SUN4B7 and the agent comprises

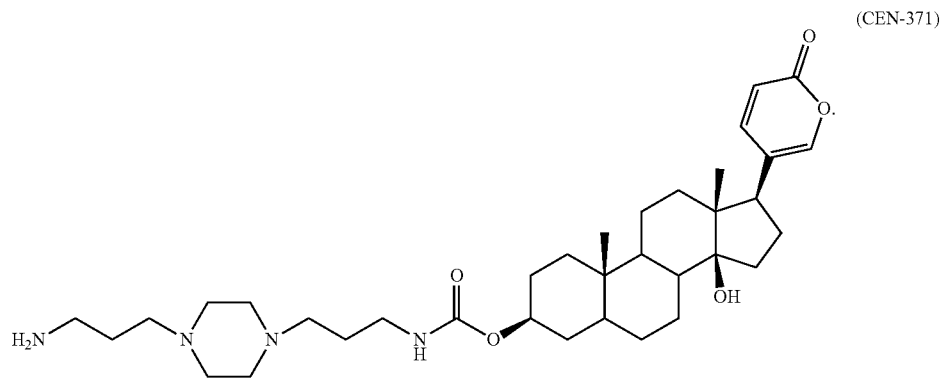 [SMILES: C[C@]12CC[C@H](OC(=O)NCCCN3CCN(CCCN)CC3)CC1CCC1C2CC[C@]2(C)[C@@H](c3ccc(=O)oc3)CC[C@]12O]

(CEN-371)

SEQUENCE LISTING

```
<160> NUMBER OF SEQ ID NOS: 3

<210> SEQ ID NO 1
<211> LENGTH: 903
<212> TYPE: DNA
<213> ORGANISM: Homo sapiens

<400> SEQUENCE: 1
atggccaact gcgagttcag cccggtgtcc ggggacaaac cctgctgccg gctctctagg      60
agagcccaac tctgtcttgg cgtcagtatc ctggtcctga tcctcgtcgt ggtgctcgcg     120
gtggtcgtcc cgaggtggcg ccagcagtgg agcggtccgg gcaccaccaa gcgctttccc     180
gagaccgtcc tggcgcgatg cgtcaagtac actgaaattc atcctgagat gagacatgta     240
gactgccaaa gtgtatggga tgctttcaag ggtgcattta tttcaaaaca tccttgcaac     300
attactgaag aagactatca gccactaatg aagtttggga ctcagaccgt accttgcaac     360
aagattcttc tttggagcag aataaaagat ctggcccatc agttcacaca ggtccagcgg     420
gacatgttca ccctggagga cacgctgcta ggctaccttg ctgatgacct cacatggtgt     480
ggtgaattca acacttccaa aataaactat caatcttgcc cagactggag aaaggactgc     540
agcaacaacc ctgtttcagt attctggaaa acggtttccc gcaggtttgc agaagctgcc     600
tgtgatgtgg tccatgtgat gctcaatgga tcccgcagta aaatctttga caaaaacagc     660 actttggga gtgtggaagt ccataatttg caaccagaga aggttcagac actagaggcc     720
tgggtgatac atggtggaag agaagattcc agagacttat gccaggatcc caccataaaa     780
gagctggaat cgattataag caaaaggaat attcaatttt cctgcaagaa tatctacaga     840
cctgacaagt ttcttcagtg tgtgaaaaat cctgaggatt catcttgcac atctgagatc     900
tga                                                                  903

<210> SEQ ID NO 2
<211> LENGTH: 300
<212> TYPE: PRT
<213> ORGANISM: Homo sapiens

<400> SEQUENCE: 2

Met Ala Asn Cys Glu Phe Ser Pro Val Ser Gly Asp Lys Pro Cys Cys
1               5                   10                  15
```

-continued

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
 50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 3
<211> LENGTH: 301
<212> TYPE: PRT
<213> ORGANISM: Macaca fascicularis

<400> SEQUENCE: 3

Met Ala Asn Cys Glu Phe Ser Pro Val Ser Gly Asp Lys Pro Cys Cys
1               5                   10                  15

Arg Leu Ser Arg Arg Ala Gln Val Cys Leu Gly Val Cys Leu Leu Val
            20                  25                  30

Leu Leu Ile Leu Val Val Val Ala Val Val Leu Pro Arg Trp Arg
        35                  40                  45

Gln Gln Trp Ser Gly Ser Gly Thr Thr Ser Arg Phe Pro Glu Thr Val
 50                  55                  60

Leu Ala Arg Cys Val Lys Tyr Thr Glu Val His Pro Glu Met Arg His
 65                  70                  75                  80

Val Asp Cys Gln Ser Val Trp Asp Ala Phe Lys Gly Ala Phe Ile Ser
                85                  90                  95

```
Lys Tyr Pro Cys Asn Ile Thr Glu Glu Asp Tyr Gln Pro Leu Val Lys
            100                 105                 110

Leu Gly Thr Gln Thr Val Pro Cys Asn Lys Thr Leu Leu Trp Ser Arg
            115                 120                 125

Ile Lys Asp Leu Ala His Gln Phe Thr Gln Val Gln Arg Asp Met Phe
        130                 135                 140

Thr Leu Glu Asp Met Leu Leu Gly Tyr Leu Ala Asp Asp Leu Thr Trp
145                     150                 155                 160

Cys Gly Glu Phe Asn Thr Phe Glu Ile Asn Tyr Gln Ser Cys Pro Asp
                    165                 170                 175

Trp Arg Lys Asp Cys Ser Asn Asn Pro Val Ser Val Phe Trp Lys Thr
                180                 185                 190

Val Ser Arg Arg Phe Ala Glu Thr Ala Cys Gly Val Val His Val Met
            195                 200                 205

Leu Asn Gly Ser Arg Ser Lys Ile Phe Asp Lys Asn Ser Thr Phe Gly
        210                 215                 220

Ser Val Glu Val His Asn Leu Gln Pro Glu Lys Val Gln Ala Leu Glu
225                     230                 235                 240

Ala Trp Val Ile His Gly Gly Arg Glu Asp Ser Arg Asp Leu Cys Gln
                    245                 250                 255

Asp Pro Thr Ile Lys Glu Leu Glu Ser Ile Ile Ser Lys Arg Asn Ile
                260                 265                 270

Arg Phe Phe Cys Lys Asn Ile Tyr Arg Pro Asp Lys Phe Leu Gln Cys
            275                 280                 285

Val Lys Asn Pro Glu Asp Ser Ser Cys Leu Ser Gly Ile
        290                 295                 300
```